(12) United States Patent
Lau

(10) Patent No.: US 7,158,839 B2
(45) Date of Patent: Jan. 2, 2007

(54) CARDIAC HARNESS FOR TREATING HEART DISEASE

(75) Inventor: Lilip Lau, Los Altos, CA (US)

(73) Assignee: Paracor Medical, Inc., Sunnyvale, CA (US)

( * ) Notice: Subject to any disclaimer, the term of this patent is extended or adjusted under 35 U.S.C. 154(b) by 284 days.

(21) Appl. No.: 10/795,574

(22) Filed: Mar. 5, 2004

(65) Prior Publication Data

US 2005/0102013 A1 May 12, 2005

Related U.S. Application Data

(63) Continuation-in-part of application No. 10/704,376, filed on Nov. 7, 2003.

(51) Int. Cl.
*A61N 1/05* (2006.01)

(52) U.S. Cl. .............................. 607/129; 600/16; 607/9

(58) Field of Classification Search ................ 607/129, 607/9; 600/16
See application file for complete search history.

(56) References Cited

U.S. PATENT DOCUMENTS

| | | | |
|---|---|---|---|
| 2,278,926 A | 4/1942 | Hartwell |
| 2,826,193 A | 3/1958 | Vineberg |
| 3,464,322 A | 9/1969 | Pequignot |
| 3,513,836 A | 5/1970 | Sausse |
| 3,587,567 A | 6/1971 | Schiff |
| 3,613,672 A | 10/1971 | Schiff |
| 3,966,401 A | 6/1976 | Hancock et al. |
| 3,983,863 A | 10/1976 | Janke et al. |
| 3,988,782 A | 11/1976 | Dardik et al. |
| 4,011,947 A | 3/1977 | Sawyer |
| 4,048,990 A | 9/1977 | Goetz |
| 4,065,816 A | 1/1978 | Sawyer |
| 4,108,161 A | 8/1978 | Samuels et al. |
| 4,192,293 A | 3/1980 | Asrican |
| 4,211,325 A | 7/1980 | Wright |
| 4,261,342 A | 4/1981 | Aranguren Duo |
| 4,306,318 A | 12/1981 | Mano et al. |
| 4,372,293 A | 2/1983 | Vijil-Rosales |
| 4,403,604 A | 9/1983 | Wilkinson et al. |
| 4,428,375 A | 1/1984 | Ellman |
| 4,512,471 A | 4/1985 | Kaster et al. |
| 4,536,893 A | 8/1985 | Parravicini |
| 4,545,783 A | 10/1985 | Vaughan |
| 4,628,937 A | 12/1986 | Hess et al. |
| 4,630,597 A | 12/1986 | Kantrowitz et al. |

(Continued)

FOREIGN PATENT DOCUMENTS

DE 3831 540 A1 4/1989

(Continued)

OTHER PUBLICATIONS

Bencini, Adriano, M.D., The "Pneumomassage" of the Heart, *Surgery*, vol. 39, No. 3, Mar. 1956.

(Continued)

*Primary Examiner*—Angela D. Sykes
*Assistant Examiner*—Alyssa M. Alter
(74) *Attorney, Agent, or Firm*—Fulwider Patton LLP

(57) ABSTRACT

A system for treating the heart includes a cardiac harness associated with a cardiac rhythm management devise which does not have a lead system. The cardiac harness applies a compressive force on the heart during diastole and systole, and the cardiac rhythm management devise will deliver an electrical shock to the heart for defibrillation and/or can be used for pacing/sensing. The cardiac harness and cardiac rhythm management devise are both delivered and implanted by minimally invasive access.

12 Claims, 35 Drawing Sheets

U.S. PATENT DOCUMENTS

| | | |
|---|---|---|
| 4,665,906 A | 5/1987 | Jervis |
| 4,690,134 A | 9/1987 | Snyders |
| 4,697,703 A | 10/1987 | Will |
| 4,750,619 A | 6/1988 | Cohen et al. |
| 4,821,723 A | 4/1989 | Baker, Jr. et al. |
| 4,827,932 A | 5/1989 | Ideker et al. |
| 4,834,707 A | 5/1989 | Evans |
| 4,838,288 A | 6/1989 | Wright et al. |
| 4,840,626 A | 6/1989 | Linsky et al. |
| 4,863,016 A | 9/1989 | Fong et al. |
| 4,878,890 A | 11/1989 | Bilweis |
| 4,936,857 A | 6/1990 | Kulik |
| 4,957,477 A | 9/1990 | Lundbäck |
| 4,960,424 A | 10/1990 | Grooters |
| 4,973,300 A | 11/1990 | Wright |
| 4,976,730 A | 12/1990 | Kwan-Gett |
| 5,031,762 A | 7/1991 | Heacox |
| 5,057,117 A | 10/1991 | Atweh |
| 5,067,957 A | 11/1991 | Jervis |
| 5,087,243 A | 2/1992 | Avitall |
| 5,098,369 A | 3/1992 | Heilman et al. |
| 5,106,386 A | 4/1992 | Isner et al. |
| 5,119,804 A | 6/1992 | Anstadt |
| 5,131,905 A | 7/1992 | Grooters |
| 5,150,706 A | 9/1992 | Cox et al. |
| 5,169,381 A | 12/1992 | Snyders |
| 5,186,711 A | 2/1993 | Epstein |
| 5,190,546 A | 3/1993 | Jervis |
| 5,192,314 A | 3/1993 | Daskalakis |
| 5,197,978 A | 3/1993 | Hess |
| 5,256,132 A | 10/1993 | Snyders |
| 5,279,539 A | 1/1994 | Bohan et al. |
| 5,290,217 A | 3/1994 | Campos |
| 5,336,254 A | 8/1994 | Brennen et al. |
| 5,344,442 A | 9/1994 | Deac |
| 5,352,184 A | 10/1994 | Goldberg et al. |
| 5,356,432 A | 10/1994 | Rutkow et al. |
| 5,366,460 A | 11/1994 | Eberbach |
| 5,383,840 A | 1/1995 | Heilman et al. |
| 5,385,156 A | 1/1995 | Oliva |
| 5,385,229 A | 1/1995 | Bittmann et al. |
| 5,385,528 A | 1/1995 | Wilk |
| 5,405,360 A | 4/1995 | Tovey |
| 5,429,584 A | 7/1995 | Chiu |
| 5,433,727 A | 7/1995 | Sideris |
| 5,456,711 A | 10/1995 | Hudson |
| 5,460,962 A | 10/1995 | Kemp |
| 5,500,015 A | 3/1996 | Deac |
| 5,507,779 A | 4/1996 | Altman |
| 5,509,428 A | 4/1996 | Dunlop |
| 5,524,633 A | 6/1996 | Heaven et al. |
| 5,533,958 A | 7/1996 | Wilk |
| 5,534,024 A | 7/1996 | Rogers et al. |
| 5,545,210 A | 8/1996 | Hess et al. |
| 5,558,617 A | 9/1996 | Heilman et al. |
| 5,571,215 A | 11/1996 | Sterman et al. |
| 5,582,616 A | 12/1996 | Bolduc et al. |
| 5,584,803 A | 12/1996 | Stevens et al. |
| 5,593,424 A | 1/1997 | Northrup, III |
| 5,593,441 A | 1/1997 | Lichtenstein et al. |
| 5,597,378 A | 1/1997 | Jervis |
| 5,603,337 A | 2/1997 | Jarvik |
| 5,607,477 A | 3/1997 | Schindler et al. |
| 5,647,372 A | 7/1997 | Tovey et al. |
| 5,647,380 A | 7/1997 | Campbell et al. |
| 5,695,525 A | 12/1997 | Mulhauser et al. |
| 5,702,343 A | 12/1997 | Alferness |
| 5,713,954 A | 2/1998 | Rosenberg et al. |
| 5,727,569 A | 3/1998 | Benetti et al. |
| 5,749,839 A | 5/1998 | Kovacs |
| 5,782,746 A | 7/1998 | Wright |
| 5,800,334 A | 9/1998 | Wilk |
| 5,800,528 A | 9/1998 | Lederman et al. |
| 5,814,097 A | 9/1998 | Sterman et al. |
| 5,824,028 A | 10/1998 | Knisley |
| 5,836,311 A | 11/1998 | Borst et al. |
| 5,848,962 A | 12/1998 | Feindt et al. |
| 5,849,005 A | 12/1998 | Garrison et al. |
| 5,853,422 A | 12/1998 | Huebsch et al. |
| 5,865,791 A | 2/1999 | Whayne et al. |
| 5,876,432 A | 3/1999 | Lau et al. |
| 5,904,690 A | 5/1999 | Middleman et al. |
| 5,910,124 A | 6/1999 | Rubin |
| 5,927,284 A | 7/1999 | Borst et al. |
| 5,948,019 A | 9/1999 | Shu et al. |
| 5,957,977 A | 9/1999 | Melvin |
| 5,961,440 A | 10/1999 | Schweich, Jr. et al. |
| 5,976,069 A | 11/1999 | Navia et al. |
| 5,979,456 A | 11/1999 | Magovern |
| 5,984,857 A | 11/1999 | Buck et al. |
| 5,990,378 A | 11/1999 | Ellis |
| 6,007,486 A | 12/1999 | Hunt et al. |
| 6,015,378 A | 1/2000 | Borst et al. |
| 6,024,096 A | 2/2000 | Buckberg |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,071,303 A | 6/2000 | Laufer |
| 6,076,013 A | 6/2000 | Brennan et al. |
| 6,077,214 A | 6/2000 | Mortier et al. |
| 6,077,218 A | 6/2000 | Alferness |
| 6,079,414 A | 6/2000 | Roth |
| 6,085,754 A | 7/2000 | Alferness et al. |
| 6,095,968 A | 8/2000 | Snyders |
| 6,110,100 A | 8/2000 | Talpade |
| 6,117,159 A | 9/2000 | Huebsch et al. |
| 6,117,979 A | 9/2000 | Hendriks et al. |
| 6,123,662 A | 9/2000 | Alferness et al. |
| 6,125,852 A | 10/2000 | Stevens et al. |
| 6,126,590 A | 10/2000 | Alferness |
| 6,155,968 A | 12/2000 | Wilk |
| 6,155,972 A | 12/2000 | Nauertz et al. |
| 6,162,168 A | 12/2000 | Schweich, Jr. et al. |
| 6,165,119 A | 12/2000 | Schweich, Jr. et al. |
| 6,165,120 A | 12/2000 | Schweich, Jr. et al. |
| 6,165,121 A | 12/2000 | Alferness |
| 6,165,122 A | 12/2000 | Alferness |
| 6,166,184 A | 12/2000 | Hendriks et al. |
| 6,169,922 B1 * | 1/2001 | Alferness et al. .............. 607/5 |
| 6,174,279 B1 | 1/2001 | Girard |
| 6,179,791 B1 | 1/2001 | Krueger |
| 6,183,411 B1 | 2/2001 | Mortier et al. |
| 6,190,408 B1 | 2/2001 | Melvin |
| 6,193,648 B1 | 2/2001 | Krueger |
| 6,206,820 B1 | 3/2001 | Kazi et al. |
| 6,214,047 B1 | 4/2001 | Melvin |
| 6,217,894 B1 | 4/2001 | Sawhney et al. |
| 6,221,103 B1 | 4/2001 | Melvin |
| 6,224,540 B1 | 5/2001 | Ledermann et al. |
| 6,230,714 B1 | 5/2001 | Alferness et al. |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,282,445 B1 | 8/2001 | Reinhardt et al. |
| 6,287,250 B1 | 9/2001 | Peng et al. |
| 6,293,906 B1 | 9/2001 | Vanden Hoek et al. |
| 6,306,141 B1 | 10/2001 | Jervis |
| 6,312,725 B1 | 11/2001 | Wallace et al. |
| 6,352,710 B1 | 3/2002 | Sawhney et al. |
| 6,360,749 B1 | 3/2002 | Jayaraman |
| 6,375,608 B1 | 4/2002 | Alferness |
| 6,390,976 B1 | 5/2002 | Spence et al. |
| 6,402,679 B1 | 6/2002 | Mortier et al. |
| 6,402,680 B1 | 6/2002 | Mortier et al. |

| | | |
|---|---|---|
| 6,406,420 B1 | 6/2002 | McCarthy et al. |
| 6,409,760 B1 | 6/2002 | Melvin |
| 6,416,459 B1 | 7/2002 | Haindl |
| 6,425,856 B1 | 7/2002 | Shapland et al. |
| 6,432,039 B1 | 8/2002 | Wardle |
| 6,451,025 B1 | 9/2002 | Jervis |
| 6,482,146 B1 | 11/2002 | Alferness et al. |
| 6,517,570 B1 | 2/2003 | Lau et al. |
| 6,537,203 B1 | 3/2003 | Alferness et al. |
| 6,544,168 B1 | 4/2003 | Alferness |
| 6,547,821 B1 | 4/2003 | Taylor et al. |
| 6,564,094 B1 | 5/2003 | Alferness et al. |
| 6,567,699 B1 | 5/2003 | Alferness et al. |
| 6,569,082 B1 | 5/2003 | Chin |
| 6,572,533 B1 | 6/2003 | Shapland et al. |
| 6,575,921 B1 | 6/2003 | Vanden Hoek et al. |
| 6,582,355 B1 | 6/2003 | Alferness et al. |
| 6,587,734 B1 | 7/2003 | Okuzumi |
| 6,595,912 B1 | 7/2003 | Lau et al. |
| 6,602,184 B1 | 8/2003 | Lau et al. |
| 6,612,978 B1 | 9/2003 | Lau et al. |
| 6,612,979 B1 | 9/2003 | Lau et al. |
| 6,633,780 B1 | 10/2003 | Berger |
| 6,645,139 B1 | 11/2003 | Haindl |
| 6,647,292 B1 * | 11/2003 | Bardy et al. .................. 607/5 |
| 6,663,558 B1 | 12/2003 | Lau et al. |
| 6,673,009 B1 | 1/2004 | Vanden Hoek et al. |
| 6,682,474 B1 | 1/2004 | Lau et al. |
| 6,682,475 B1 | 1/2004 | Cox et al. |
| 6,682,476 B1 | 1/2004 | Alferness et al. |
| 6,685,620 B1 | 2/2004 | Gifford, III et al. |
| 6,685,627 B1 | 2/2004 | Jayaraman |
| 6,689,048 B1 | 2/2004 | Vanden Hoek et al. |
| 6,695,769 B1 | 2/2004 | French et al. |
| 6,699,259 B1 | 3/2004 | Fogarty et al. |
| 6,701,929 B1 | 3/2004 | Hussein |
| 6,702,732 B1 | 3/2004 | Lau et al. |
| 6,723,041 B1 | 4/2004 | Lau et al. |
| 6,730,016 B1 | 5/2004 | Cox et al. |
| 6,755,779 B1 | 6/2004 | Vanden Hoek et al. |
| 6,759,431 B1 | 7/2004 | Hunter et al. |
| 6,818,018 B1 | 11/2004 | Sawhney |
| 6,833,408 B1 | 12/2004 | Sehl et al. |
| 6,881,185 B1 | 4/2005 | Vanden Hoek et al. |
| 6,887,192 B1 | 5/2005 | Whayne et al. |
| 6,893,392 B1 | 5/2005 | Alferness |
| 6,896,652 B1 | 5/2005 | Alferness et al. |
| 6,902,522 B1 | 6/2005 | Walsh et al. |
| 6,902,524 B1 | 6/2005 | Alferness et al. |
| 6,908,426 B1 | 6/2005 | Shapland et al. |
| 2001/0293134 | 10/2001 | Alferness et al. |
| 2001/0047122 A1 | 11/2001 | Vanden Hoek et al. |
| 2002/0007216 A1 | 1/2002 | Melvin |
| 2002/0019580 A1 * | 2/2002 | Lau et al. .................. 600/37 |
| 2002/0022880 A1 | 2/2002 | Melvin |
| 2002/0028981 A1 * | 3/2002 | Lau et al. .................. 600/37 |
| 2002/0068849 A1 | 6/2002 | Schweich, Jr. et al. |
| 2002/0077524 A1 | 6/2002 | Schweich, Jr. et al. |
| 2002/0082647 A1 | 6/2002 | Alferness et al. |
| 2002/0091296 A1 | 7/2002 | Alferness |
| 2002/0103511 A1 | 8/2002 | Alferness et al. |
| 2002/0151950 A1 | 10/2002 | Okuzumi |
| 2003/0060674 A1 | 3/2003 | Gifford, III et al. |
| 2003/0060677 A1 | 3/2003 | French et al. |
| 2003/0060895 A1 | 3/2003 | French et al. |
| 2003/0199733 A1 | 10/2003 | Shapland et al. |
| 2003/0199955 A1 | 10/2003 | Struble et al. |
| 2003/0229265 A1 | 12/2003 | Girard et al. |
| 2004/0133069 A1 | 7/2004 | Shapland et al. |
| 2004/0171907 A1 | 9/2004 | Alferness et al. |
| 2004/0171908 A1 | 9/2004 | Alferness et al. |
| 2005/0059854 A1 | 3/2005 | Hoek et al. |
| 2005/0085688 A1 | 4/2005 | Girard et al. |

FOREIGN PATENT DOCUMENTS

| | | |
|---|---|---|
| DE | 38 31 540 C2 | 6/1993 |
| DE | 295 17 393 U1 | 3/1996 |
| EP | 0 370 931 A1 | 5/1990 |
| EP | 0 280 564 B1 | 6/1993 |
| EP | 0 583 012 B1 | 7/1996 |
| EP | 0 791 330 A3 | 8/1997 |
| EP | 0 919 193 A1 | 6/1999 |
| FR | 2 527 435 | 12/1983 |
| FR | 2 645 739 | 10/1990 |
| GB | 2 115 287 A | 9/1983 |
| GB | 2 209 678 A | 5/1989 |
| JP | 60-203250 | 10/1985 |
| JP | 3831 540 A1 | 4/1989 |
| JP | 1-145066 | 6/1989 |
| JP | 1-271829 | 10/1989 |
| SU | 1009457 | 4/1983 |
| SU | 3316206/28-13 | 4/1983 |
| SU | 1734767 A1 | 5/1992 |
| WO | WO 91/19465 | 12/1991 |
| WO | WO 95/06447 | 3/1995 |
| WO | WO 96/04852 | 2/1996 |
| WO | WO 96/40356 | 12/1996 |
| WO | WO 97/20505 | 6/1997 |
| WO | WO 97/24101 | 7/1997 |
| WO | WO 98/03213 | 1/1998 |
| WO | WO 98/14136 | 4/1998 |
| WO | WO 98/26738 | 6/1998 |
| WO | WO 98/29041 | 7/1998 |
| WO | WO 98/58598 | 12/1998 |
| WO | WO 99/11201 | 3/1999 |
| WO | WO 99/30647 | 6/1999 |
| WO | WO 99/44534 | 9/1999 |
| WO | WO 99/44680 | 9/1999 |
| WO | WO 99/53977 | 10/1999 |
| WO | WO 99/56655 | 11/1999 |
| WO | WO 00/02500 | 1/2000 |
| WO | WO 00/06026 | 2/2000 |
| WO | WO 00/06027 | 2/2000 |
| WO | WO 00/06028 | 2/2000 |
| WO | WO 00/13722 | 3/2000 |
| WO | WO 00/16700 | 3/2000 |
| WO | WO 00/18320 | 4/2000 |
| WO | WO 00/28912 | 5/2000 |
| WO | WO 00/28918 | 5/2000 |
| WO | WO 00/42919 | 7/2000 |
| WO | WO 00/45735 | 8/2000 |
| WO | WO 00/48795 | 8/2000 |
| WO | WO 00/62727 | 10/2000 |
| WO | WO 00/74769 | 12/2000 |
| WO | WO 01/17437 | 3/2001 |
| WO | WO 01/21098 | 3/2001 |
| WO | WO 01/50981 | 7/2001 |
| WO | WO 01/67985 | 9/2001 |
| WO | WO 01/85061 | 11/2001 |
| WO | WO 01/91667 | 12/2001 |
| WO | WO 01/95830 | 12/2001 |
| WO | WO 01/95831 | 12/2001 |
| WO | WO 01/95832 | 12/2001 |
| WO | WO 02/13726 | 2/2002 |
| WO | WO 02/19917 | 3/2002 |
| WO | WO 03/026483 | 4/2003 |
| WO | WO 03/026484 | 4/2003 |
| WO | WO 03/026485 | 4/2003 |

OTHER PUBLICATIONS

Anstadt, George L., et al., A New Instrument for Prolonged Mechanical Cardiac Massage, *Abstracts of the 38th Scientific Sessions*, Supplement II to Circulation, vols. 31 and 32, pp. 375-384, Oct. 1965.

Lev, Maurice, M.D., et al., Single (Primitive) Ventricle, *Circulation*, vol. 39, pp. 577-591.

Paling, D.F., *Warp Knitting Technology*, 1970.

Edie, Richard N., M.D., et al., Surgical Repair of Single Ventricle, *The Journal of Thoracic and Cardiovascular Surgery*, vol. 66, No. 3, pp. 350-360, Sep. 1972.

McGoon, Dwight C., M.D., et al., Correction of the Univentricular Heart Having Two Atriovantricular Valves. *The Journal of Thoracic and Cardiovascular Surgery*, vol. 74, No. 2, pp. 218-226, Aug. 1977.

Doty, Donald B., et al., Septation of the Univentricular Heart: Transatrial Approach, *The Journal of Thoracic and Cardiovascular Surgery*, vol. 78, No. 3, pp. 424-430, Sep. 1979.

Schetky, L. McDonald, Shup- Memory Alloy's, *Scientific American*, vol. 241, No. 5, pp. 74-82, Nov. 1979.

Melton, K.N., et al., Alloys With Two-Shape Memory Effect, *Mechanical Engineering*, pp. 42-43, Mar. 1980.

Feldt, Robert H., M.D., et al., Current Status of the Septation Procedure for Univentricular Heart, *The Journal of Thoracic and Cardiovascular Surgery*, vol. 82, No. 1, pp. 93-97, Jul. 1981.

Carpentier, A., et al., Myocardial Substitution With Stimulated Skeletal Muscle: First Successful Clinical Case, *The Lancet*, Jun. 1, 1985.

Anstadt, George L. et al., Direct Mechanical Ventricular Actuation: A Review, *Resuscitation*, pp. 7-23, 1991.

Anstadt, Mark P., M.D., et al., Pulsatile Reperfusion After Cardiac Arrest Improves Neurologic Outcome, *American Surgery*, vol. 214, No. 4, pp. 478-490, Oct. 1991.

Schumacker, Harris B., Jr., Chapter 21: Cardiac Aneurysms, *The Evolution of Cardiac Surgery*, pp. 159-165, 1992.

Savage, Edward B., M.D., et al., Repair of Left Ventricular Aneurysm, *The Journal of Thoracic and Cardiovascular Surgery*, vol. 104, No. 3, pp. 752-762, Sep. 1992.

Carpentier, Alain, M.D., Ph.D., et al., Dynamic Cardiomyoplasty at Seven Years, *The Journal of Thoracic and Cardiovascular Surgery*, vol. 106, No. 1, pp. 42-54, Jul. 1993.

Capouya, Eli R., M.D., et al., Girdling Effect of Nonstimulated Cardiomyoplasty on Left Ventricular Function, *Annals of Thoracic Surgeons*, vol. 56, pp. 867-71, 1993.

Chekanov, Valeri, M.D., Ph.D., Nonstimulated Cardiomyoplasty Wrap Attenuated the Degree of Left Ventricular Enlargement, *Annals of Thoracic Surgeons*, vol. 57, pp. 1684-1690, 1997.

Chiu, Ray C.-J, Using Skeletal Muscle for Cardiac Assistance, *Scientific American*, pp. 68-77, Nov./Dec. 1994.

Kass, David A., M.D., et al., Reverse Remodeling From Cardiomyoplasty in Human Heart Failure: External Constraint Versus Active Assist, *Circulation*, vol. 91, No. 9, pp. 2314-2318, May 1, 1995.

Vaynblat, Mikhail, M.D., et al., Cardiac Binding in Experimental Heart Failure, Annals of Thoracic Surgery (Abstract), Supplement to *Circulation*, vol. 92, Suppl. 1, 1995.

Levin, Howard R., M.D., et al., Reversal of Chronic Ventricular Dilation in Patients With End-Stage Cardiomyopathy by Prolonged Mechanical Unloading, *Circulation*, vol. 91, No. 11, pp. 2717-2720, 1995.

Chaudhry, Pervaiz A., M.D., et al., Acute Ventricular Reduction with Acorn's Cardiac Support Device Prevents Progressive Left Ventricular Dysfunction and Remodeling in Dogs With Advanced Heart Failure, *Cardiothoracic Surgery*, pp. 146-148, 1996.

Oh, Joong Hwan, M.D., et al., Mechanisms of Dynamic Cardiomyoplasty: Current Concepts, *Journal of Cardiac Surgery*, vol. 11, pp. 194-199, 1996.

Badhwar, Vinay, Power Generation From Four Skeletal Muscle Configurations Design Implications for a Muscle Powered Cardiac Assist Device, *ASAIO Journal*, vol. 43, pp. M651-M657, 1997.

Westaby, Stephen, et al., *Landmarks in Cardiac Surgery*, pp. 198-199, 1997.

Cox, James L., Left Ventricular Aneurysms: Pathophysiologic Observations and Standard Resection, *Seminars in Thoracic and Cardiovascular Surgery*, vol. 9, No. 2, pp. 113-122, Apr. 1997.

Coletta, C., et al., Prognostic Value of Left Ventricular Volume Response During Dobutamine Stress Echocardiography, *European Heart Journal*, vol. 18, pp. 1599-1603, Oct. 1997.

Capomolla, Soccorso, M.D., et al., Dobutamine and Nitroprusside Infusion in Patients With Severe Congestive Heart Failure: Hemodynamic Improvement by Discordant Effects on Mitral Regurgitation, Left Atrial Function, and Ventricular Function, *American Heart Journal*, 1089-1098, Dec. 1997.

Oh, Joong Hwan, The Effects of Prosthetic Cardiac Binding and Adynamic Cardiomyoplasty in a Model of Dilated Cardiomyopathy, *The Journal of Thoracic and Cardiovascular Surgery*, vol. 116, No. 1, pp. 148-153, 1998.

Cohn, Jay N., M.D., Preventing Congestive Heart Failure, *American Family Physician*, 6 pages, Apr. 15, 1998.

Cohn, Jay N., M.D., Structural Basis for Heart Failure: Ventricular Remodeling and Its Pharmacological Inhibition, *Circulation*, vol. 91, No. 10, pp. 2504-2507, May 15, 1995.

Gaudron, Peter, M.D., et al., Progressive Left Ventricular Remodeling After Myocardial Infarction, *Circulation*, vol. 87, pp. 755-763, Mar. 1993.

Pfeiffer, Marc A., M.D., et al., Ventricular Remodeling After Myocardial Infarction: Experimental Observations and Clinical Implications, *Circulation*, vol 81, No. 4, pp. 1161-1172, Apr. 1990.

Guasp, Francisco Torrent, Una protesis contentiva para el tratamiento de le microcardiopatia dilatads, *Revista Española de Cardiologia*, vol. 51, No. 7, Jul. 1998.

Power, J.M., et al., Passive Ventricular Constraint Antends the Course of Heart Failure: A Study in an Ovine Model of Dilated Cardiomypathy, *Cardiovascular Research*, vol. 44, pp. 549-555, 1999.

Frazier, O.H., M.D., et al., Left Ventricular Assist System as a Bridge to Myocardial Recovery, *Annals of Thoracic Surgery*, vol. 68, pp. 734-741, 1999.

Melvin, David B., Ventricular Radium Reduction Without Resection: A Computational Analysis, *ASAIO Journal*, pp. 160-165, 1999.

*ABSTRACTS—Heart Failure*, JACC Feb. 1999.

Raman, Jai S., Fracs, et al., Ventricular Containment as an Adjunctive Procedure in Ischemic Cardiomyopathy: Early Results, *Annals of Thoracic Surgery*, vol. 70, pp. 1124-1126, Jan. 2000.

McCarthy, Patrick M., et al., *Device Based Left Ventricular Shape Change Immediately Reduces Left Ventricular Volume and Increases Ejection Fraction in a Pacing Induced Cardiomyopathy Model in Dogs*, JACC, Feb. 2000.

Chaudhry, Pervaiz A., M.D., et al., Passive Epicardial Containment Prevents Ventricular Remodeling in Heart Failure, *Annals of Thoracic Surgeons*, vol. 70, pp. 1275-1280, 2000.

Acorn Cardiovascular, Inc., *CSD Specifications Acorn Cardiac Support Device*, 2000.

Heart "jacket" could help stop heart failure progression, *Clinicia*, No. 916, Jul. 2000.

Acorn Cardiovascular, Inc., *CorCap™ Cardiac Support Device Pamphlet*, Jun. 2001.

*Medtronic's InSync Cardiac Resynchronization Therapy Device Approved by FDA*, (Press Release) Aug. 28, 2001.

Oz, Mehmet C., M.D., Passive Ventricular Constraint for the Treatment of Congestive Heart Failure, *Annals of Thoracic Surgery*, vol. 71, 5185-5187, 2001.

Abstract Supplement, *European Heart Journal*, vol. 22, Sep. 2001.

Gorman, J., Self-Sutures: New Material Knots Up On Its Own, *Science News*, vol. 161, p. 262, Apr. 27, 2002.

Teckell-Taylor, Leah A., et al., *Passive Ventricular Restraint With Nitinol Mesh Attenuates Remodeling Following Acute Myocardial Infarction*, Abstract, American College of Cardiology (Undated).

Mann, Douglas L., M.D., *Basic Mechanisms of Remodeling and Reverse Remodeling*, presented at 6th Annual Scientific Meeting of the Heart Failure Society of America, Sep. 24, 2002.

Bocchi, Edimar a., M.D., Arrhythmias and Sudden Death After Dynamic Cardiomyoplasty, *Circulation*, vol. 90, No. 5, Part 2, pp. II-107 thru II-111, Nov. 1994.

Chachques, Juan C., M.D., Study of Muscular and Ventricular Function in Dynamic Cardiomyoplasty: A Ten-Year Follow-Up, *The Journal of Heart and Lung Transplantation*, vol. 16, No. 8, pp. 854-868, Aug. 1997.

Dullum, Mercedes K.C., M.D., et al., *Less Invasive Surgical Management of Heart Failure by Cardiac Support Device Implantation on the Beating Heart*, The Heart Surgery Forum, #2001-1818, pp. 361-363, Jan. 4-7, 2001.

Macris, Michael P. M.D., et al., *Minimally Invasive Access of the Normal Preicardium: Initial Clinical Experience with a Novel Device*, Clinical Cardiology, vol. 22 (Suppl. I), pp. I-36 thru I-39, 1999.

Thakur, Ranjan K., M.D., et al., *Latissimus Dorsi Dynamic Cardiomyoplasty: Role of Combined ICD Implantation*, Journal of Cardiac Surgery, vol. 10, pp. 295-297, 1995.

U.S. Appl. No. 09/952,145, filed Sep. 10, 2001.
U.S. Appl. No. 10/314,696, filed Dec. 9, 2002.
U.S. Appl. No. 60/486,062, filed Jul. 10, 2003.
U.S. Appl. No. 10/698,237, filed Oct. 31, 2003.
U.S. Appl. No. 10/704,376, filed Nov. 7, 2003.
U.S. Appl. No. 10/715,150, filed Nov. 17, 2003.
U.S. Appl. No. 60/535,888, filed Jan. 12, 2004.

Bencini, Adriano, M.D., *The "Pneumomassage" of the Heart*, Surgery, vol. 39, No. 3, Mar. 1956.

Anstadt, George L., et al., *A New Instrument for Prolonged Mechanical Cardiac Massage*, Abstracts of the 38$^{th}$ Scientific Sessions, Supplement II to Circulation, vol. 31 and 32, pp. 375-384, Oct. 1965.

Lev, Maurice, M.D., et al., *Single (Primitive) Ventricle*, Circulation, vol. 39, pp. 577-591.

Paling, D.F., *Warp Knitting Technology*, 1970.

Edie, Richard N., M.D., et al., *Surgical Repair of Single Ventricle*, The Journal of Thoracic and Cardiovascular Surgery, vol. 66, No. 3, pp. 350-360, Sep. 1972.

McGoon, Dwight C., M.D., et al., *Correction of the Univentricular Heart Having Two Atriovantricular Valves*, The Journal of Thoracic and Cardiovascular Surgery, vol. 74, No. 2, pp. 218-226, Aug. 1977.

Doty, Donald B., et al., *Septation of the Univentricular Heart: Transatrial Approach*, The Journal of Thoracic and Cardiovascular Surgery, vol. 78, No. 3, pp. 424-430, Sep. 1979.

Schetky, L. McDonald, *Shap- Memory Alloys*, Scientific American, vol. 241, No. 5, pp. 74-82, Nov. 1979.

Melton, K.N., et al., *Alloys With Two-Shape Memory Effect*, Mechanical Engineering, pp. 42-43, Mar. 1980.

Feldt, Robert H., M.D., et al., *Current Status of the Septation Procedure for Univentricular Heart*, The Journal of Thoracic and Cardiovascular Surgery, vol. 82, No. 1, pp. 93-97, Jul. 1981.

Carpentier, A., et al., *Myocardial Substitution With Stimulated Skeletal Muscle: First Successful Clinical Case*, The Lancet, Jun. 1, 1985.

Anstadt, George L. et al., *Direct Mechanical Ventricular Actuation: A Review*, Resuscitation, pp. 7-23, 1991.

Anstadt, Mark P., M.D., et al., *Pulsatile Reperfusion After Cardiac Arrest Improves Neurologic Outcome*, American Surgery, vol. 214, No. 4, pp. 478-490, Oct. 1991.

Schumacker, Harris B., Jr., *Chapter 21: Cardiac Aneurysms*, The Evolution of Cardiac Surgery, pp. 159-165, 1992.

Savage, Edward B., M.D., et al., *Repair of Left Ventricular Aneurysm*, The Journal of Thoracic and Cardiovascular Surgery, vol. 104, No. 3, pp. 752-762, Sep. 1992.

Carpentier, Alain, M.D., Ph.D., et al., *Dynamic Cardiomyoplasty at Seven Years*, The Journal of Thoracic and Cardiovascular Surgery, vol. 106, No. 1, pp. 42-54, Jul. 1993.

Capouya, Eli R., M.D., et al., *Girdling Effect of Nonstimulated Cardiomyoplasty on Left Ventricular Function*, Annals of Thoracic Surgeons, vol. 56, pp. 867-71, 1993.

Chekanov, Valeri, M.D., Ph.D., *Nonstimulated Cardiomyoplasty Wrap Attenuated the Degree of Left Ventricular Enlargement*, Annals of Thoracic Surgeons, vol. 57, pp. 1684-1690, 1997.

Chiu, Ray C.-J, *Using Skeletal Muscle for Cardiac Assistance*, Scientific American, pp. 68-77, Nov./Dec. 1994.

Kass, David A., M.D., et al., *Reverse Remodeling From Cardiomyoplasty in Human Heart Failure: External Constraint Versus Active Assist*, Circulation, vol. 91, No. 9, pp. 2314-2318, May 1, 1995.

Vaynblat, Mikhail, M.D., et al., *Cardiac Binding in Experimental Heart Failure*, Annals of Thoracic Surgery (Abstract) Supplement to Circulation , vol. 92, Suppl. 1, 1995.

Levin, Howard R., M.D., et al., *Reversal of Chronic Ventricular Dilation in Patients With End-Stage Cardiomyopathy by Prolonged Mechanical Unloading*, Circulation, vol. 91, No. 11, pp. 2717-2720, 1995.

Chaudhry, Pervaiz A., M.D., et al., *Acute Ventricular Reduction with Acorn's Cardiac Support Device Prevents Progressive Left Ventricular Dysfunction and Remodeling in Dogs With Advanced Heart Failure*, Cardiothoracic Surgery, pp. 146-148, 1996.

Oh, Joong Hwan, M.D., et al., *Mechanisms of Dynamic Cardiomyoplasty: Current Concepts*, Journal of Cardiac Surgery, vol. 11, pp. 194-199, 1996.

Badhwar, Vinay, *Power Generation From Four Skeletal Muscle Configurations Design Implications for a Muscle Powered Cardiac Assist Device*, ASAIO Journal, vol. 43, pp. M651-M657, 1997.

Westaby, Stephen, et al., *Landmarks in Cardiac Surgery*, pp. 198-199, 1997.

Cox, James L., *Left Ventricular Aneurysms: Pathophysiologic Observations and Standard Resection*, Seminars in Thoracic and Cardiovascular Surgery, vol. 9, No. 2, pp. 113-122, Apr. 1997.

Coletta, C., et al., *Prognostic Value of Left Ventricular Volume Response During Dobutamine Stress Echocardiography*, European Heart Journal, vol. 18, pp. 1599-1603, Oct. 1997.

Capomolla, Soccorso, M.D., et al., *Dobutamine and Nitroprusside Infusion in Patients With Severe Congestive Heart Failure: Hemodynamic Improvement by Discordant Effects on Mitral Regurgitation, Left Atrial Function, and Ventricular Function*, American Heart Journal, 1089-1098, Dec. 1997.

Oh, Joong Hwan, *The Effects of Prosthetic Cardiac Binding and Adynamic Cardiomyoplasty in a Model of Dilated Cardiomyopathy*, The Journal of Thoracic and Cardiovascular Surgery, vol. 116, No. 1, pp. 148-153, 1998.

Cohn, Jay N., M.D., *Preventing Congestive Heart Failure*, American Family Physician, 6 pages, Apr. 15, 1998.

Cohn, Jay N., M.D., *Structural Basis for Heart Failure: Ventricular Remodeling and Its Pharmacological Inhibition*, Circulation, vol. 91, No. 10, pp. 2504-2507, May 15, 1995.

Gaudron, Peter, M.D., et al., *Progressive Left Ventricular Dysfunction and Remodeling After Myocardial Infarction*, Circulation, vol. 87, pp. 755-763, Mar. 1993.

Pfeffer, Marc A., M.D., et al., *Ventricular Remodeling After Myocardial Infarction: Experimental Observations and Clinical Implications*, Circulation, vol. 81, No. 4, pp. 1161-1172, Apr. 1990.

Guasp, Francisco Torrent, *Una protesis contentiva para el tratamiento de le microcardiopatia dilatads*, Revista Española de Cardiologia, vol. 51, No. 7, Jul. 1998.

Power, J.M., et al., *Passive Ventricular Constraint Amends the Course of Heart Failure: A Study in an Ovine Model of Dilated Cardiomyopathy*, Cardiovascular Research, vol. 44, pp. 549-555, 1999.

Frazier, O.H., M.D., et al., *Left Ventricular Assist System as a Bridge to Myocardial Recovery*, Annals of Thoracic Surgery, vol. 68, pp. 734-741, 1999.

Melvin, David B., *Ventricular Radius Reduction Without Resection: A Computational Analysis*, ASAIO Journal, pp. 160-165, 1999.

*ABSTRACTS—Heart Failure*, JACC Feb. 1999.

Raman, Jai S., Fracs, et al., *Ventricular Containment as an Adjunctive Procedure in Ischemic Cardiomyopathy: Early Results*, Annals of Thoracic Surgery, vol. 70, pp. 1124-1126, Jan. 2000.

McCarthy, Patrick M., et al., *Device Based Left Ventricular Shape Change Immediately Reduces Left Ventricular Volume and Increases Ejection Fraction in a Pacing Induced Cardiomyopathy Model in Dogs*, JACC, Feb. 2000.

Chaudhry, Pervaiz A., M.D., et al., *Passive Epicardial Containment Prevents Ventricular Remodeling in Heart Failure*, Annals of Thoracic Surgeons, vol. 70, pp. 1275-1280, 2000.

Acorn Cardiovascular, Inc., *CSD Specifications Acorn Cardiac Support Device*, 2000.

*Heart "jacket" could help stop heart failure progression*, Clinicia, No. 916, Jul. 2000.

Acorn Cardiovascular, Inc., *CorCap™ Cardiac Support Device* Phamphlet, Jun. 2001.

*Medtronic's InSync Cardiac Resynchronization Therapy Device Approved by FDA*, (Press Release) Aug. 28, 2001.

Oz, Mehmet C., M.D., Passive Ventricular Constraint for the Treatment of Congestive Heart Failure, *Annals of Thoracic Surgery*, vol. 71, pp. 5185-5187, 2001.

Abstract Supplement, *European Heart Journal*, vol. 22, Sep. 2001.

Gorman, J., Self-Sutures: New Material Knots Up On Its Own, *Science News*, Vol. 161, p. 262, Apr. 27, 2002.

Teckell-Taylor, Leah A., et al., *Passive Ventricular Restraint With Nitinol Mesh Attenuates Remodeling Following Acute Myocardial Infarction*, Abstract, American College of Cardiology, Undated.

Mann, Douglas L., M.D., *Basic Mechanisms of Remodeling and Reverse Remodeling*, presented at 6th Annual Scientific Meeting of the Heart Failure Society of America, Sep. 24, 2002.

Bocchi, Edimar a., M.D., Arrhythmias and Sudden Death After Dynamic Cardiomyoplasty, *Circulation*, vol. 90, No. 5, Part 2, pp. II-107 thru II-111, Nov. 1994.

Chachques, Juan C., M.D., Study of Muscular and Ventricular Function in Dynamic Cardiomyoplasty: A Ten-Year Follow-Up, *The Journal of Heart and Lung Transplantation*, vol. 16, No. 8, pp. 854-868, Aug. 1997.

Dullum, Mercedes K.C., M.D., et al., *Less Invasive Surgical Management of Heart Failure by Cardiac Support Device Implantation on the Beating Heart*, The Heart Surgery Forum, #2001-1818, pp. 361-363, Jan. 4-7, 2001.

Macris, Michael P. M.D., et al., Minimally Invasive Access of the Normal Preicardium: Initial Clinical Experience with a Novel Device, *Clinical Cardiology*, vol. 22 (Suppl. I), pp. 1-36 thru 1-39, 1999.

Thakur, Ranjan K., M.D., et al., Latissimus Dorsi Dynamic Cardiomyoplasty: Role of Combined ICD Implantation, *Journal of Cardiac Surgery*, vol. 10, pp. 295-297, 1995.

Wharton, J. Marcus, et al., Electrophysiological Effects of Monophasic and Biphasic Stimuli in Normal and Infarcted Dogs, *PACE*, vol. 13, pp. 1158-1172, Sep. 1990.

Shabetai, Ralph, The Role of the Pericardium in the Pathophysiology of Heart Failure, *Congestive Heart Failure*, Second Edition, Chapter 9, pp. 157-187, 2000.

Cohn, Jay N., M.D., The Management of Chronic Heart Failure, *The New England Journal of Medicine*, vol. 335, No. 7, pp. 490-498, Aug. 15, 1996.

Zhou, Xiaohong, et al., Epicardial Mapping of Ventricular Defibrillation With Monophasic and Biphasic Shocks in Dogs, *Circulation Research*, vol. 72, No. 1, pp. 145-160, Jan. 1993.

Shorofsky, Stephen R., et al., Comparison of Step-Down and Binary Search Algorithms for Determination of Defibrillation Threshold in Humans, *PACE*, vol. 27, pp. 218-220, Feb. 2004.

Gold, Michael R., M.D., et al., Comparison of Single- and Dual-Coil Active Pectoral Defibrillation Lead Systems, *Journal of the American College of Cardiology*, vol. 31, No. 6, pp. 1391-1394, May 1998.

Rinaldi, C. Aldo, A Randomized Prospective Study of Single Coil Versus Dual Coil Defibrillation in Patients With Ventricular Arrhythmias Undergoing Implantable Cardioverter Defibrillator Therapy, *PACE*, vol. 26, pp. 1684 1690, Aug. 2003.

Schwartzman, David, M.D., et al., Serial Defibrillation Lead Impedance in Patients with Epicardial and Nonthoracotomy Lead Systems, *Journal of Cardiovascular Electrophysiology*, vol. 7, No. 8, pp. 697-703, Aug. 1996.

Sandstedt, Bengt, et al., Bidirectioinal Defibrillation Using Implantable Defibrillators: A Prospective Randomized Comparison Between Pectoral and Abdominal Active Generators, *PACE*, vol. 24, Part 1, pp. 1343-1353, Sep. 2001.

Schulte, B., et al., Dual-Coil vs. Single-Coil Active Pectoral Implantable Defibrillator Lead Systems: Defibrillation Lead Requirements and Probability of Defibrillation Success at Multiples of the Defibrillation Energy Requirements, *Europace*, vol. 3, pp. 177-180, Jul. 2001.

U.S. Appl. No. 09/952,145 filed Sep. 10, 2001 published on Feb. 14, 2003 as Pub. No. 02-0019580-A1; Inventors: Lau et al.

U.S. Appl. No. 10/314,696 filed Dec. 9, 2002 published on Apr. 3, 2003 as Pub. No. 03-0065248-A1; Inventors: Lau et al.

U.S. Appl. No. 60/486,062 filed Jul. 10, 2003; Inventors: Hong et al.

U.S. Appl. No. 10/698,237 filed Oct. 31, 2003 published on Jul. 29, 2004 as Pub. No. 04-0147805-A1; Inventor: Lau.

U.S. Appl. No. 10/704,376 filed Nov. 7, 2003; Inventor: Lau.

U.S. Appl. No. 10/715,150 filed Nov. 17, 2003 published on Mar. 10, 2005 as Pub. No. 05-0055032; Inventor: Lau.

U.S. Appl. No. 60/535,888 filed Jan. 12, 2004; Inventors: Fishler et al.

* cited by examiner

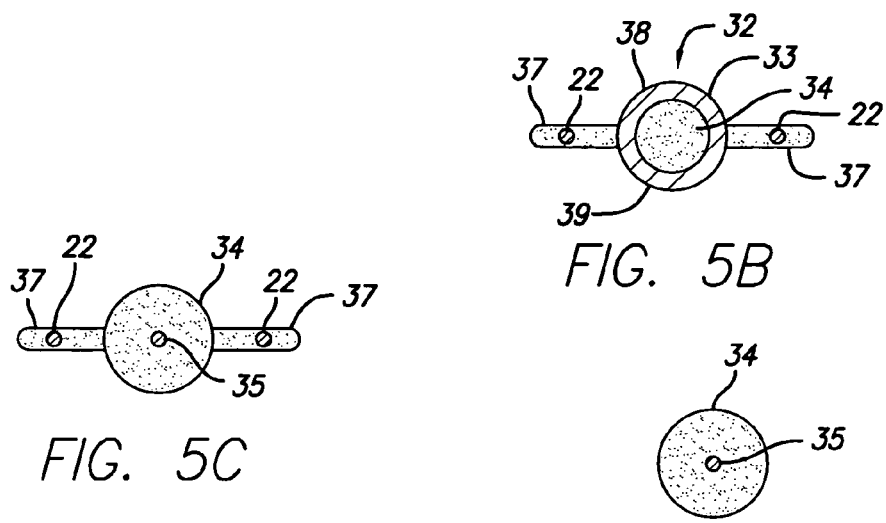
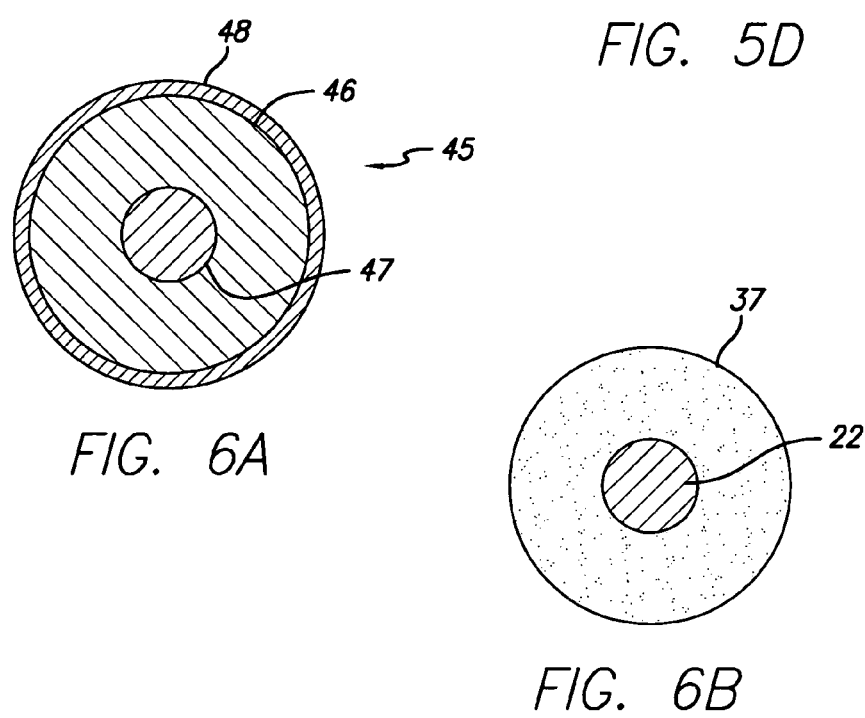
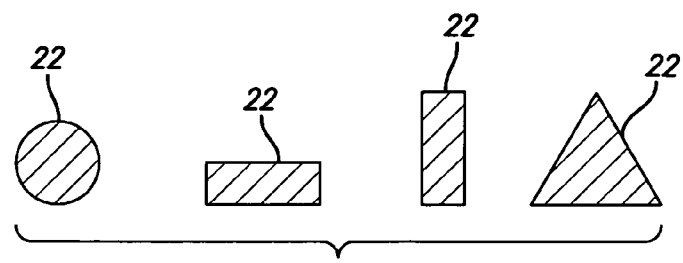

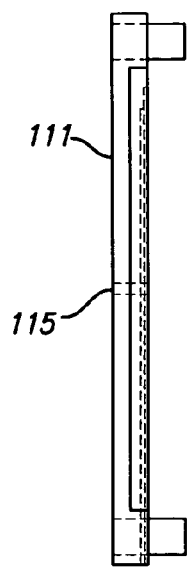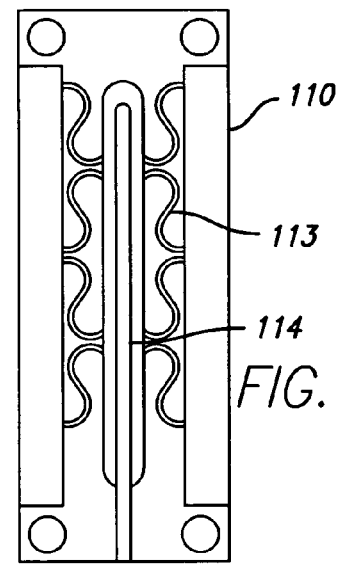
FIG. 18A
FIG. 18B
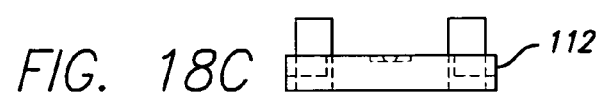
FIG. 18C
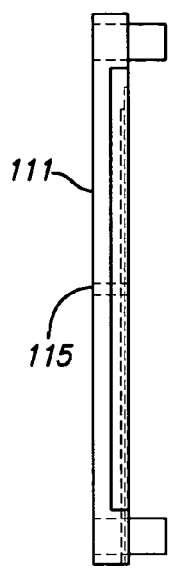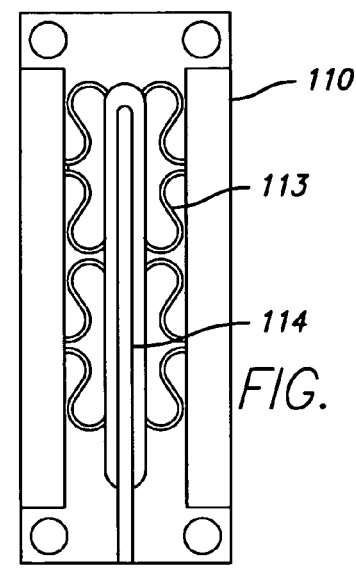
FIG. 19A
FIG. 19B
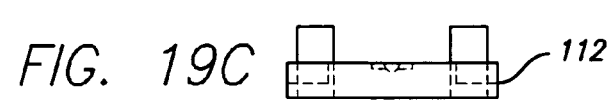
FIG. 19C

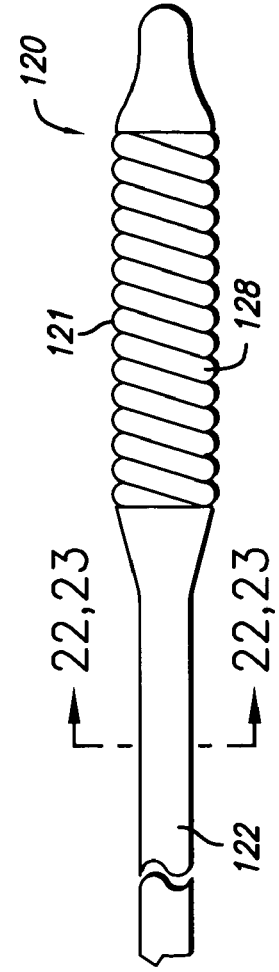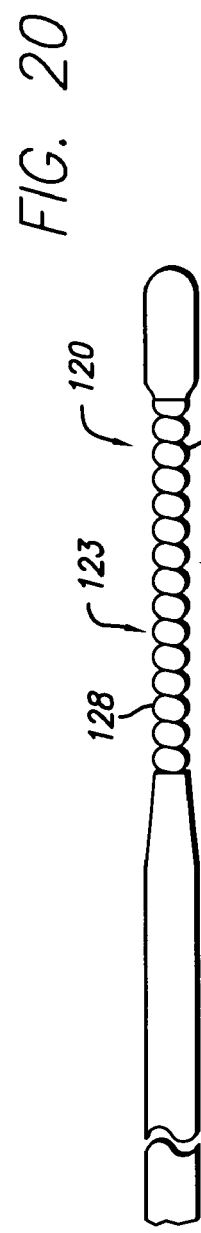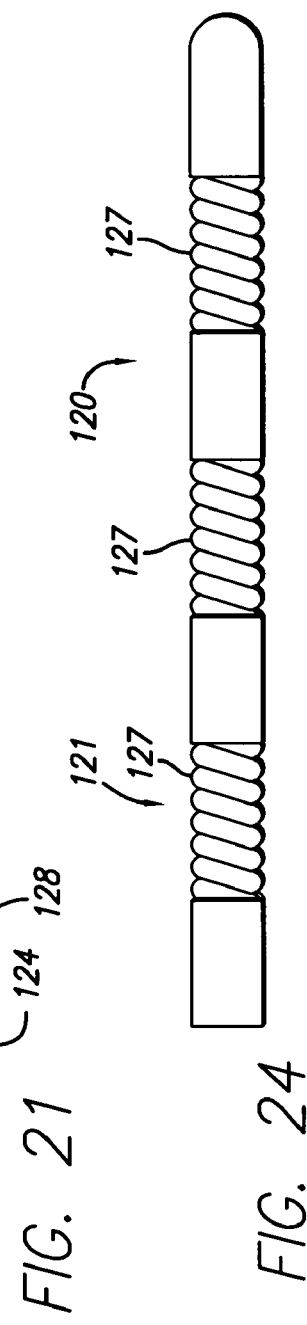
FIG. 22
FIG. 23
FIG. 20
FIG. 21
FIG. 24

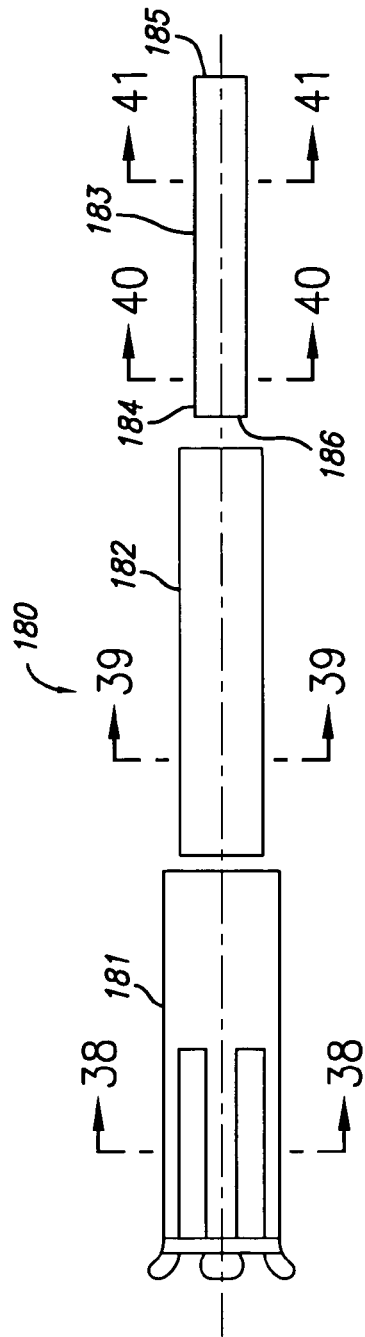
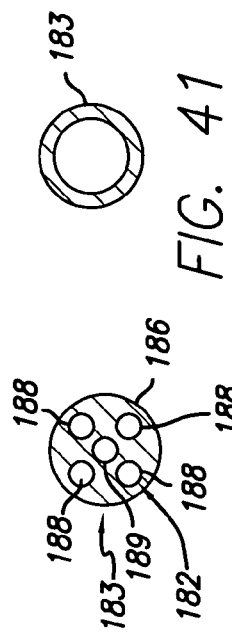
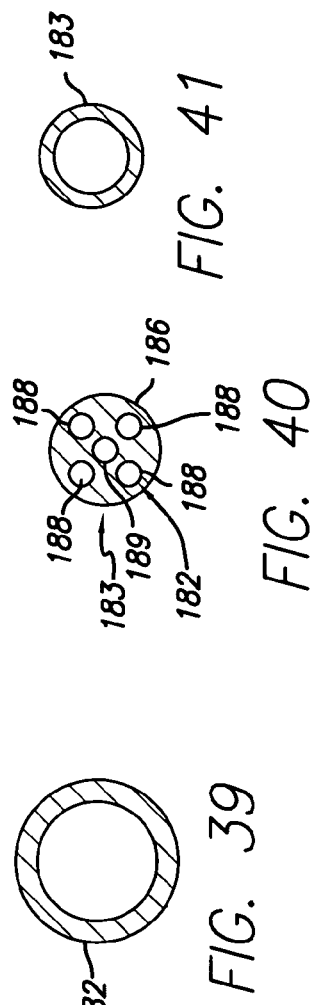
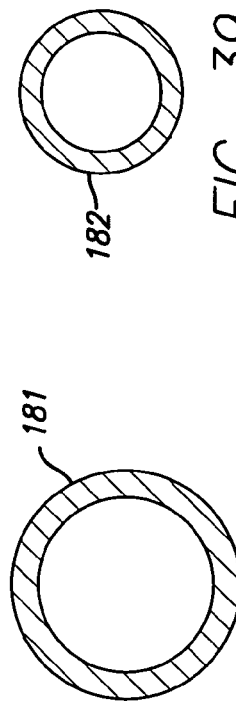
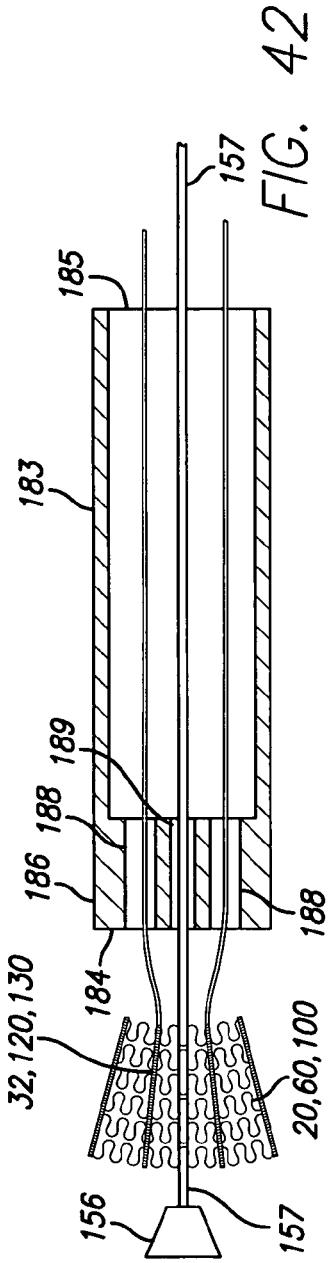

CARDIAC HARNESS FOR TREATING HEART DISEASE

CROSS-REFERENCE TO RELATED APPLICATION

This application is a continuation-in-part of co-pending application Ser. No. 10/704,376 filed on Nov. 7, 2003, which is herein incorporated by reference.

BACKGROUND OF THE INVENTION

The present invention relates to a device for treating heart failure. More specifically, the invention relates to a cardiac harness configured to be fit around at least a portion of a patient's heart. The cardiac harness includes electrodes attached to a power source for use in defibrillation or pacing.

Congestive heart failure ("CHF") is characterized by the failure of the heart to pump blood at sufficient flow rates to meet the metabolic demand of tissues, especially the demand for oxygen. One characteristic of CHF is remodeling of at least portions of a patient's heart. Remodeling involves physical change to the size, shape and thickness of the heart wall. For example, a damaged left ventricle may have some localized thinning and stretching of a portion of the myocardium. The thinned portion of the myocardium often is functionally impaired, and other portions of the myocardium attempt to compensate. As a result, the other portions of the myocardium may expand so that the stroke volume of the ventricle is maintained notwithstanding the impaired zone of the myocardium. Such expansion may cause the left ventricle to assume a somewhat spherical shape.

Cardiac remodeling often subjects the heart wall to increased wall tension or stress, which further impairs the heart's functional performance. Often, the heart wall will dilate further in order to compensate for the impairment caused by such increased stress. Thus, a cycle can result, in which dilation leads to further dilation and greater functional impairment.

Historically, congestive heart failure has been managed with a variety of drugs. Devices have also been used to improve cardiac output. For example, left ventricular assist pumps help the heart to pump blood. Multi-chamber pacing has also been employed to optimally synchronize the beating of the heart chambers to improve cardiac output. Various skeletal muscles, such as the latissimus dorsi, have been used to assist ventricular pumping. Researchers and cardiac surgeons have also experimented with prosthetic "girdles" disposed around the heart. One such design is a prosthetic "sock" or "jacket" that is wrapped around the heart.

Patients suffering from congestive heart failure often are at risk to additional cardiac failures, including cardiac arrhythmias. When such arrhythmias occur, the heart must be shocked to return it to a normal cycle, typically by using a defibrillator. Implantable cardioverter/defibrillators (ICD's) are well known in the art and typically have a lead from the ICD connected to an electrode implanted in the right ventricle. Such electrodes are capable of delivering a defibrillating electrical shock from the ICD to the heart.

Other prior art devices have placed the electrodes on the epicardium at various locations, including on or near the epicardial surface of the right and left heart. These devices also are capable of distributing an electrical current from an implantable cardioverter/defibrillator for purposes of treating ventricular defibrillation or hemodynamically stable or unstable ventricular tachyarrhythmias.

Patients suffering from congestive heart failure may also suffer from cardiac failures, including bradycardia and tachycardia. Such disorders typically are treated by both pacemakers and implantable cardioverter/defibrillators. The pacemaker is a device that paces the heart with timed pacing pulses for use in the treatment of bradycardia, where the ventricular rate is too slow, or to treat cardiac rhythms that are too fast, i.e., anti-tachycardia pacing. As used herein, the term "pacemaker" is any cardiac rhythm management device with a pacing functionality, regardless of any other functions it may perform such as the delivery cardioversion or defibrillation shocks to terminate atrial or ventricular fibrillation. Particular forms and uses for pacing/sensing can be found in U.S. Pat. No. 6,574,506 (Kramer et al.) and U.S. Pat. No. 6,223,079 (Bakels et al.); and U.S. Publication No. 2003/0130702 (Kramer et al.) and U.S. Publication No. 2003/0195575 (Kramer et al.), the entire contents of which are incorporated herein by reference thereto.

The present invention solves the problems associated with prior art devices relating to a harness for treating congestive heart failure and placement of electrodes for use in defibrillation, or for use in pacing.

SUMMARY OF THE INVENTION

In accordance with the present invention, a cardiac harness is configured to fit at least a portion of a patient's heart and is associated with one or more electrodes capable of providing defibrillation or pacing functions. In one embodiment, rows or strands of undulations are interconnected and associated with coils or defibrillation and/or pacing/sensing leads. In another embodiment, the cardiac harness includes a number of panels separated by coils or electrodes, wherein the panels have rows or strands of undulations interconnected together so that the panels can flex and can expand and retract circumferentially. The panels of the cardiac harness are coated with a dielectric coating to electrically insulate the panels from an electrical shock delivered through the electrodes. Further, the electrodes are at least partially coated with a dielectric material to insulate the electrodes from the cardiac harness. In one embodiment, the strands or rows of undulations are formed from Nitinol and are coated with a dielectric material such as silicone rubber. In this embodiment, the electrodes are at least partially coated with the same dielectric material of silicone rubber. The electrode portion of the leads are not covered by the dielectric material so that as the electrical shock is delivered by the electrodes to the epicardial surface of the heart, the coated panels and the portion of the electrodes that are coated are insulated by the silicone rubber. In other words, the heart received an electrical shock only where the bare metal of the electrodes are in contact with or are adjacent to the epicardial surface of the heart. The dielectric coating also serves to attach the panels to the electrodes.

In another embodiment, the electrodes have a first surface and a second surface, the first surface being in contact with the outer surface of the heart, such as the epicardium, and the second surface faces away from the heart. Both the first surface and the second surface do not have a dielectric coating so that an electrical charge can be delivered to the outer surface of the heart for defibrillating or for pacing. In this embodiment, at least a portion of the electrodes are coated with a dielectric coating, such as silicone rubber, Parylene™ or polyurethane. The dielectric coating serves to insulate the bare metal portions of the electrode from the cardiac harness, and also to provide attachment means for attaching the electrodes to the panels of the cardiac harness.

The number of electrodes and the number of panels forming the cardiac harness is a matter of choice. For example, in one embodiment the cardiac harness can include two panels separated by two electrodes. The electrodes would be positioned 180° apart, or in some other orientation so that the electrodes could be positioned to provide a optimum electrical shock to the epicardial surface of the heart, preferably adjacent the right ventricle or the left ventricle. In another embodiment, the electrodes can be positioned 180° apart so that the electrical shock carries through the myocardium adjacent the right ventricle thereby providing an optimal electrical shock for defibrillation or periodic shocks for pacing. In another embodiment, three leads are associated with the cardiac harness so that there are three panels separated by the three electrodes.

In yet another embodiment, four panels on the cardiac harness are separated by four electrodes. In this embodiment, two electrodes are positioned adjacent the left ventricle on or near the epicardial surface of the heart while the other two electrodes are positioned adjacent the right ventricle on or near the epicardial surface of the heart. As an electrical shock is delivered, it passes through the myocardium between the two sets of electrodes to shock the entire ventricles.

In another embodiment, there are more than four panels and more than four electrodes forming the cardiac harness. Placement of the electrodes and the panels is a matter of choice. Further, one or more electrodes may be deactivated.

In another embodiment, the cardiac harness includes multiple electrodes separating multiple panels. The embodiment also includes one or more pacing/sensing electrodes (multi-site) for use in sensing heart functions, and delivering pacing stimuli for resynchronization, including biventricular pacing and left ventricle pacing or right ventricular pacing.

In each of the embodiments, an electrical shock for defibrillation, or an electrical pacing stimuli for synchronization or pacing is delivered by a pulse generator, which can include an implantable cardioverter/defibrillator (ICD), a cardiac resynchronization therapy defibrillator (CRT-D), and/or a pacemaker. Further, in each of the foregoing embodiments, the cardiac harness can be coupled with multiple pacing/sensing electrodes to provide multi-site pacing to control cardiac function. By incorporating multi-site pacing into the cardiac harness, the system can be used to treat contractile dysfunction while concurrently treating bradycardia and tachycardia. This will improve pumping function by altering heart chamber contraction sequences while maintaining pumping rate and rhythm. In one embodiment, the cardiac harness incorporates pacing/sensing electrodes positioned on the epicardial surface of the heart adjacent to the left and right ventricle for pacing both the left and right ventricles.

In another embodiment, the cardiac harness includes multiple electrodes separating multiple panels. In this embodiment, at least some of the electrodes are positioned on or near (proximate) the epicardial surface of the heart for providing an electrical shock for defibrillation, and other of the electrodes are positioned on the epicardial surface of the heart to provide pacing stimuli useful in synchronizing the left and right ventricles, cardiac resynchronization therapy, and biventricular pacing or left ventricular pacing or right ventricular pacing.

In another embodiment, the cardiac harness includes multiple electrodes separating multiple panels. At least some of the electrodes provide an electrical shock for defibrillation, and one of the electrodes, a single site electrode, is used for pacing and sensing a single ventricle. For example, the single site electrode is used for left ventricular pacing or right ventricular pacing. The single site electrode also can be positioned near the septum in order to provide bi-ventricular pacing.

In yet another embodiment, the cardiac harness includes one or more electrodes associated with the cardiac harness for providing a pacing/sensing function. In this embodiment, a single site electrode is positioned on the epicardial surface of the heart adjacent the left ventricle for left ventricular pacing. Alternatively, a single site electrode is positioned on the surface of the heart adjacent the right ventricle to provide right ventricular pacing. Alternatively, more than one pacing/sensing electrode is positioned on the epicardial surface of the heart to treat synchrony of both ventricles, including bi-ventricular pacing.

In another embodiment, the cardiac harness includes coils that separate multiple panels. The coils have a high degree of flexibility, yet are capable of providing column strength so that the cardiac harness can be delivered by minimally invasive access.

In yet another embodiment, a system for treating a patient's heart has been contemplated, that includes a defibrillation compatible cardiac harness that does not include a lead system, and a leadless defibrillator that partially surrounds the heart (but does not touch the heart) and the harness. In this embodiment, the cardiac harness and the leadless defibrillator are delivered to the heart through the same minimally invasive access site. However, in other embodiments, the cardiac harness and leadless defibrillator are delivered to the heart through separate access sites. It has also been contemplated that the cardiac harness and leadless defibrillator could be delivered to the heart during separate surgical procedures at different dates.

In another embodiment, a system for treating a patient's heart includes a cardiac harness having an antenna for transmitting QRS signals of the heart to a defibrillator. The defibrillator may be an external defibrillator, an automatic external defibrillator ("AED"), or a leadless defibrillator implanted near the heart. To form an RF antenna on the cardiac harness, at least some of the undulations of the cardiac harness are not covered with a dielectric material, leaving the bare wire of the harness exposed at specified locations. Also, coils associated with the harness can operate as an RF antenna to transmit signals to a defibrillator. Therefore, the electric signals provided by the heart will be transmitted through the bare metal wire of the cardiac harness that is in contact with the heart's surface, or through the coils, and the signal will be received by the defibrillator.

All embodiments of the cardiac harness, including those with electrodes, are configured for delivery and implantation on the heart using minimally invasive approaches involving cardiac access through, for example, subxiphoid, subcostal, or intercostal incisions, and through the skin by percutaneous delivery using a catheter.

BRIEF DESCRIPTION OF THE DRAWINGS

FIG. 5B depicts a cross-sectional view of an electrode.

FIG. 5C depicts a cross-sectional view of an electrode.

FIG. 5D depicts a cross-sectional view of an electrode.

FIG. 6A depicts a cross-sectional view of an undulating strand or ring.

FIG. 6B depicts a cross-sectional view of an undulating strand or ring.

FIG. 6C depicts a cross-sectional view of an undulating strand or ring.

FIGS. 18A, 18B and 18C depict various views of a mold used for injecting a dielectric material around the cardiac harness and the electrodes.

FIGS. 19A, 19B and 19C depict various views of molds used in injecting a dielectric material around the cardiac harness and the electrodes.

FIG. 20 depicts a top view of a portion of an electrode having a metallic coil winding.

FIG. 21 depicts a side view of the electrode portion shown in FIG. 20.

FIG. 22 depicts a cross-sectional view taken along lines 22—22 showing lumens extending through the electrode.

FIG. 23 depicts a cross-sectional view taken along lines 23—23 depicting another embodiment of lumens extending through the electrode.

FIG. 24 depicts a top view of a portion of an electrode having multiple coil windings.

FIG. 37 depicts an exploded a side view of a delivery system with the introducer tube, dilator tube, and ejection tube shown prior to assembly.

FIG. 38 depicts a cross-sectional view of the introducer tube taken along lines 38—38.

FIG. 39 depicts a cross-sectional view taken along lines 39—39 showing the cross-section of the dilator tube.

FIG. 40 depicts a cross-sectional view taken along lines 40—40 extending through the plate of the ejection tube and showing the various lumens in the plate.

FIG. 41 depicts a cross-sectional view taken along lines 41—41 of the proximal end of the ejection tube.

FIG. 42 depicts a longitudinal cross-sectional view and schematic of the ejection tube with the leads from the electrodes extending through the lumens in the plate and the tubing from the suction cup extending through a lumen in the plate.

DETAILED DESCRIPTION OF THE PREFERRED EMBODIMENTS

This invention relates to a method and apparatus for treating heart failure. It is anticipated that remodeling of a diseased heart can be resisted or even reversed by alleviating the wall stresses in such a heart. The present invention discloses embodiments and methods for supporting the cardiac wall and for providing defibrillation and/or pacing functions using the same system. Additional embodiments and aspects are also discussed in Applicants' co-pending application entitled "Multi-Panel Cardiac Harness" U.S. Ser. No. 60/458,991 filed Mar. 28, 2003, the entirety of which is hereby expressly incorporated by reference.

Prior Art Devices

Figure 1:
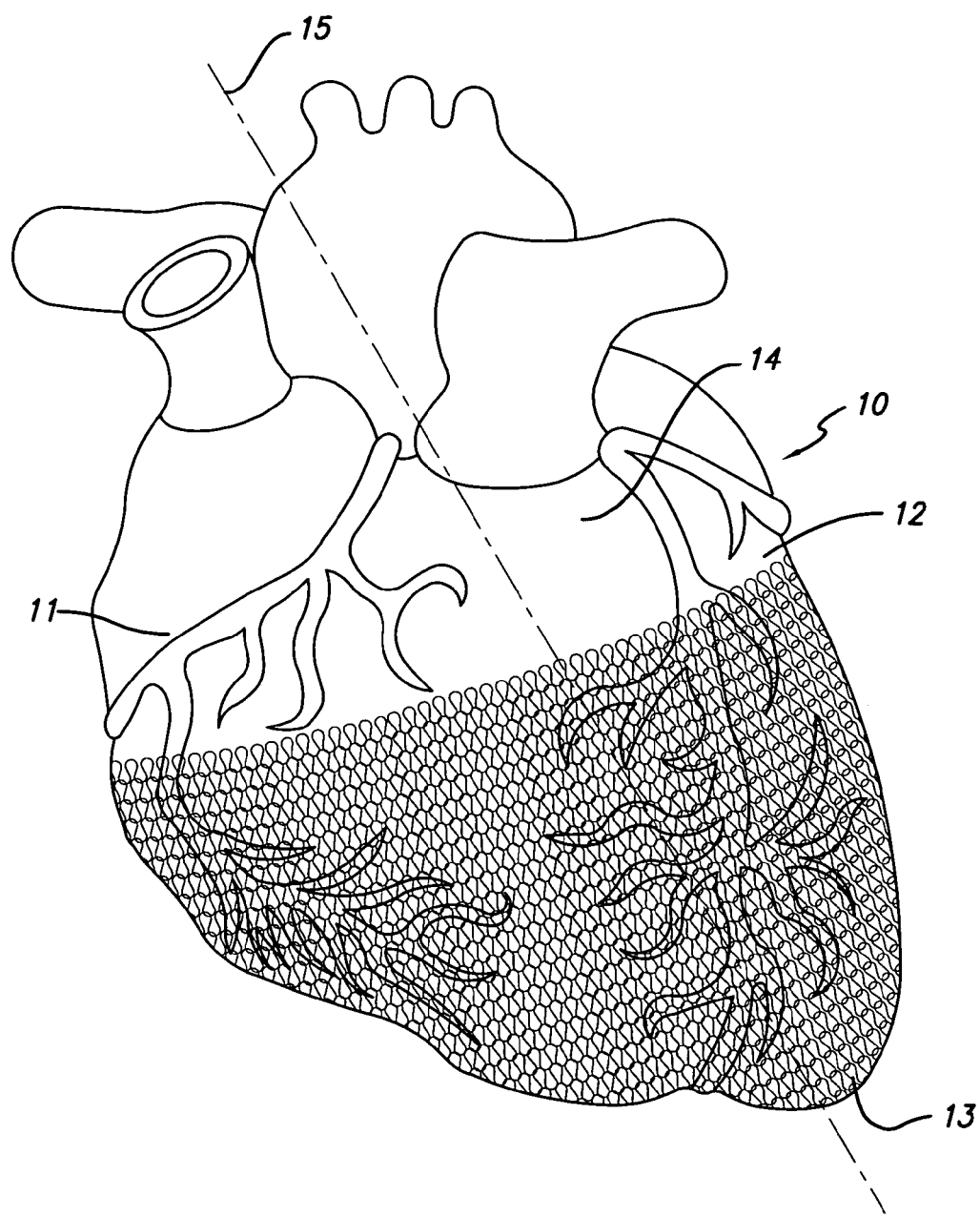
FIG. 1 depicts a schematic view of a heart with a prior art cardiac harness placed thereon.

FIG. 1 illustrates a mammalian heart 10 having a prior art cardiac wall stress reduction device in the form of a harness applied to it. The harness surrounds a portion of the heart and covers the right ventricle 11, the left ventricle 12, and the apex 13. For convenience of reference, longitudinal axis 15 goes through the apex and the AV groove 14. The cardiac harness has a series of hinges or spring elements that circumscribe the heart and, collectively, apply a mild compressive force on the heart to alleviate wall stresses.

The term "cardiac harness" as used herein is a broad term that refers to a device fit onto a patient's heart to apply a compressive force on the heart during at least a portion of the cardiac cycle.

Figure 2A:
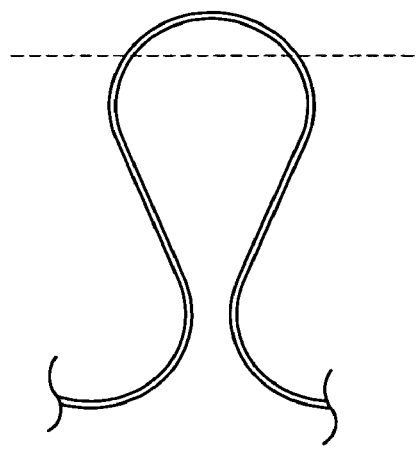
FIGS. 2A–2B depict a spring hinge of a prior art cardiac harness in a relaxed position and under tension.
Figure 2B:
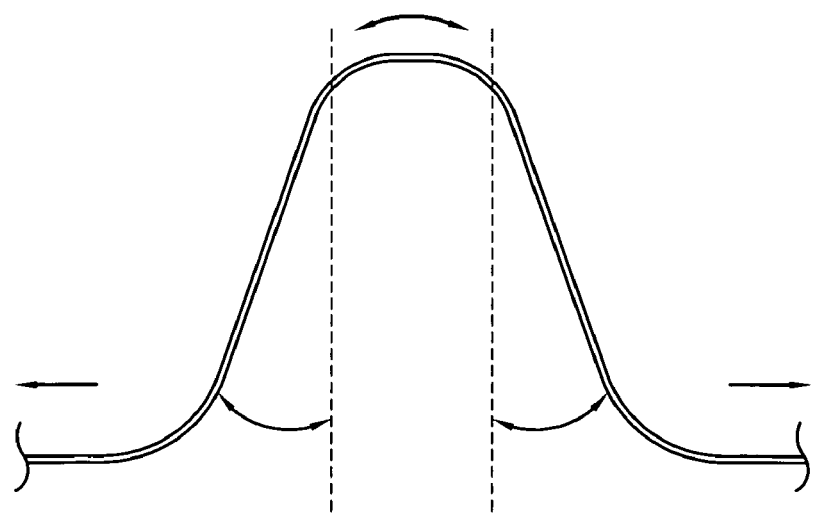

The cardiac harness illustrated in FIG. 1 has at least one undulating strand having a series of spring elements referred to as hinges or spring hinges that are configured to deform as the heart expands during filling. Each hinge provides substantially unidirectional elasticity, in that it acts in one direction and does not provide as much elasticity in the direction perpendicular to that direction. For example, FIG. 2A shows a prior art hinge member at rest. The hinge member has a central portion and a pair of arms. As the arms are pulled, as shown in FIG. 2B, a bending moment is imposed on the central portion. The bending moment urges the hinge member back to its relaxed condition. Note that a typical strand comprises a series of such hinges, and that the hinges are adapted to elastically expand and retract in the direction of the strand.

In the harness illustrated in FIG. 1, the strands of spring elements are constructed of extruded wire that is deformed to form the spring elements.

Figure 3:
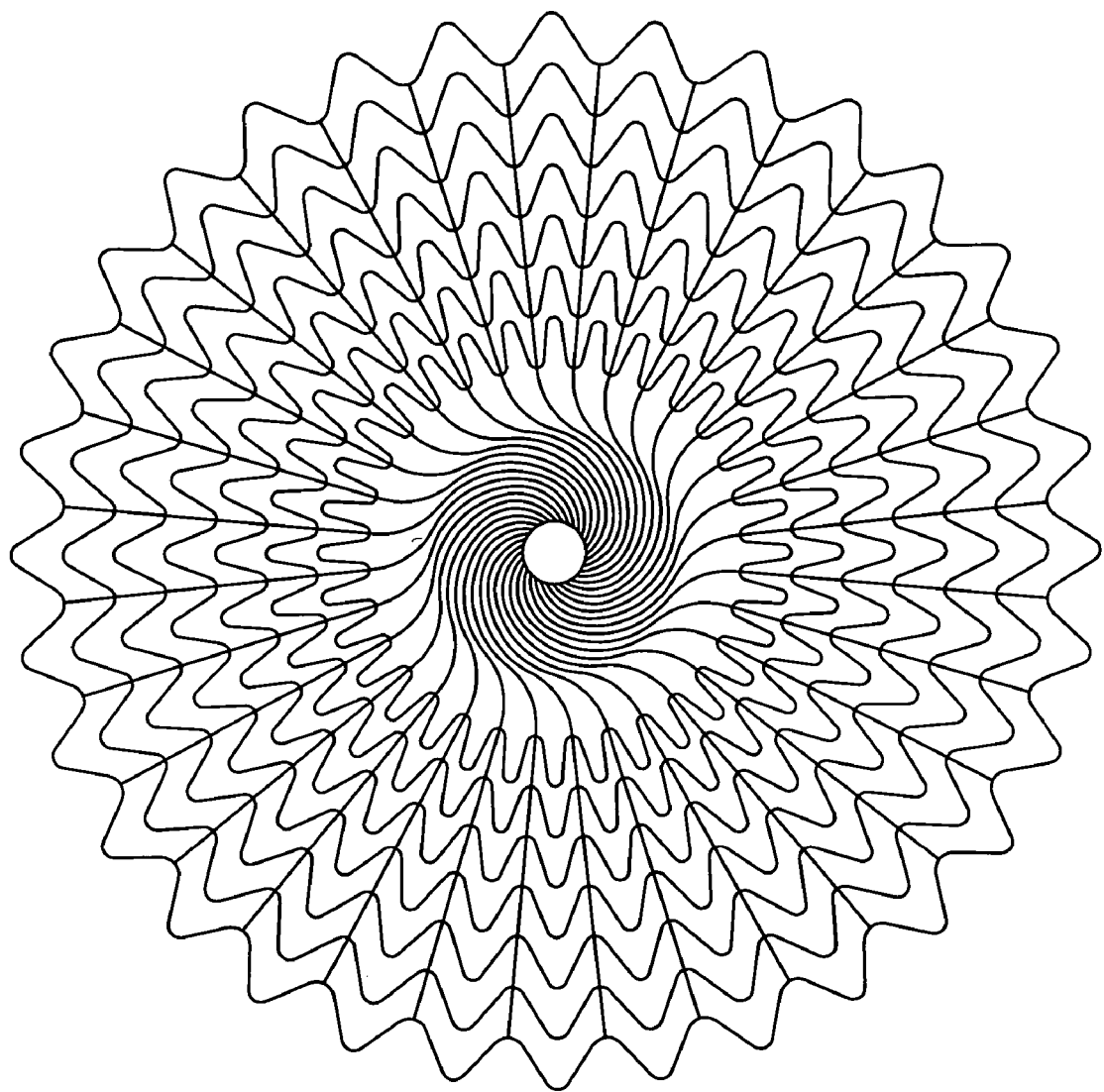
FIG. 3 depicts a prior art cardiac harness that has been cut out of a flat sheet of material.
Figure 4:
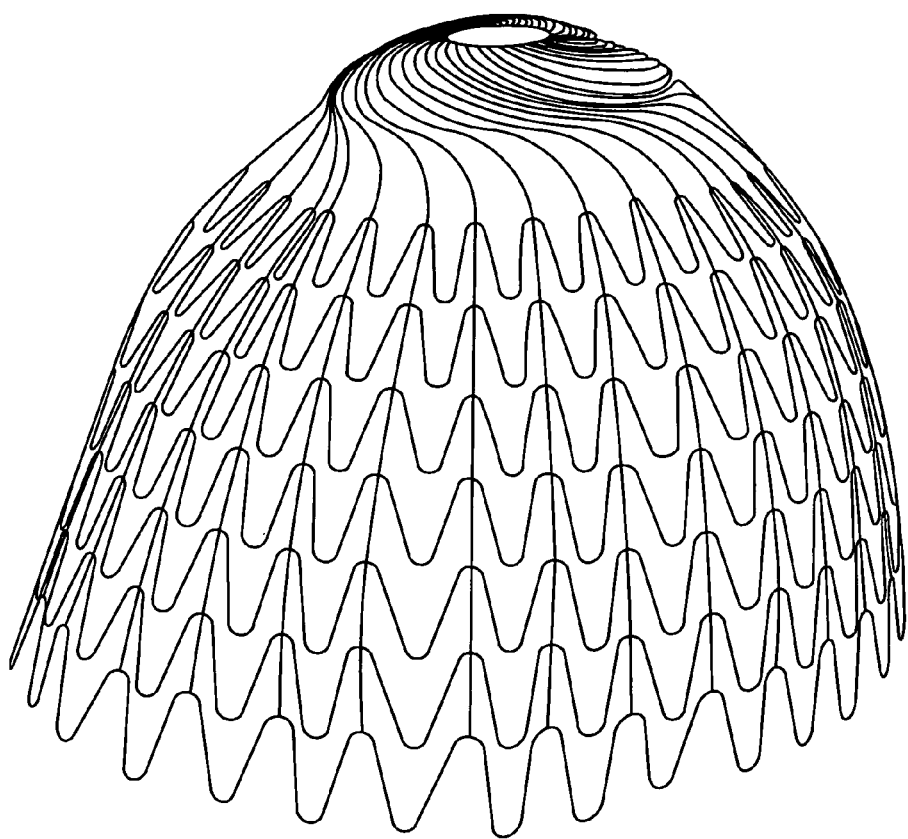
FIG. 4 depicts the prior art cardiac harness of FIG. 3 formed into a shape configured to fit about a heart.

FIGS. 3 and 4 illustrate another prior art cardiac harness, shown at two points during manufacture of such a harness. The harness is first formed from a relatively thin, flat sheet of material. Any method can be used to form the harness from the flat sheet. For example, in one embodiment, the harness is photochemically etched from the material; in another embodiment, the harness is laser-cut from the thin sheet of material. The harness shown in FIGS. 3 and 4 has been etched from a thin sheet of Nitinol, which is superelastic material that also exhibits shape memory properties. The flat sheet of material is draped over a form, die or the like, and is formed to generally take on the shape of at least a portion of a heart.

With further reference to FIGS. 1 and 4, the cardiac harnesses have a base portion which is sized and configured to generally engage and fit onto a base region of a patient's heart, an apex portion which is sized and shaped so as to generally engage and fit on an apex region of a patient's heart, and a medial portion between the base and apex portions.

In the harness shown in FIGS. 3 and 4, the harness has strands or rows of undulating wire. As discussed above, the undulations have hinge/spring elements which are elastically bendable in a desired direction. Some of the strands are connected to each other by interconnecting elements. The interconnecting elements help maintain the position of the strands relative to one another. Preferably the interconnecting elements allow some relative movement between adjacent strands.

The undulating spring elements exert a force in resistance to expansion of the heart. Collectively, the force exerted by the spring elements tends toward compressing the heart, thus alleviating wall stresses in the heart as the heart expands. Accordingly, the harness helps to decrease the workload of the heart, enabling the heart to more effectively pump blood through the patient's body and enabling the heart an opportunity to heal itself. It should be understood that several arrangements and configurations of spring members can be used to create a mildly compressive force on the heart to reduce wall stresses. For example, spring members can be disposed over only a portion of the circumference of the heart or the spring members can cover a substantial portion of the heart.

As the heart expands and contracts during diastole and systole, the contractile cells of the myocardium expand and contract. In a diseased heart, the myocardium may expand such that the cells are distressed and lose at least some contractility. Distressed cells are less able to deal with the stresses of expansion and contraction. As such, the effectiveness of heart pumping decreases. Each series of spring hinges of the above cardiac harness embodiments is configured so that as the heart expands during diastole the spring hinges correspondingly will expand, thus storing expansion forces as bending energy in the spring. As such, the stress load on the myocardium is partially relieved by the harness. This reduction in stress helps the myocardium cells to remain healthy and/or regain health. As the heart contracts during systole, the disclosed prior art cardiac harnesses apply a moderate compressive force as the hinge or spring elements release the bending energy developed during expansion allowing the cardiac harness to follow the heart as it contracts and to apply contractile force as well.

Other structural configurations for cardiac harnesses exist, however, but all have drawbacks and do not function optimally to treat CHF and other related diseases or failures. The present invention cardiac harness provides a novel approach to treat CHF and provides electrodes associated with the harness to deliver an electrical shock for defibrillation or a pacing stimulus for resynchronization, or for biventricular pacing/sensing.

The Present Invention Embodiments

The present invention is directed to a cardiac harness system for treating the heart. The cardiac harness system of the present invention couples a cardiac harness for treating the heart coupled with a cardiac rhythm management device. More particularly, the cardiac harness includes rows or undulating strands of spring elements that provide a compressive force on the heart during diastole and systole in order to relieve wall stress pressure on the heart. Associated with the cardiac harness is a cardiac rhythm management device for treating any number of irregularities in heart beat due to, among other reasons, congestive heart failure. Thus, the cardiac rhythm management device associated with the cardiac harness can include one or more of the following: an implantable cardioverter/defibrillator with associated leads and electrodes; a cardiac pacemaker including leads and electrodes used for sensing cardiac function and providing pacing stimuli to treat synchrony of both vessels; and a combined implantable cardioverter/defibrillator and pacemaker, with associated leads and electrodes to provide a defibrillation shock and/or pacing/sensing functions.

The cardiac harness system includes various configurations of panels connected together to at least partially surround the heart and assist the heart during diastole and systole. The cardiac harness system also includes one or more leads having electrodes associated with the cardiac harness and a source of electrical energy supplied to the electrodes for delivering a defibrillating shock or pacing stimuli.

Figure 5A:
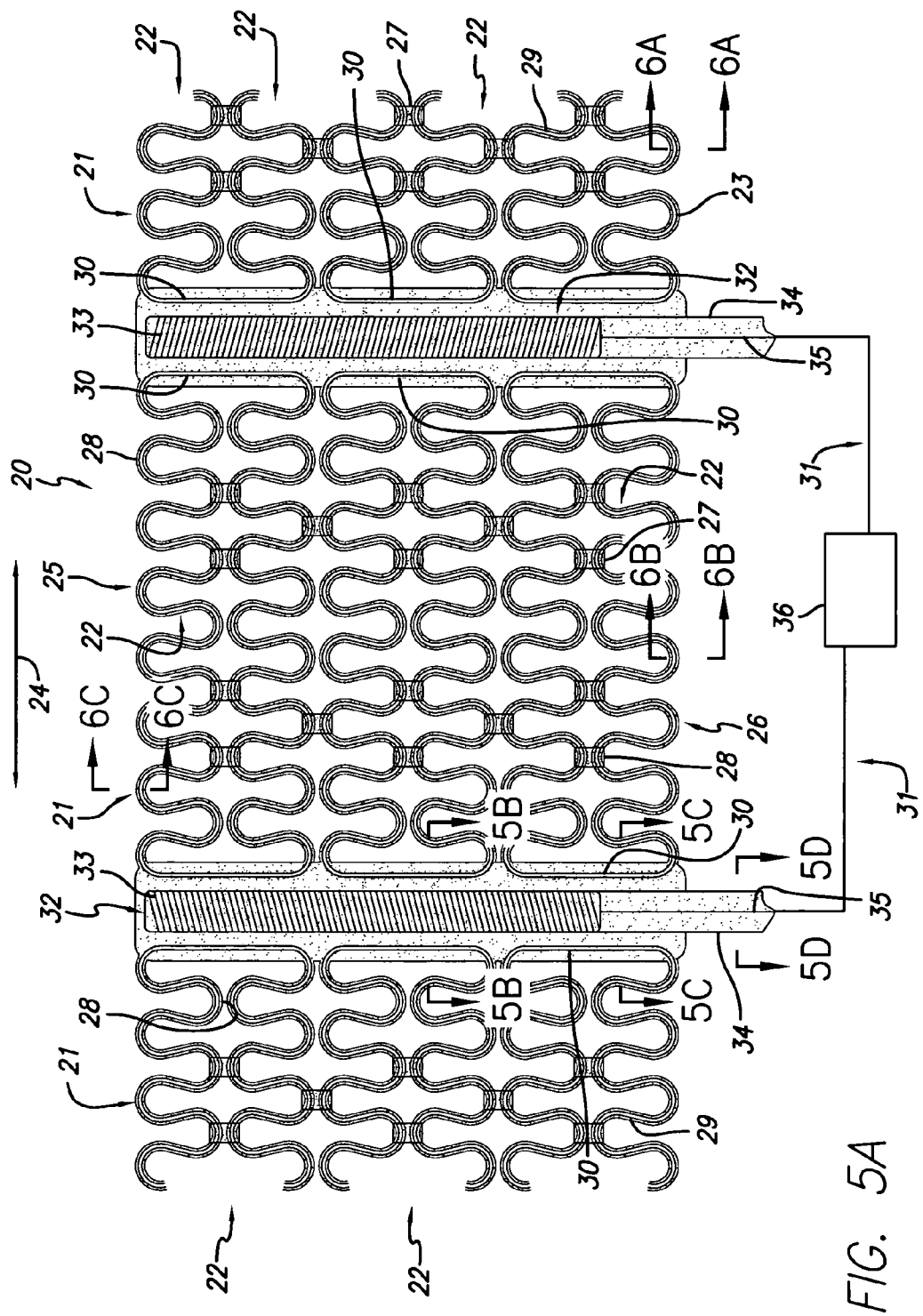
FIG. 5A depicts a flattened view of one embodiment of the cardiac harness of the invention showing two panels connected to two electrodes.

In one embodiment of the invention, as shown in a flattened configuration in FIG. 5, a cardiac harness 20 includes two panels 21 of generally continuous undulating strands 22. A panel includes rows or undulating strands of hinges or spring elements that are connected together and that are positioned between a pair of electrodes, the rows or undulations being highly elastic in the circumferential direction and, to a lesser extent, in the longitudinal direction. In this embodiment, the undulating strands have U-shaped hinges or spring elements 23 capable of expanding and contracting circumferentially along directional line 24. The cardiac harness has a base or upper end 25 and an apex or lower end 26. The undulating strands are highly elastic in the circumferential direction when placed around the heart 10, and to a lesser degree in a direction parallel to the longitudinal axis 15 of the heart. Similar hinges or spring elements are disclosed in co-pending and co-assigned U.S. Ser. No. 60/458,991 filed Mar. 28, 2003, the entire contents of which are incorporated herein by reference. While the FIG. 5 embodiment appears flat for ease of reference, in use it is substantially cylindrical (or tapered) to conform to the heart and the right and left side panels would actually be one panel and there would be no discontinuity in the undulating strands.

The undulating strands 22 provide a compressive force on the epicardial surface of the heart thereby relieving wall stress. In particular, the spring elements 23 expand and contract circumferentially as the heart expands and contracts during the diastolic and systolic functions. As the heart expands, the spring elements expand and resist expansion as they continue to open and store expansion forces. During systole, as the heart 10 contracts, the spring elements will contract circumferentially by releasing the stored bending forces thereby assisting in both the diastolic and systolic function.

As just discussed, bending stresses are absorbed by the spring elements 23 during diastole and are stored in the elements as bending energy. During systole, when the heart pumps, the heart muscles contract and the heart becomes smaller. Simultaneously, bending energy stored within the spring elements 23 is at least partially released, thereby providing an assist to the heart during systole. In a preferred embodiment, the compressive force exerted on the heart by the spring elements of the harness comprises about 10% to 15% of the mechanical work done as the heart contracts during systole. Although the harness is not intended to replace ventricular pumping, the harness does substantially assist the heart during systole.

The undulating strands 22 can have varying numbers of spring element 23 depending upon the amplitude and pitch of the spring elements. For example, by varying the amplitude of the pitch of the spring elements, the number of undulations per panel will vary as well. It may be desired to increase the amount of compressive force the cardiac harness 20 imparts on the epicardial surface of the heart, therefore the present invention provides for panels that have spring elements with lower amplitudes and a shorter pitch, thereby increasing the expansion force imparted by the spring element. In other words, all other factors being constant, a spring element having a relatively lower amplitude will be more rigid and resist opening, thereby storing more bending forces during diastole. Further, if the pitch is smaller, there will be more spring elements per unit of length along the undulating strand, thereby increasing the overall bending force stored during diastole, and released during systole. Other factors that will affect the compressive force imparted by the cardiac harness onto the epicardial surface of the heart include the shape of the spring elements, the diameter and shape of the wire forming the undulating strands, and the material comprising the strands.

As shown in FIG. 5, the undulating strands 22 are connected to each other by grip pads 27. In the embodiments shown in FIG. 5, adjacent undulating strands are connected by one or more grip pads attached at the apex 28 of the spring elements 23. The number of grip pads between adjacent undulating strands is a matter of choice and can range from one grip pad between adjacent undulating strands, to one grip pad for every apex on the undulating strand. Importantly, the grip pads should be positioned in order to maintain flexibility of the cardiac harness 20 without sacrificing the objectives of maintaining the spacing between adjacent undulating strands to prevent overlap and to enhance the frictional engagement between the grip pads and the epicardial surface of the heart. Further, while it is desirable to have the grip pads attached at the apex of the spring elements, the invention is not so limited. The grip pads 27 can be attached anywhere along the length of the spring elements, including the sides 29. Further, the shape of the grip pads 27, as shown in FIG. 5, can vary to suit a particular purpose. For example, grip pad 27 can be attached to the apex 28 of one undulating strand 22, and be attached to two apices on an adjacent undulating strand (see FIG. 7). As shown in FIG. 5, all of the apices point toward each other, and are said to be "out-of-phase." If the apices of the undulations were aligned, they would be "in-phase." The apices are all out-of-phase since the number of spring elements in each undulating strand is the same, however, the invention contemplates that the number of spring elements in each undulating strand may vary since the heart is tapered from its base near the top to its apex 13 at the bottom. Thus, there would be more spring elements and a longer undulating strand per panel at the top or base of the cardiac harness than at the bottom of the cardiac harness near the apex of the heart. Accordingly, the cardiac harness would be tapered from the relatively wide base to a relatively narrow bottom toward the apex of the heart, and this would affect the alignment of the apices of the spring elements, and hence the ability of the grip pads 27 to align perfectly and attach to adjacent apices of the spring elements. A further disclosure and embodiments relating to the undulating strands and the attachment means in the form of grip pads is found in co-pending and co-assigned U.S. Ser. No. 60/486,062 filed Jul. 10, 2003, the entire contents of which are incorporated herein by reference. While the connections between adjacent undulating strands 22 is preferably grip pads 27, in an alternative embodiment (not shown) the undulating strands are connected by interconnecting elements made of the same material as the strands. The interconnecting elements can be straight or curved as shown in FIGS. 8A–8B of commonly owned U.S. Pat. No. 6,612,979 B2, the entire contents of which is incorporated by reference herein.

It is preferred that the undulating strands 22 be continuous as shown in FIG. 5. For example, every pair of adjacent undulating strands are connected by bar arm 30. It is preferred that the bar arms form part of a continuous wire that is bent to form the undulating strands, and then welded at its ends along the bar arm. The weld is not shown in FIG. 5, but can be by any conventional method such as laser welding, fusion bonding, or conventional welding. The type of wire used to form the undulating strands may have a bearing on the method of attaching the ends of the wire used to form the undulating strand. For example, it is preferred that the undulating strands be made out of a nickel-titanium alloy, such as Nitinol, which may lose some of its superelastic or shape memory properties if exposed to high heat during conventional welding.

Associated with the cardiac harness of the present invention is a cardiac rhythm management device as previously disclosed. Thus, associated with the cardiac harness as shown in FIG. 5, are one or more electrodes for use in providing defibrillating shock. As can be seen immediately below, any number of factors associated with congestive heart failure can lead to fibrillation, acquiring immediate action to save the patient's life.

Diseased hearts often have several maladies. One malady that is not uncommon is irregularity in heartbeat caused by irregularities in the electrical stimulation system of the heart. For example, damage from a cardiac infarction can interrupt the electrical signal of the heart. In some instances, implantable devices, such as pacemakers, help to regulate cardiac rhythm and stimulate heart pumping. A problem with the heart's electrical system can sometimes cause the heart to fibrillate. During fibrillation, the heart does not beat normally, and sometimes does not pump adequately. A cardiac defibrillator can be used to restore the heart to normal beating. An external defibrillator typically includes a pair of electrode paddles applied to the patient's chest. The defibrillator generates an electric field between electrodes. An electric current passes through the patient's heart and stimulates the heart's electrical system to help restore the heart to regular pumping.

Sometimes a patient's heart begins fibrillating during heart surgery or other open-chest surgeries. In such instances, a special type of defibrillating device is used. An open-chest defibrillator includes special electrode paddles that are configured to be applied to the heart on opposite sides of the heart. A strong electric field is created between the paddles, and an electric current passes through the heart to defibrillate the heart and restore the heart to regular pumping.

In some patients that are especially vulnerable to fibrillation, an implantable heart defibrillation device may be used. Typically, an implantable heart defibrillation device includes an implantable cardioverter defibrillator (ICD) or a cardiac resynchronization therapy device (CRT-D) which usually has only one electrode positioned in the right ventricle, and the return electrode is the defibrillator housing itself, typically implanted in the pectoral region. Alternatively, an implantable device includes two or more electrodes mounted directly on, in or adjacent the heart wall. If the patient's heart begins fibrillating, these electrodes will generate an electric field therebetween in a manner similar to the other defibrillators discussed above.

Testing has indicated that when defibrillating electrodes are applied external to a heart that is surrounded by a device made of electrically conductive material, at least some of the electrical current disbursed by the electrodes is conducted around the heart by the conductive material, rather than through the heart. Thus, the efficacy of defibrillation is reduced. Accordingly, the present invention includes several cardiac harness embodiments that enable defibrillation of the heart and other embodiments disclose means for defibrillating, resynchronization, left ventricular pacing, right ventricular pacing, and biventricular pacing/sensing.

In further keeping with the invention, the cardiac harness 20 includes a pair of leads 31 having conductive electrode portions 32 that are spaced apart and which separate panels 21. As shown in FIG. 5, the electrodes are formed of a conductive coil wire 33 that is wrapped around a non-conductive member 34, preferably in a helical manner. A conductive wire 35 is attached to the coil wire and to a power source 36. As used herein, the power source 36 can include any of the following, depending upon the particular application of the electrode: a pulse generator; an implantable cardioverter/defibrillator; a pacemaker; and an implantable cardioverter/defibrillator coupled with a pacemaker. In the embodiment shown in FIG. 5, the electrodes are configured to deliver an electrical shock, via the conductive wire and the power source, to the epicardial surface of the heart so that the electrical shock passes through the myocardium. Even though the electrodes are spaced so that they would be about 180° apart around the circumference of the heart in the embodiment shown, they are not so limited. In other words, the electrodes can be spaced so that they are about 45° apart, 60° apart, 90° apart, 120° apart, or any arbitrary arc length spacing, or, for that matter, essentially any arc length apart around the circumference of the heart in order to deliver an appropriate electrical shock. As previously described, it may become necessary to defibrillate the heart and the electrodes 32 are configured to deliver an appropriate electrical shock to defibrillate the heart.

Still referring to FIG. 5, the electrodes 32 are attached to the cardiac harness 20, and more particularly to the undulating strands 22, by a dielectric material 37. The dielectric material insulates the electrodes from the cardiac harness so that electrical current does not pass from the electrode to the harness thereby undesirably shunting current away from the heart for defibrillation. Preferably, the dielectric material covers the undulating strands 22 and covers at least a portion of the electrodes 32. In the FIG. 5 embodiment, the middle panel undulating strands are covered with the dielectric material while the right and left side panels are bare metal. While it is preferred that all of the undulating strands of the panels be coated with the dielectric material, thereby insulating the harness from the electric shock delivered by the electrodes, some or all of the undulating strands can be bare metal used to deliver the electrical shock to the epicardial surface of the heart for defibrillation or for pacing.

As will be described in more detail, the electrodes 32 have a conductive discharge first surface 38 that is intended to be proximate to or in direct contact with the epicardial surface of the heart, and a conductive discharge second surface 39 that is opposite to the first surface and faces away from the heart surface. As used herein, the term "proximate" is intended to mean that the electrode is positioned near or in direct contact with the outer surface of the heart, such as the epicardial surface of the heart. The first surface and second surface typically will not be covered with the dielectric material 37 so that the bare metal conductive coil can transmit the electrical current from the power source (pulse generator), such as an implantable cardioverter/defibrillator (ICD or CRT-D) 36, to the epicardial surface of the heart. In an alternative embodiment, either the first or the second surface may be covered with dielectric material in order to preferentially direct the current through only one surface. Further details of the construction and use of the leads 31 and electrodes 33 of the present invention, in conjunction with the cardiac harness, will be described more fully herein.

Importantly, the dielectric material 37 used to attach the electrodes 32 to the undulating strands 22 insulates the undulating strands from any electrical current discharged through the conductive metal coils 33 of the electrodes. Further, the dielectric material in this embodiment is flexible so that the electrodes can serve as a seam or hinge to fold the cardiac harness 20 into a lower profile for minimally invasive delivery. Thus, as will be described in more detail (see FIGS. 13 and 14), the cardiac harness can be folded along its length, along the length of the electrodes, in order to reduce the profile for intercostal delivery, for example through the rib cage or other area typically used for minimally invasive surgery for accessing the heart. Minimally invasive approaches involving the heart typically are made through subxiphoid, subcostal or intercostal incisions. When the cardiac harness is folded, it can be reduced into a circular or a more or less oval shape, both of which promote minimally invasive procedures.

In further keeping with the invention, cross sectional views of the leads 31 and the electrode portion 32 are shown in FIGS. 5B, 5C, and 5D. As shown in FIG. 5B, the electrode 32 has the coil wire 33 wrapped around the non-conducting member 34 in a helical pattern. The dielectric material 37 provides a spaced connection between the electrode and the bar arms 30 at the ends of the undulating strands 22. The electrodes do not touch or overlap with the bar arms or any portion of the undulating strands. Instead, the dielectric material provides the attachment means between the electrodes and the bar arms of the undulating strands. Thus, the dielectric material 37 not only acts as an insulating non-conductive material, but also provides attachment means between the undulating strands and the electrodes. Because the dielectric material 37 is relatively thin at the attachment points, it is highly flexible and permits the electrodes to be flexible along with the cardiac harness panels 21, which will expand and contract as the heart beats as previously described.

Referring to FIG. 5C, the non-conductive member 34 extends beyond the coil wire 33 for a distance. The non-conductive member preferably is made from the same material as the dielectric material 37, typically a silicone rubber or similar material. While it is preferred that the dielectric material be made from silicone rubber, or a similar material, it also can be made from Parylene™ (Union Carbide), polyurethanes, PTFE, TFE, and ePTFE. As can be seen, the non-conductive member provides support for the dielectric material to attach the bar arms 30 of the undulating strands 22 in order to connect the strands to the electrode 32. A conductive wire 35 extends through the non-conducting member and attaches to the proximal end of the coil wire 33 so that when an electrical current is delivered from the power source 36 through conductive wire 35, the electrode coil 33 will be energized. The conductive wire 35 is also covered by non-conducting material 34. Referring to FIG. 5D, it can be seen that the non-conductive member 34 continues to extend beyond the bottom (apex) of the cardiac harness and that conductive wire 35 continues to extend out of the non-conductive member and into the power source 36. In the embodiment shown in FIGS. 5B–5D, the cardiac harness is insulated from the electrodes by the dielectric material 37 so that there is no shunting of electrical currents by the cardiac harness 20 from the electrical shock delivered by the electrodes during defibrillation or pacing functions.

While it is preferred that the cardiac harness 20 be comprised of undulating strands 22 made from a solid wire member, such as a superelastic or shape memory material such as Nitinol, and be insulated from the electrodes 32, it is possible to use some or all of the undulating strands to deliver the electrical shock to the epicardial surface of the heart. For example, as shown in FIG. 6A, a composite wire 45 can be used to form the undulating strands 22 and, importantly, to effectively transmit current to deliver an electrical shock to the epicardial surface of the heart. The composite wire 45 includes a current conducting wire 47 made from, for example silver (Ag), and which is covered by a Nitinol tube 46. In order to improve the surface conductivity of the outer Nitinol tube 46, a highly conductive coating is placed on the Nitinol tube. For example, the Nitinol tube can be covered with a deposition layer of platinum (Pt) or platinum-iridium (Pt—Ir), or an equivalent material including iridium oxide (IROX). The composite wire, so constructed, will have superior mechanical performance to expand and contract due to the Nitinol tubing, and also will have improved electrical properties resulting from the current conducting wire 47 and improved electrolytic/electrochemical properties via the surface layer of platinum-iridium. Thus, if some portion or all of the undulating strands 22 are made from a composite wire 45, the cardiac harness 20 will be capable of delivering a defibrillating shock on selected portions of the heart via the undulating strands and will also function to impart compressive forces as previously described.

In contrast to the current conducting undulating strands of FIG. 6A, are the non-conducting insulated undulating strands 22 as shown by cross sectional view FIG. 6B. As previously described, some or all of the undulating strands 22 can be covered with dielectric material 37 in order to insulate the strands from the electrical current delivered through the electrodes while delivering shock on the epicardial surface of the heart. Thus, as shown in FIG. 6B, the undulating strands 22 are covered by dielectric material 37 to provide insulation from the electrical shock delivered by the electrodes 32, yet maintain the flexibility and the expansive properties of the undulating strands.

An important aspect of the invention is to provide a cardiac harness 20 that can be implanted minimally invasively and be attached to the epicardial surface of the heart, without requiring sutures, clips, screws, glue or other attachment means. Importantly, the undulating strands 22 may provide relatively high frictional engagement with the epicardial surface, depending on the cross-sectional shape of the strands. For example, in the embodiment disclosed in FIG. 6C, the cross-sectional shape of the undulating strands 22 can be circular, rectangular, triangular or for that matter, any shape that increases the frictional engagement between the undulating strands and the epicardial surface of the heart. As shown in FIG. 6C, the middle cross-section view having a flat rectangular surface (wider than tall) not only has a low profile for enhancing minimally invasive delivery of the cardiac harness, but it also has rectangular edges that may have a tendency to engage and dig into the epicardium to increase the frictional engagement with the epicardial surface of the heart. With the proper cross-sectional shape for the undulating strands, coupled with the grip pads 27 having a high frictional engagement feature, the necessity for suturing, clipping, or further attachment means to attach the cardiac harness to the epicardial surface of the heart becomes unnecessary.

Figure 7A:
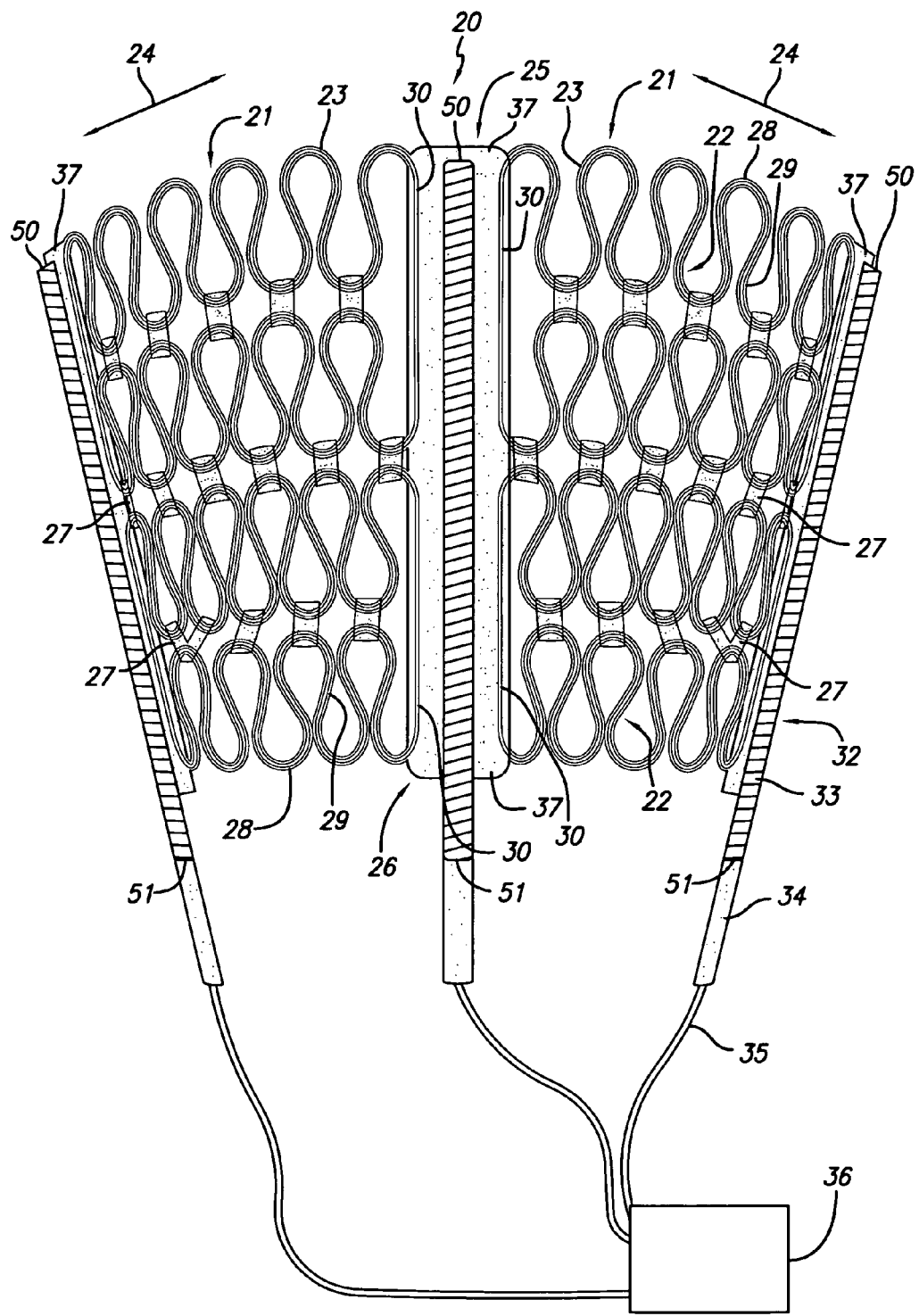
FIG. 7A depicts an enlarged plan view of a cardiac harness showing three electrodes separating three panels, with the far side panel not shown for clarity.
Figure 7B:
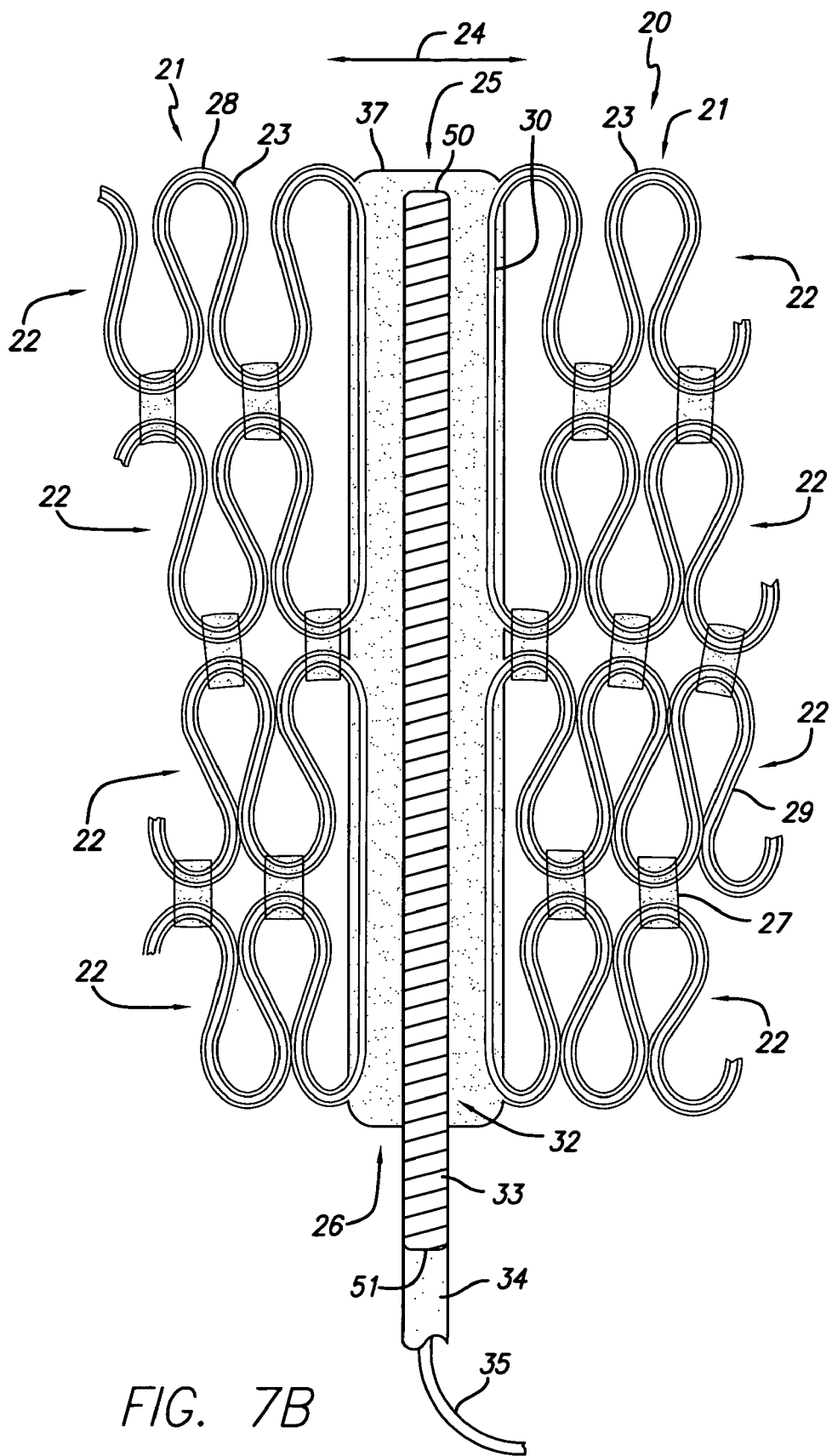
FIG. 7B depicts an enlarged partial plan view of the cardiac harness of FIG. 7A showing an electrode partially covered with a dielectric material which also serves to attach the panels to the electrode.
Figure 8A:
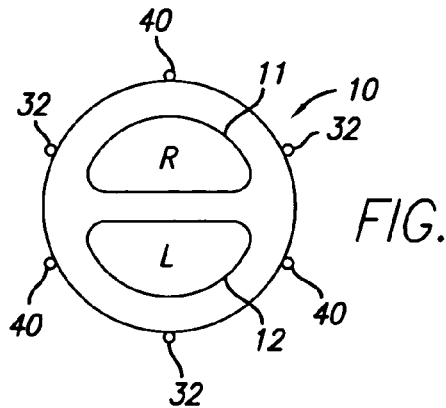
FIG. 8A depicts a transverse cross-sectional view of the heart showing the position of electrodes for defibrillation and/or pacing/sensing functions.
Figure 8B:
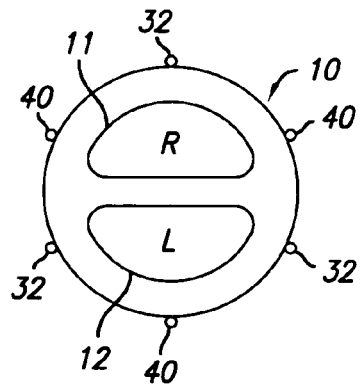
FIG. 8B depicts a transverse cross-sectional view of the heart showing the position of electrodes for defibrillation and/or pacing/sensing functions.
Figure 8C:
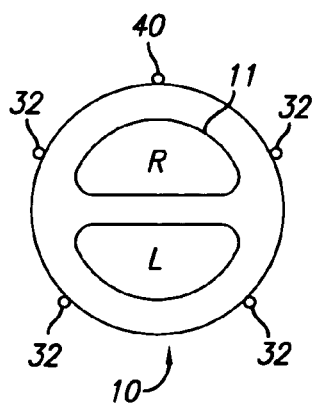
FIG. 8C depicts a transverse cross-sectional view of the heart showing the position of electrodes for defibrillation and/or pacing/sensing functions.
Figure 8D:
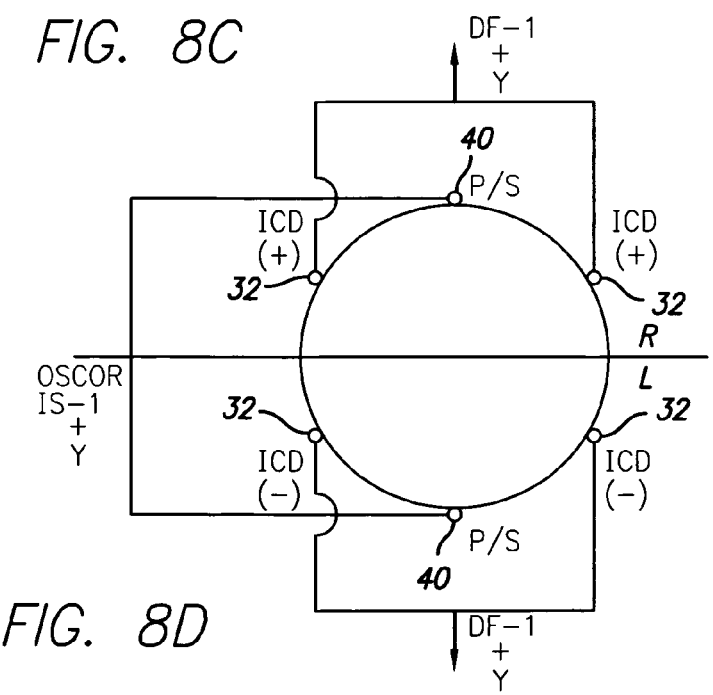
FIG. 8D depicts a transverse cross-sectional view of the heart showing the position of electrodes for defibrillation and/or pacing/sensing functions.

In another embodiment as shown in FIGS. 7A and 7B, a different configuration for cardiac harness 20 and the electrodes 32 are shown, as compared to the FIG. 5 embodiments. In FIGS. 7A and 7B, three electrodes are shown separating the three panels 21 with undulating strands 22 extending between the electrodes. As with previous embodiments, springs 23 are formed by the undulating strands so that the undulating strands can expand and contract during the diastolic and systolic functions, and apply a compressive force during both functions. The far side panel of FIG. 7A is not shown for clarity purposes. The position of the electrodes around the circumference of the heart is a matter of choice, and in the embodiment of FIG. 7A, the electrodes can be spaced an equal distance apart at about 120°. Alternatively, it may be important to deliver the electrical shock more through the right ventricle requiring the positioning of the electrodes closer to the right ventricle than to the left ventricle. Similarly, it may be more important to deliver an electrical shock to the left ventricle as opposed to the right ventricle. Thus, positioning of electrodes, as with other embodiments, is a matter of choice.

Still referring to FIGS. 7A and 7B, in this embodiment electrodes 32 extend beyond the bottom or apex portion of the cardiac harness 20 in order to insure that the electrical shock delivered by the electrodes is delivered to the epicardial surface of the heart and including the lower portion of the heart closer to the apex 13. Thus, the electrodes 22 have a distal end 50 and a proximal end 51 where the proximal end is positioned closer to the apex 13 of the heart and the distal end is positioned closer to the base or upper portion of the heart. As used herein, distal is intended to mean further into the body and away from the attending physician, and proximal is meant to be closer to the outside of the body and closer to the attending physician. The proximal ends of the electrodes are positioned closer to the apex of the heart and provide several functions, including the ability to deliver an electrical shock closer to the apex of the heart. The electrode proximal ends also function to provide support for the cardiac harness 20 and the panels 21, and lend support not only during delivery (as will be further described herein) but in separating the panels and in gripping the epicardial surface of the heart to retain the harness on the heart without slipping.

While the FIGS. 7A and 7B embodiments show electrodes 32 separating three panels 21 of the cardiac panel 20, more or fewer electrodes and panels can be provided to suit a particular application. For example, in one preferred embodiment, four electrodes 32 separate four panels 21, so that two of the electrodes can be positioned on opposite sides of the left ventricle and two of the electrodes can be positioned on opposite sides of the right ventricle. In this embodiment, preferably all four electrodes would be used, with a first set of two electrodes on opposite sides of the right ventricle acting as one (common) electrode and a second set of two electrodes on opposite sides of the left ventricle acting as the opposite (common) electrode. Alternatively, two of the electrodes can be activated while the other two electrodes act as dummy electrodes in that they would not be activated unless necessary.

At present, commercially available implantable cardioverter/defibrillators (ICD's) are capable of delivering approximately thirty to forty joules in order to defibrillate the heart. With respect to the present invention, it is preferred that the electrodes 22 of the cardiac harness 20 of the present invention deliver defibrillating shocks having less than thirty to forty joules. The commercially available ICD's can be modified to provide lower power levels to suit the present invention cardiac harness system with electrodes delivering less than thirty to forty joules of power. As a general rule, one objective of the electrode configuration is to create a uniform current density distribution throughout the myocardium. Therefore, in addition to the number of electrodes used, their size, shape, and relative positions will also all have an impact on the induced current density distribution. Thus, while one to four electrodes are preferred embodiments of the invention, five to eight electrodes also are envisioned.

In keeping with the present invention, the cardiac harness and the associated cardiac rhythm management device can be used not only for providing a defibrillating shock, but also can be used as a pacing/sensing device for treating the synchrony of both ventricles, for resynchronization, for biventricular pacing and for left ventricular pacing or right ventricular pacing. As shown in FIGS. 8A–8D, the heart 10 is shown in cross-section exposing the right ventricle 11 and the left ventricle 12. The cardiac harness 20 is mounted around the outer surface of the heart, preferably on the epicardial surface of the heart, and multiple electrodes are associated with the cardiac harness. More specifically, electrodes 32 are attached to the cardiac harness and positioned around the circumference of the heart on opposite sides of the right and left ventricles. In the event that fibrillation should occur, the electrodes will provide an electrical shock through the myocardium and the left and right ventricles in order to defibrillate the heart. Also mounted on the cardiac harness, is a pacing/sensing lead 40 that functions to monitor the heart and provide data to a pacemaker. If required, the pacemaker will provide pacing stimuli to synchronize the ventricles, and/or provide left ventricular pacing, right ventricular pacing or biventricular pacing. Thus, for example, in FIG. 8C, pairs of pacing/sensing leads 40 are positioned adjacent the left and right ventricle free walls and can be used to provide pacing stimuli to synchronize the ventricles, or provide left ventricular pacing, right ventricular pacing or biventriculator pacing. The use of proximal Y connectors can simplify the transition to a post-generator such as Oscor's, iLink-B15-10. The iLink-B15-10 can be used to link the right and left ventricular free-wall pace/sense leads 40, as shown in 8D.

In another embodiment of the invention, as shown in FIGS. 9–14, cardiac harness 60 is similar to previously described cardiac harness 20. With respect to cardiac harness 60, it also includes panels 61 consisting of undulating strands 62. In the disclosed embodiments, the undulating strands are continuous and extend through coils as will be described. The undulating strands act as spring elements 63 as with prior embodiments that will expand and contract along directional line 64. The cardiac harness 60 includes a base or upper end 65 and an apex or lower end 66. In order to add stability to the cardiac harness 60, and to assist in maintaining the spacing between the undulating strands 62, grip pads 67 are connected to adjacent strands, preferably at the apex 68 of the springs. Alternatively, the grip pads 67 could be attached from the apex of one spring element to the side 69 of a spring element, or the grip pad could be attached from the side of one spring to the side of an adjacent spring on an adjacent undulating strand. In further keeping with the invention as shown in the FIGS. 9–14, in order to add stability and some mechanical stiffness to the cardiac harness 60, coils 62 are interwoven with the undulating strands, which together define the panels 61. The coils typically are formed of a coil of wire such as Nitinol or similar material (stainless steel, MP35N), and are highly flexible along their longitudinal length. The coils 72 have a coil apex 73 and a coil base 74 to coincide with the harness base 65 and the harness apex 66. The coils can be injected with a non-conducting material so that the undulating strands extend through gaps in the coils and through the non-conducting material. The non-conducting material also fills in the gaps which will prevent the undulating strands from touching the coils so there is no metal-to-metal touching between the undulating strands and the coils. Preferably, the non-conducting material is a dielectric material 77 that is formed of silicone rubber or equivalent material as previously described. Further, a dielectric material 78 also covers the undulating strands in the event a defibrillating shock or pacing stimuli is delivered to the heart via an external defibrillator (e.g., transthoracic) or other means.

Figure 12:
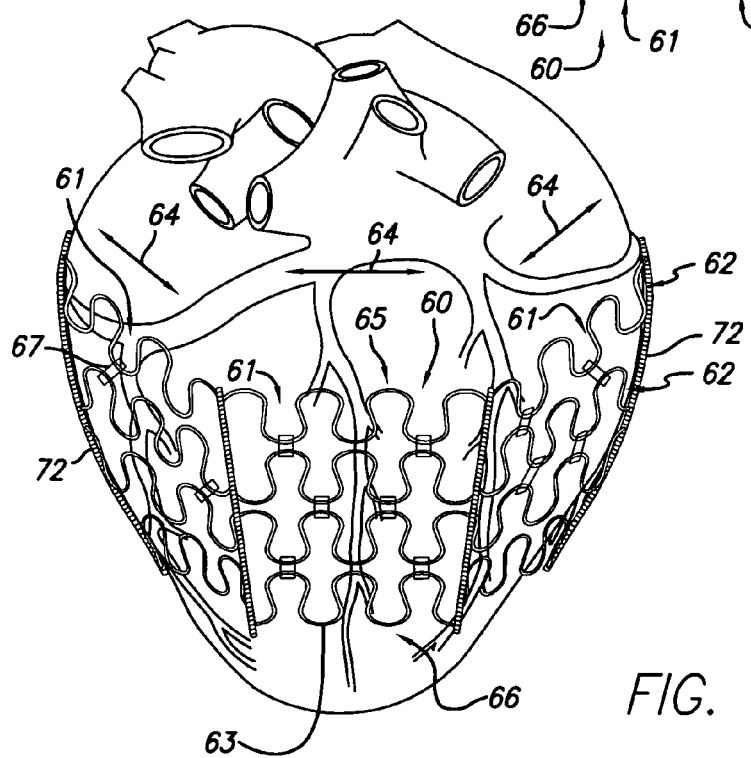
FIG. 12 depicts a plan view of a cardiac harness similar to that shown in FIG. 11 mounted on the epicardial surface of the heart.

Importantly, coils 72 not only perform the function of being highly flexible and provide the attachment means between the coils and the undulating strands, but they also provide structural columns or spines that assist in deploying the harness 60 over the epicardial surface of the heart. Thus, as shown for example in FIG. 12, the cardiac harness 60 has been positioned over the heart and delivered by minimally invasive means, as will be described more fully herein. The coils 72, although highly flexible along their longitudinal length, have sufficient column strength in order to push on the apex 73 of the coils so that the base portion 74 of the coils and of the harness 65 slide over the apex of the heart and along the epicardial surface of the heart until the cardiac harness 60 is positioned over the heart, substantially as shown in FIG. 12.

Figure 9:
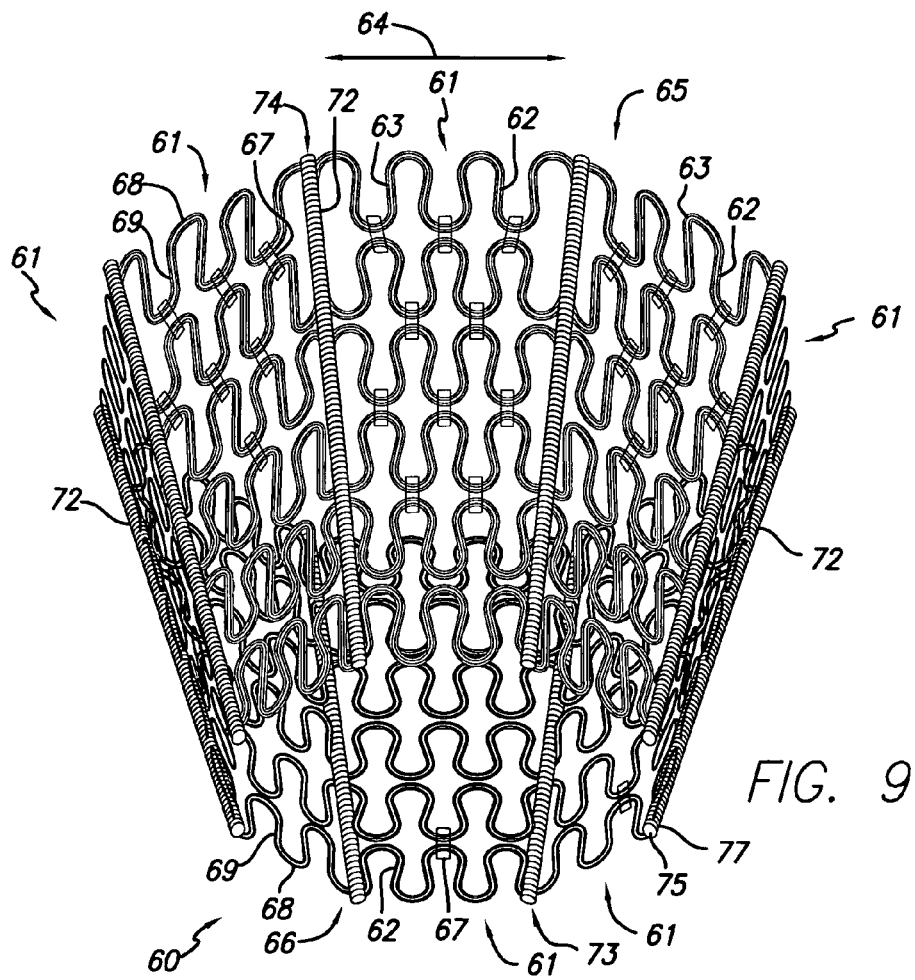
FIG. 9 depicts a plan view of one embodiment of a cardiac harness having panels separated by and attached to flexible coils.
Figure 10:
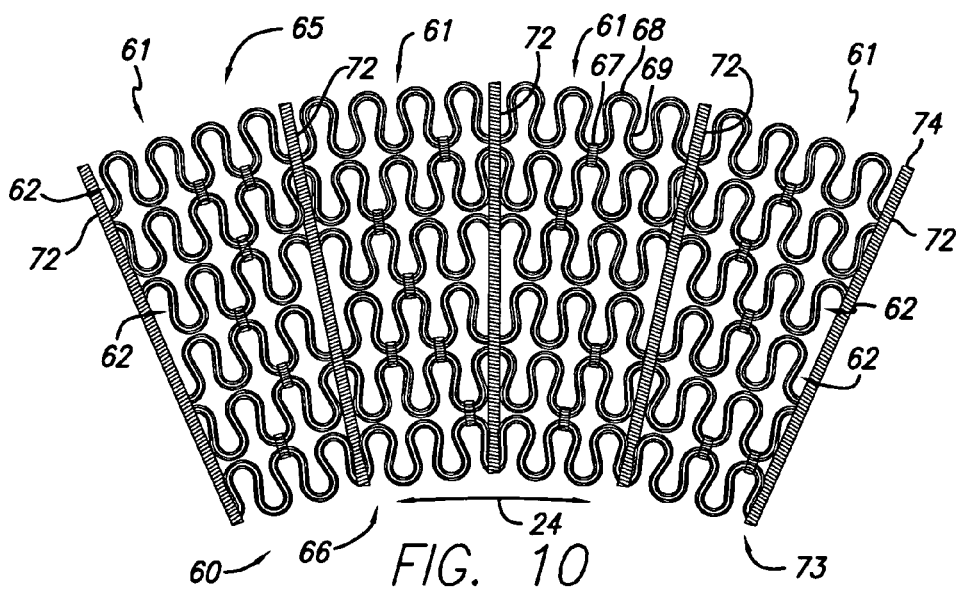
FIG. 10 depicts a flattened plan view of a cardiac harness similar to that of FIG. 9 but with fewer panels and coils.
Figure 11:
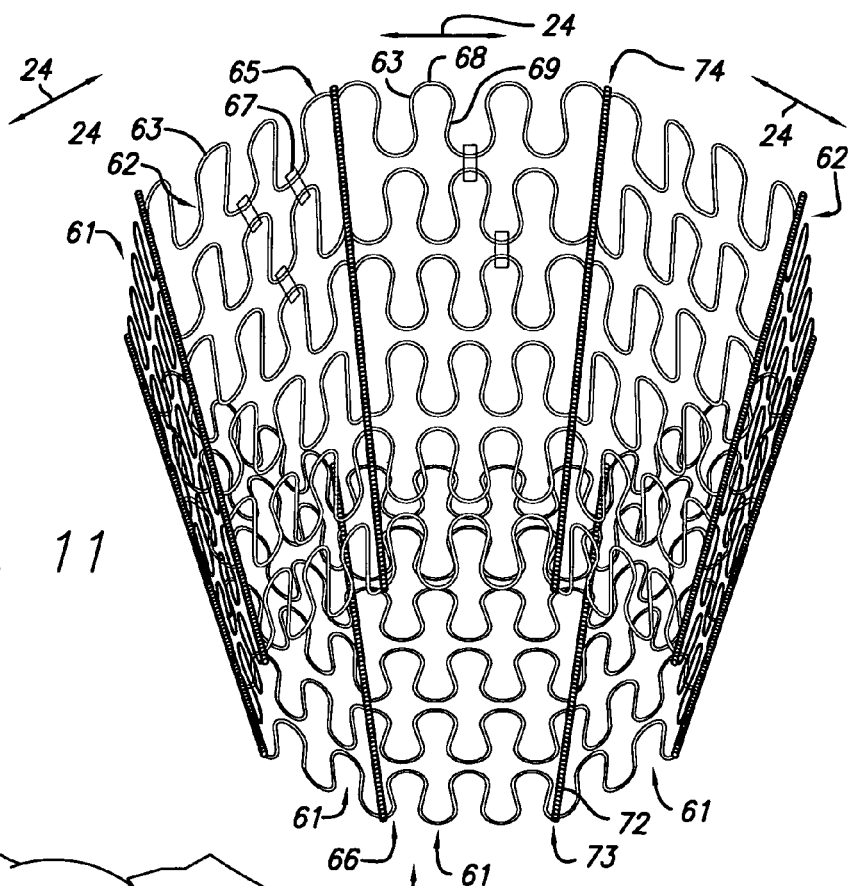
FIG. 11 depicts a plan view of one embodiment of a cardiac harness having panels separated by and attached to flexible coils.

Referring to the embodiments shown in FIGS. 9 and 11, the cardiac harness 60 has multiple panels 61 and multiple coils 72. More or fewer panels and coils can be used in order to achieve a desired result. For example, eight coils are shown in FIGS. 9 and 11, while fewer coils may provide a harness with greater flexibility since the undulating strands 62 would be longer in the space between each coil. Further, the diameter of the coils can be varied in order to increase or decrease flexibility and/or column strength in order to assist in the delivery of the harness over the heart. The coils preferably have a round cross-sectional wire in the form of a tightly wound spiral or helix so that the cross-section of the coil is circular. However, the cross-sectional shape of the coil need not be circular, but may be more advantageous if it were oval, rectangular, or another shape. Thus, if coils 72 had an oval shape, where the longer axis of the oval was parallel to the circumference of the heart, the coil would flex along its longitudinal axis and still provide substantial column strength to assist in delivery of the cardiac harness 60. Further, an oval-shaped coil would provide a lower profile for minimally invasive delivery. The wire cross-section also need not be round/circular, but can consist of a flat ribbon having a rectangular shape for low profile delivery. The coils also can have different shapes, for example they can be closed coils, open coils, laser-cut coils, wire-wound coils, multi-filar coils, or the coil strands themselves can be coiled (i.e., coiled coils). The electrode need not have a coil of wire, rather the electrode could be formed by a zig-zag-shaped wire (not shown) extending along the electrode. Such a design would be highly flexible and fatigue resistant yet still be capable of providing a defibrillating shock.

Figure 13:
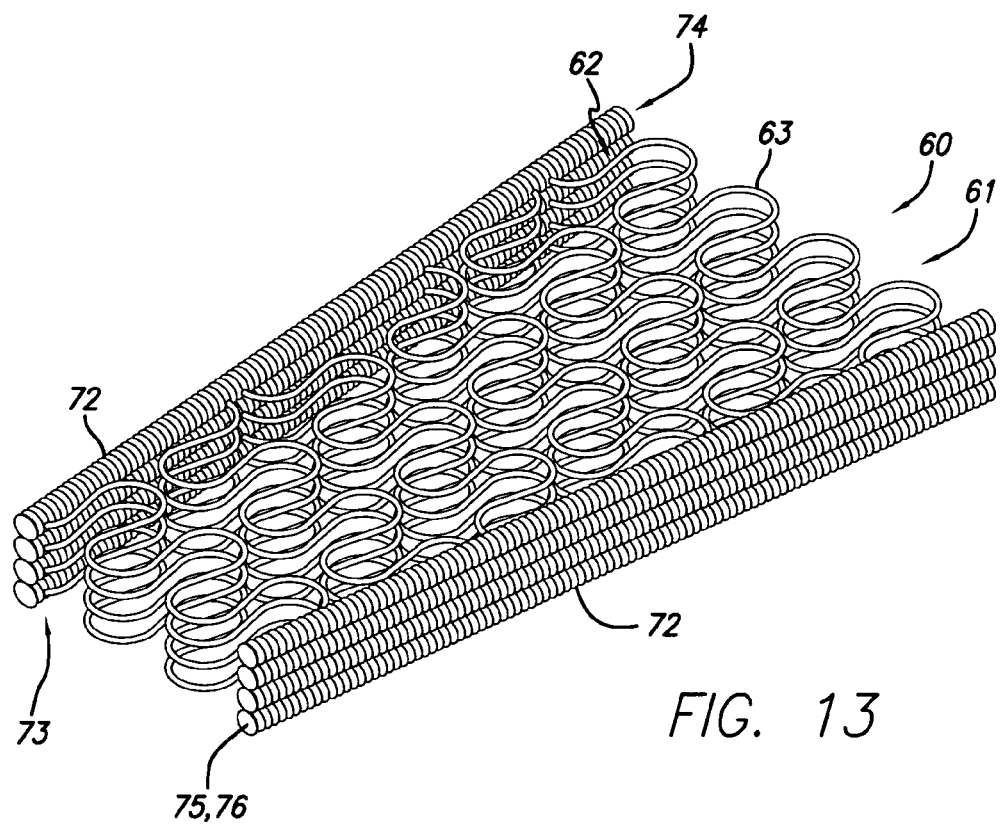
FIG. 13 depicts a perspective view of a cardiac harness similar to that of FIG. 9 where the harness has been folded to reduce its profile for minimally invasive delivery.
Figure 14:
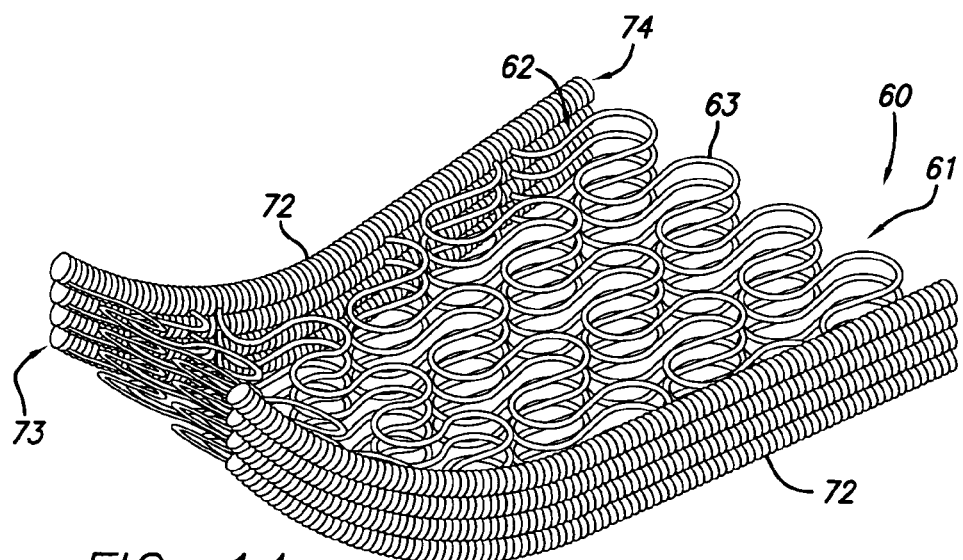
FIG. 14 depicts the cardiac harness of FIG. 13 in a partially bent and folded condition to reduce its profile for minimally invasive delivery.

The cardiac harness embodiments 60 shown in FIGS. 9–12, can be folded as shown in FIGS. 13 and 14 and yet remain highly flexible for minimally invasive delivery. The coils 72 act as hinges or spines so that the cardiac harness can be folded along the longitudinal axis of the coils. The grip pads typically connecting adjacent undulating strands 62 have been omitted for clarity in these embodiments, however, they would be used as previously described.

In an alternative embodiment, similar to the embodiment shown in FIGS. 9–12, the cardiac harness 60 includes both coils 72 and electrodes 32. In this embodiment, as with the previously described embodiments, a series of undulating strands 22 extend between the coils and the electrodes to form panels 21. In this embodiment, for example, the coils and electrodes form hinge regions so that the panels can be folded along the longitudinal axis of the coils and electrodes for minimally invasive delivery. Further, in this embodiment, there are two coils and four electrodes, with two of the electrodes positioned adjacent the right ventricle, with the remaining two electrodes being positioned adjacent the left ventricle. The coils not only act as a hinge, but provide column strength as previously described so that the cardiac harness can be delivered minimally invasively by delivery through, for example, the intercostal space between the ribs and then pushing the harness over the heart. Likewise, the electrodes provide column strength as well, yet remain flexible along their longitudinal axis, as do the coils.

Figure 15A:
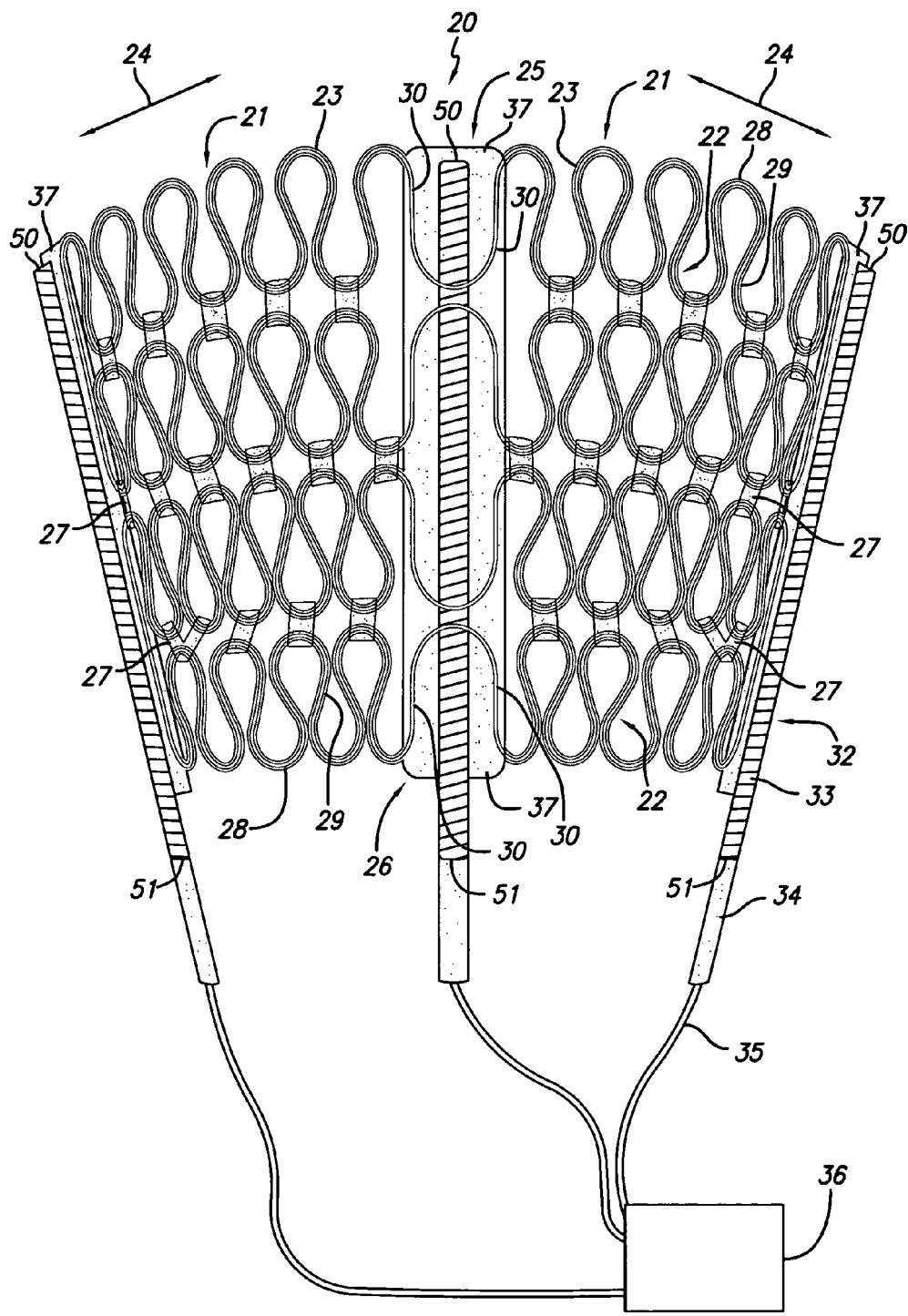
FIG. 15A depicts an enlarged plan view of a cardiac harness showing continuous undulating strands with electrodes overlaying the strands.
Figure 15B:
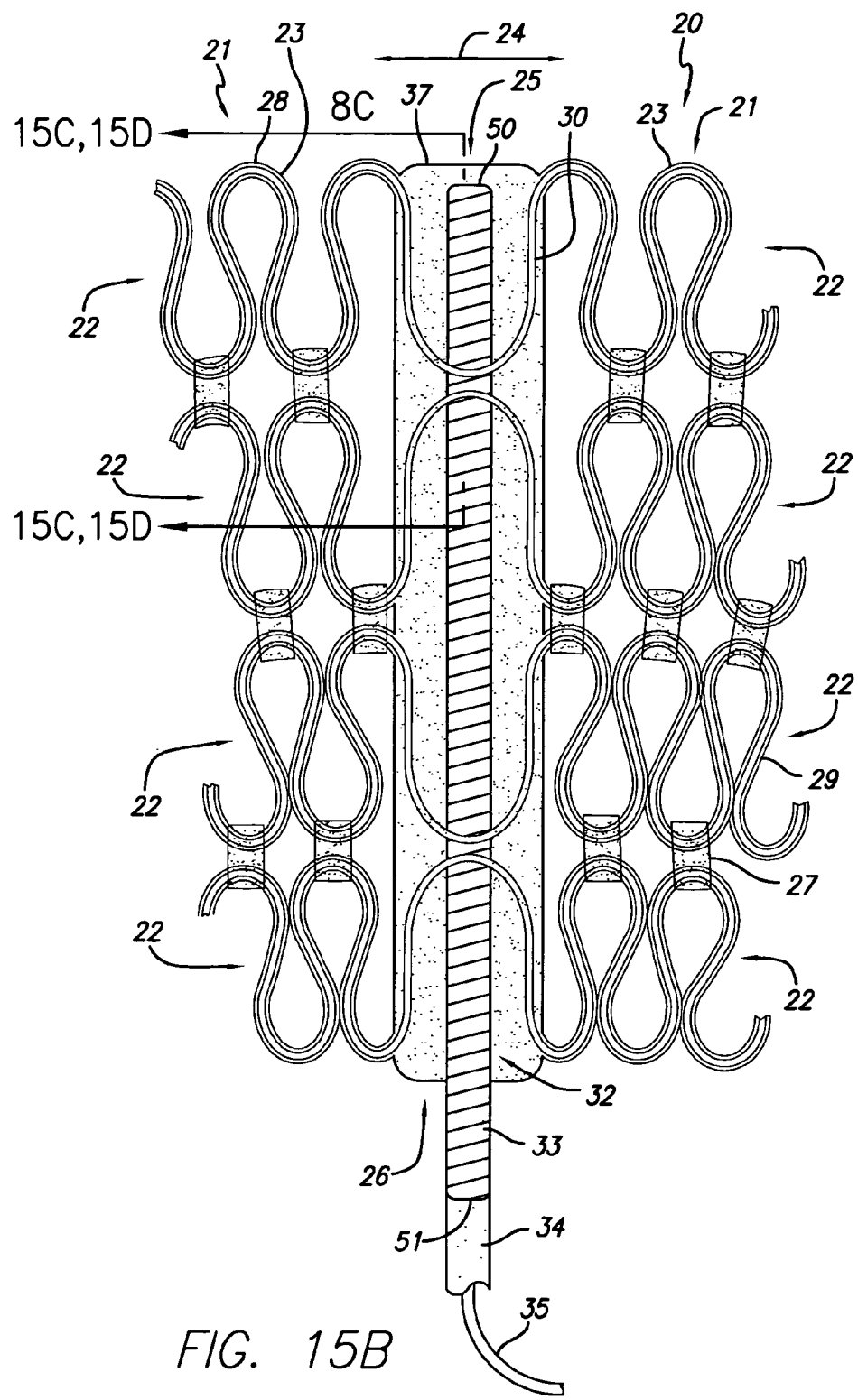
FIG. 15B depicts an enlarged partial plan view of the cardiac harness of FIG. 15A showing continuous undulating strands with an electrode overlying the strands.
Figure 15C:
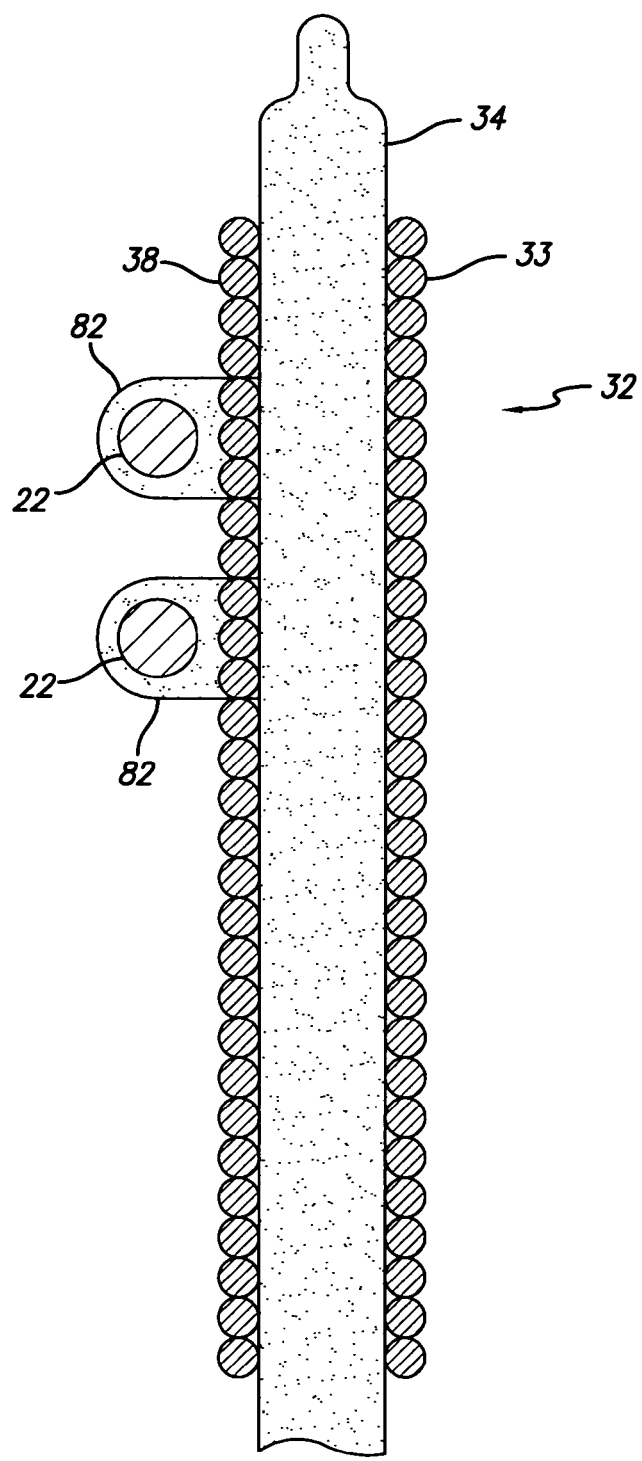
FIG. 15C depicts a partial cross-sectional view taken along lines 15C–15C showing the electrode and undulating strands.
Figure 15D:
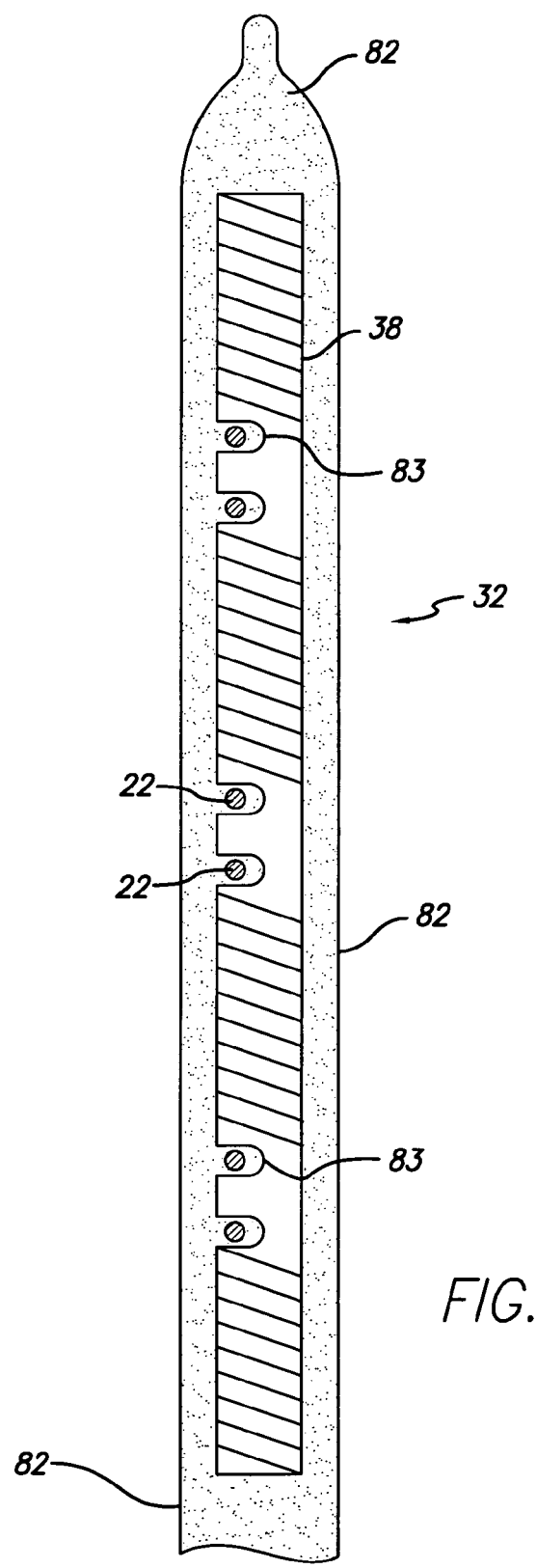
FIG. 15D depicts a partial cross-sectional view taken along lines 15D–15D showing the undulating strands in notches in the electrode.

Referring to FIGS. 15A–15D, the electrodes 32 or the coils 72 can be mounted on the inner surface (touching the heart) or outer surface (away from the heart) of the cardiac harness. Thus, the cardiac harness 20 includes continuous undulating strands 22 that extend circumferentially around the heart without any interruptions. The undulating strands are interconnected by any interconnecting means, including grip pads 27, as previously described. In this embodiment, electrodes 32 or coils 72, or both, are mounted on an inner surface 80 or an outer surface 81 of the cardiac harness 20. A dielectric material 82 is molded around the electrodes or coils and around the undulating strands in order to connect the electrodes and coils to the cardiac harness. Alternatively, as shown in FIG. 15D, the electrodes 32 or coils 72 can be formed into a fastening means by forming notches 83 into the electrode (or coil) and which are configured to receive portions of the undulating strand 22. The undulating strands 22 are spaced from the coils or electrodes so that there is no overlapping/touching of metal. The notches 83 are filled with a dielectric material, preferably silicone rubber, or similar material that insulates the undulating strands of the cardiac harness from the electrodes yet provides a secure attachment means so that the electrodes or coils remain firmly attached to the undulating strands of the cardiac harness. Importantly, the electrodes 32 do not have to be in contact with the epicardial surface of the heart in order to deliver a defibrillating shock. Thus, the electrodes 32 can be mounted on the outer surface 81 of the cardiac harness, and not be in physical contact with the epicardial surface of the heart, yet still deliver a defibrillating shock as previously described.

It is to be understood that several embodiments of cardiac harnesses can be constructed and that such embodiments may have varying configurations, sizes, flexibilities, etc. Such cardiac harnesses can be constructed from many suitable materials including various metals, fabrics, plastics and braided filaments. Suitable materials also include super-elastic materials and materials that exhibit shape memory properties. For example, a preferred embodiment cardiac harness is constructed of Nitinol. Shape memory dielectric materials can also be employed. Such shape memory dielectric materials can include shape memory polyurethanes or other dielectric materials such as those containing oligo(e-caprolactone) dimethacrylate and/or poly(e-caprolactone), which are available from mnemoScience.

Figure 16:
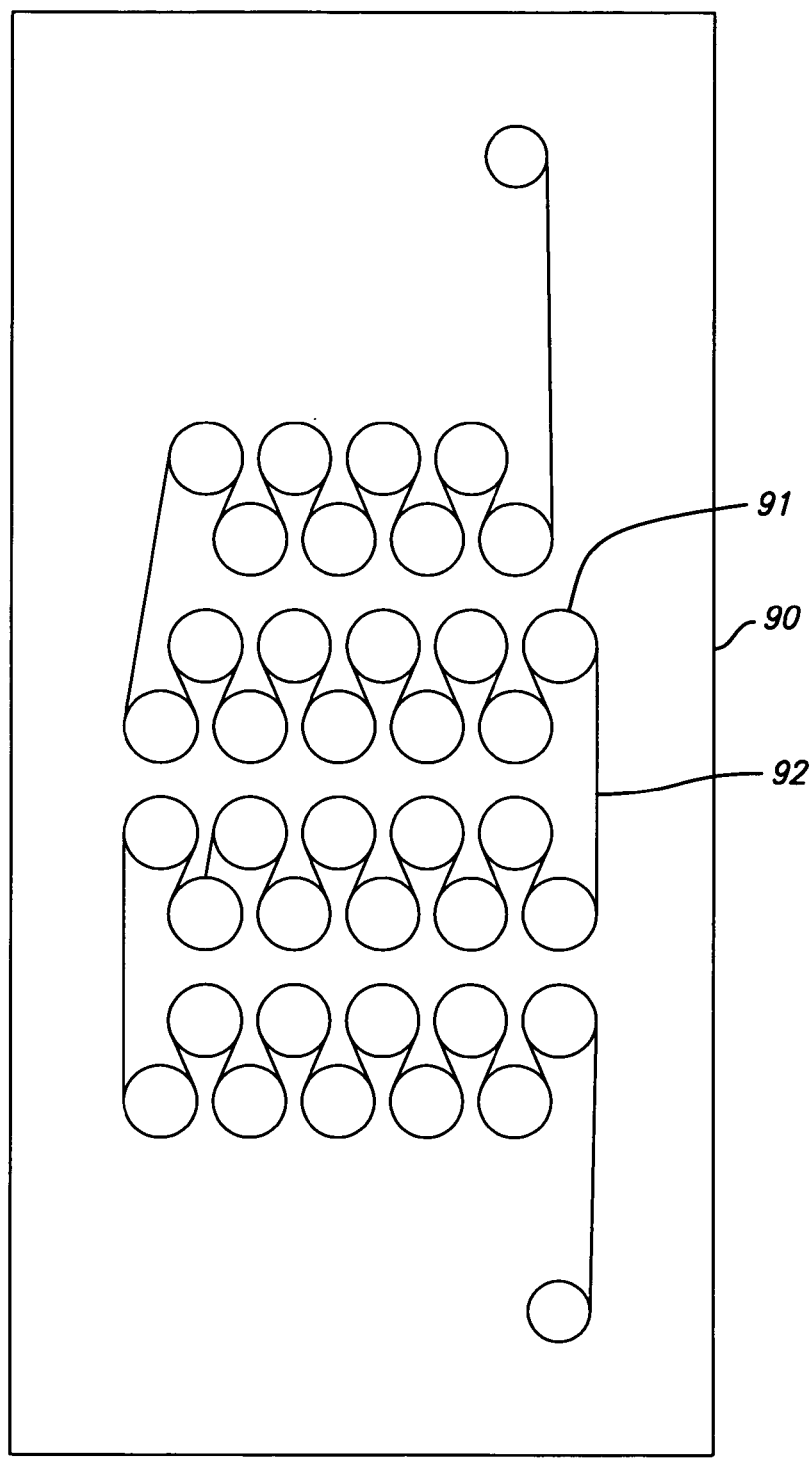
FIG. 16 depicts a top view of a fixture for winding wire to construct the cardiac harness.

In keeping with the invention, as shown in FIG. 16, the undulating strands 22 and 62 can be formed in many ways, including by a fixture 90. The fixture 90 has a number of stems 91 that are arranged in a pre-selected pattern that will define the shape of the undulating strands 22 and 62. The position of the stems will define the shape of the undulating strands, and determine whether the previously disclosed apex of the springs is either in-phase or out-of-phase. The shape of stems 91 will define the shape of the springs in terms of radius of curvature, or other shape, such as a keyhole shape, a U-shape, and the like. The spacing between the stems will determine the pitch and the amplitude of the undulating strands which is a matter of choice. Preferably, in one exemplary embodiment, a Nitinol wire 92 or other superelastic or shape memory wire having a 0.012 inch diameter, is woven between stems 91 in order to form the undulating strands. Other wire diameters can be used to suit a particular need and can range from about 0.007 inch to about 0.020 inch diameter. Other wire cross-section shapes are envisioned to be used with fixture 90, particularly a flat rectangular-shaped wire and an oval-shaped wire. The Nitinol wire is then heat set to impart the shape memory feature. Any free ends can be connected together by laser bonding, laser welding, or other type of similar connection consistent with the use of Nitinol, or the ends may remain free and be encapsulated in a dielectric material to keep them atraumatic, depending upon the design.

Again referring to FIG. 16, after the Nitinol wire is heat set to impart the shape memory feature, the wire is jacketed with NuSil silicone tubing (Helix Medical) having 0.029 inch outside diameter by 0.012 inch inside diameter. Thereafter, the jacketed Nitinol wire is placed in molds for transfer of liquid silicone rubber which will insulate the Nitinol wire from any electrical shock from any electrodes associated with the cardiac harness, or any other device providing a defibrillating shock to the heart. The dimensions of the silicone tubing will of course vary for different wire dimensions.

Figure 17:
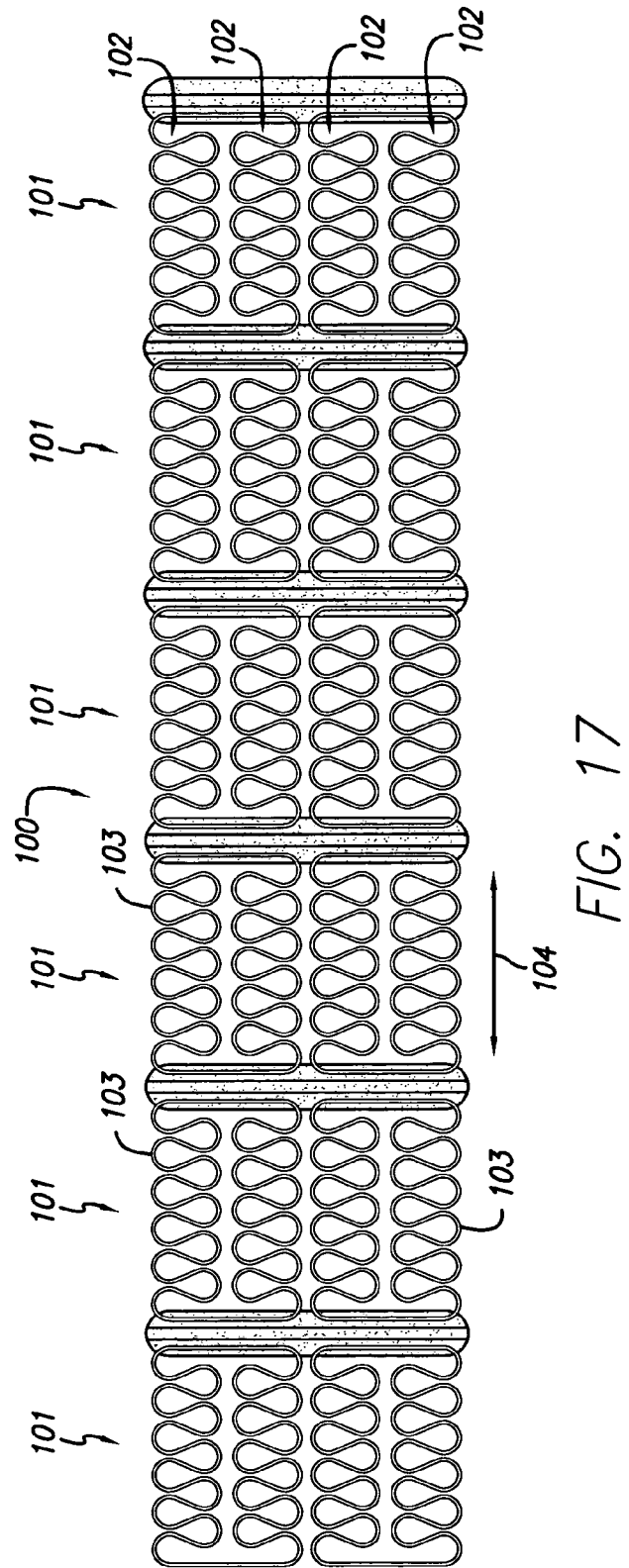
FIG. 17 depicts a plan view of a portion of a cardiac harness showing panels separated by electrodes.

In another embodiment of the invention, shown in FIG. 17, cardiac harness 100 includes multiple panels 101 similar to those previously described. Further, undulating strands 102 form the panels and have multiple spring elements 103 that expand and contract along directional line 104, also as previously described for other embodiments. In the cardiac harness 100 shown in FIG. 17, the amplitude of the spring elements is relatively smaller than in other embodiments, and the pitch is higher, meaning there are more spring elements per unit of length relative to other embodiments. Thus, the cardiac harness 100 should generate higher bending forces as the heart expands and contracts during the diastolic and systolic cycles. In other words, the spring elements 103 of cardiac harness 100 will resist expansion, thereby imparting higher compressive forces on the wall of the heart during the diastolic function and will release these higher bending forces during the systolic function as the heart contracts. It may be important to provide undulating strands 102 that alternate in amplitude and pitch within a panel, starting at the base of the harness and extending toward the apex. For example, the pitch and amplitude of an undulating strand closer to the base or the harness may be configured to impart higher compressive forces on the epicardial surface of the heart than the undulating strands closer to the apex or the lower part of the harness. It also may be desirable to alternate the amplitude and pitch of the spring elements from one undulating strand to the next. Further, where multiple panels are provided, it may be advantageous to provide one amplitude and pitch of the spring elements of the undulating strands of one panel, and a different amplitude and pitch of the spring elements of the undulating strands of an adjacent panel. The FIG. 17 embodiment can be configured with electrodes as previously described in other embodiments, or with coils, both of which assist with the delivery of the cardiac harness by providing column support to the harness.

The cardiac harness of the present invention, having either electrodes or coils, can be formed using injection molding techniques as shown in FIGS. 18A–18C and 19A–19C. The molds in FIGS. 18A–18C are substantially the same as the molds shown in FIGS. 19A–19C, with the exception of the undulating pattern grooves that receive the undulating strands previously described. In referring to FIG. 18A, bottom mold 110 includes a pattern for receiving the cardiac harness and a coil or an electrode. For illustration purposes, FIG. 18B shows top mold 111 and FIG. 18C shows end view mold 112. The top mold mates with the bottom mold. As can be seen, the cardiac harness undulating strands will fit in undulating strand groove 113, which extend into coil groove 114. The previously described electrodes or coils fit into coil grooves 114. Injection port 115 is positioned midway along the mold fixtures, however, more than one injection port can be used to insure that the flow of polymer is uniform and consistent. Preferably, silicone rubber is injected into the molds so that the silicone rubber flows over the undulating strands and the electrodes or the coils. When the cardiac harness assembly is taken out of the mold, the undulating strands will be attached to the electrodes or the coils by the silicone rubber according to the pattern shown. Other patterns may be desired and the molds are easily altered to provide any pattern that ensures a secure attachment between the undulating strands and the electrodes or the coils. Importantly, the molds of FIGS. 18 and 19 can be used to inject the dielectric material or silicone rubber inside the coils and, if necessary, between the gaps in the coils in order to insure that the coils and the undulating strands are insulated from each other. The silicone rubber fills the inside of the coils, extrudes through the gaps in the coils, and forms a skin on the inner and outer surface of the coil. This skin is selectively removed (as will be described) to expose portions of the electrode coils so that they can conduct current as described. Further, it is desired that the coils and the undulating strands do not overlap or touch in order to reduce any frictional engagement between the metallic coils and the metallic undulating strands. In order to increase the frictional engagement between the cardiac harness and the epicardial surface of the heart, small projections (not shown) can be molded along the surface of the coils that will contact the epicardial surface. As previously described with respect to the grip pads, these small projections, preferably formed of silicone rubber, will engage the epicardial surface of the heart and increase the frictional engagement between the coils and the surface of the heart in order to secure the harness to the heart without the use of sutures, clips, or other mechanical attachment means.

In further keeping with the invention, as shown in FIGS. 20–23, a portion of a lead having an electrode 120 is shown in the form of a conductive coil 121. The coil can be formed of any suitable wire that is conductive so that an electrical shock can be transmitted through the electrode and through the myocardium of the heart. In this embodiment, the coil wire is wrapped around a dielectric material 122 in a helical configuration, however, a spiral wrap or other configuration is possible as long as the coil has superior fatigue resistance and longitudinal flexibility. Importantly, conductive coils 121 have high fatigue resistance which is necessary since the coil is on or near the surface of the beating heart so that the coil is constantly flexing along its longitudinal length in response to heart expansion and contraction. The cross-section of the wire preferably is round or circular, however, it also can be oval shaped or flat (rectangular) in order to reduce the profile of the electrode for minimally invasive delivery. A circular, oval or flat wire will have a relatively high fatigue resistance as well as a relatively low profile for delivery purposes. Also, a flat wire coil is highly flexible along the longitudinal axis and it has a relatively high surface area for delivering an electrical shock. The electrode 120 has a first surface 123 and a second surface 124. The first surface 123 will be proximate the epicardial surface of the heart, or other portions of the heart, while the second surface will be opposite the first surface and away from the epicardial surface of the heart. A conductive wire (not shown) extends through the dielectric material 122 and attaches to the coil wire 121 at one or more locations along the coil or coils, and the conductive wire is connected to a power source (e.g., an ICD) at its other end. As shown in FIG. 22, the cross-section of the electrode 120 can be circular, or as shown in FIG. 23, can be oval for reduced profile for minimally invasive delivery. Other cross-sectional shapes for electrode 120 are available depending upon the particular need. All of these cross-sectional shapes will have relatively high fatigue resistance. As shown in FIGS. 22 and 23, multiple lumens 125 can be provided to carry one or more conductive wires from the electrode to the power source (pulse generator, ICD, CRT-D, pacemaker, etc.). The lumens also can carry sensing wires that transmit data from a sensor on or in the heart to a pacemaker so that the heart can be monitored. Further, the lumens 125 can be used for other purposes such as drug delivery (therapeutic drugs, steroids, etc.), dye injection for visability under fluoroscopy, carrying a guide wire (not shown) or a stylet to facilitate delivery of the electrodes and the harness, or for other purposes. The lumens 125 can be used to carry a guide wire (not shown) or a stylet in such a way that the column stiffness of the coil is increased by the guide wire or stylet, or in a manner that will vary the column stiffness as required. By varying the column stiffness of the coils with a guide wire or a stylet in lumens 125, the ability to push the cardiac harness over the heart (as will be described) will be enhanced. The guide wires or stylets also can be used, to some extent, to steer the coils and hence the cardiac harness during delivery and implantation over the heart. The guide wire or stylet in lumens 125 can be removed after the cardiac harness is implanted so that the coils (electrodes) become more flexible and atraumatic.

In keeping with the invention, as shown in FIGS. 20–23, the electrode 120 not only provides an electrical conduit for use in defibrillation, but also has sufficient column strength when attached to the cardiac harness to assist in the delivery of the harness by minimally invasive means. As will be further described, the coils 121 provide a highly flexible electrode along its longitudinal length, and also provide a substantial amount of column strength when coupled with a cardiac harness to assist in the delivery of the harness.

In further keeping with the invention of FIGS. 20–23, a dielectric material such as silicone rubber 126 can be used to coat electrodes 120. During the molding process (previously described), when the electrode 120 is attached to the cardiac harness, silicone rubber 126 will coat the entire electrode 120. Soda blasting (or other known material removal process) can be used to remove portions of the silicone rubber skin from the coils 121 in order to expose first surface 123 and second surface 124 (or portions of those surfaces) so that the bare metal coil is exposed to the epicardial surface of the heart. Preferably, the silicone rubber is removed from both the first surface and the second surface, however, it also may be advantageous to remove the silicone rubber from only the first surface, which is proximate to or in contact with the epicardial surface of the heart. The electrode 120 has a surface area 128 which essentially includes all of the bare metal surface area that is exposed and that will deliver a shock. The amount of surface area per electrode can vary greatly depending upon a particular application, however, surface areas in the range from about 50 mm2 to about 600 mm2 are typical. While it is possible to remove the silicone rubber from only the second surface (facing away from the heart), and leaving the first surface coated with silicone rubber, an electrical shock can still be delivered from the bare metal second surface, however, the electrical shock delivered may not be as efficient as with other embodiments. While the dimensions of the electrodes can vary widely due to the variations in the size of the heart to be treated in conjunction with the size of the cardiac harness, generally the length of the electrode ranges from about 2 cm to about 16 cm. The coil 121 has a length in the range of about 1 cm to about 12 cm. Commercially available leads having one or more electrodes are available from several sources and may be used with the cardiac harness of the present invention. Commercially available leads with one or more electrodes is available from Guidant Corporation (St. Paul, Minn.), St. Jude Medical (Minneapolis, Minn.) and Medtronic Corporation (Minneapolis, Minn.). Further examples of commercially available cardiac rhythm management devices, including defibrillation and pacing systems available for use in combination with the cardiac harness of the present invention (possibly with some modification) include, the CONTAK CD®, the INSIGNIA® Plus pacemaker and FLEXTREND® leads, and the VITALITY™ AVT® ICD and ENDOTAK RELIANCE® defibrillation leads, all available from Guidant Corporation (St. Paul, Minn.), and the InSync System available from Medtronic Corporation (Minneapolis, Minn.).

In an alternative embodiment, as shown in FIG. 24, the conductive coils 121 need not be continuous along the length of the electrode 120, but can be spatially isolated or staggered along the electrode. For example, multiple coil sections 127, similar to the coil 121 shown in FIG. 20, can be spaced along the electrode with each coil section being attached to the conductive wire so it receives electrical current from the power source. The coil sections can be from about 0.5 cm to about 2.0 cm long and be spaced from about 0.5 cm to about 4 cm apart along the electrode. The dimensions used herein are by way of example only and can vary to suit a particular application.

When removing portions of the silicone rubber from the electrode 120 using soda blasting or a similar technique, it may be desirable to leave portions of the electrode masked or insulated so that the masked portion is non-conductive. By masking portions of two electrodes positioned, for example, on opposite sides of the left ventricle, it is possible to vector a shock at a desirable angle through the myocardium and ventricle. The shock will travel from the bare metal (unmasked) portion of one electrode through the myocardium and the ventricle to the bare metal (unmasked)

portion of the opposing electrode at a vector angle determined by the position of the masking on the electrodes.

The cardiac rhythm management devices associated with the present invention are implantable devices that provide electrical stimulation to selected chambers of the heart in order to treat disorders of cardiac rhythm and can include pacemakers and implantable cardioverter/defibrillators and/or cardiac resynchronization therapy devices (CRT-D). A pacemaker is a cardiac rhythm management device which paces the heart with timed pacing pulses. As previously described, common conditions for which pacemakers are used is in the treatment of bradycardia (ventricular rate is too slow) and tachycardia (cardiac rhythms are too fast). As used herein, a pacemaker is any cardiac rhythm management device with a pacing functionality, regardless of any other functions it may perform such as the delivery of cardioversion or defibrillation shocks to terminate atrial or ventricular fibrillation. An important feature of the present invention is to provide a cardiac harness having the capability of providing a pacing function in order to treat the synchrony of both ventricles. To accomplish the objective, a pacemaker with associated leads and electrodes are associated with and incorporated into the cardiac harness of the present invention. The pacing/sensing electrodes, alone or in combination with defibrillating electrodes, provide treatment to synchronize the ventricles and improve cardiac function.

Figure 25A:
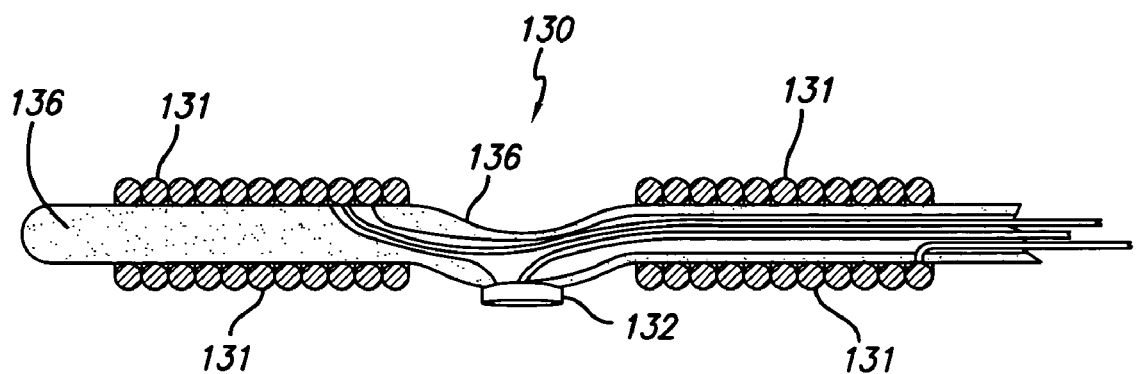
FIG. 25A depicts a side view of a portion of a defibrillator electrode combined with a pacing/sensing electrode.
Figure 25B:
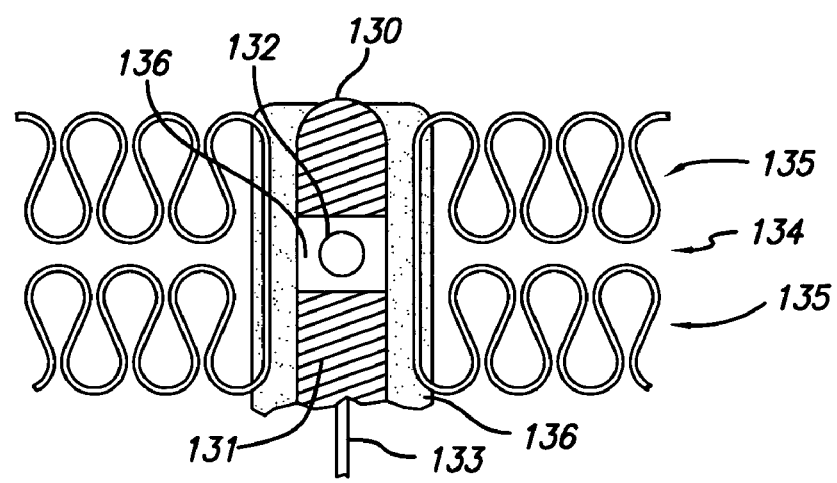
FIG. 25B depicts a top view of the electrode portion of FIG. 25A.

In keeping with the invention, a pacemaker and a pacing/sensing electrode are incorporated into the design of the cardiac harness. As shown in FIGS. 25A and 25B, a lead (not shown) having a defibrillator electrode 130 at its distal end, shown in partial section, not only incorporates wire coils 131 used to deliver a defibrillating electrical shock to the epicardial surface of the heart, but also incorporates a pacing/sensing electrode 132. The defibrillator electrode 130 can be attached to any cardiac harness embodiment previously described herein. In this embodiment, a non-penetrating pacing/sensing electrode 132 is combined with the defibrillating electrode 130 in order to provide data relating to heart function. More specifically, the pacing/sensing electrode 132 does not penetrate the myocardium in this embodiment, however, it may be beneficial in other embodiments for the pacing or sensing electrode to penetrate the myocardium. One advantage of a non-penetrating pacing/sensing electrode is that there is no danger of puncturing a coronary artery or causing further trauma to the epicardium or myocardium. It is also easier to design since there is no requirement of a penetration mechanism (barb or screw) on the pacing/sensing electrode. The pacing/sensing electrode 132 is in direct contact with the epicardial surface of the heart and will provide data via lead wire 133 to the pulse generator (pacemaker), which will interpret the data and provide any pacing function necessary to achieve, for example, ventricular resynchronization therapy, left ventricular pacing, right ventricular pacing, synchrony of both ventricles, and/or biventricular pacing. As shown in FIG. 25B, the pacing/sensing electrode 132 is incorporated into a portion of a cardiac harness 134, and more particularly the undulating strands 135 are attached by dielectric material 136 to the pacing/sensing electrode. As can be seen in FIGS. 25A and 25B, the wire coils 131 of the defibrillating electrode 130 are wrapped around the dielectric material 136, and the dielectric material insulates the pacing/sensing electrode 132 from both the wire coils 131 and from the undulating strands 135 of the cardiac harness. Multiple pacing/sensing electrodes 132 can be incorporated along defibrillating electrode 130, and multiple pacing and sensing electrodes can be incorporated on other electrodes associated with the cardiac harness.

In one of the preferred embodiments, multi-site pacing (as previously shown in FIGS. 8A–8D) using pacing/sensing electrodes 132 enables resynchronization therapy in order to treat the synchrony of both ventricles. Multi-site pacing allows the positioning of the pacing/sensing electrodes to provide bi-ventricular pacing or right ventricular pacing, left ventricular pacing, depending upon the patient's needs.

Figure 26A:
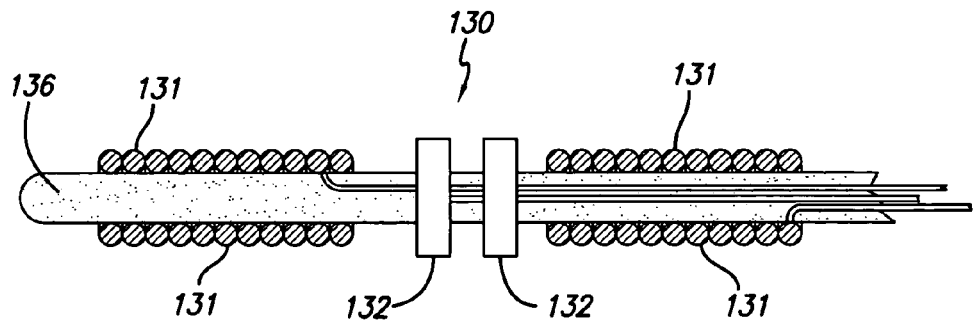
FIGS. 26A–26C depict various views of a defibrillator electrode combined with a pacing/sensing electrode.
Figure 26B:
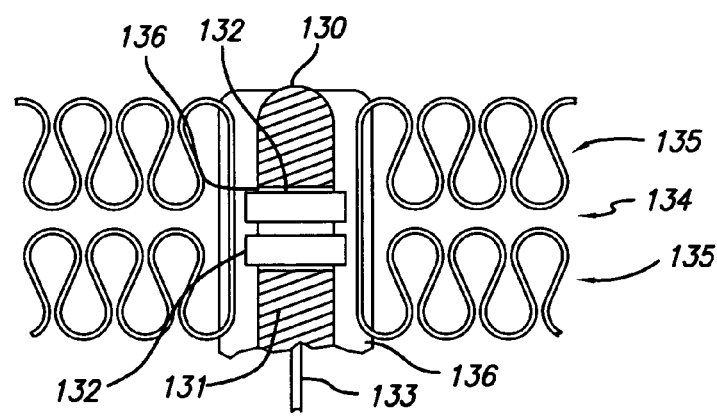
Figure 26C:
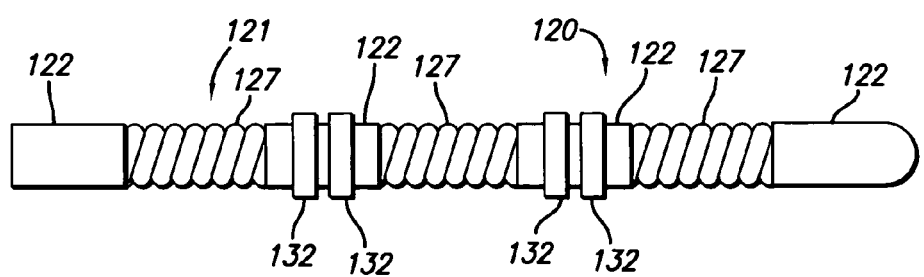

In another embodiment, shown in FIGS. 26A–26C, a defibrillating electrode is combined with pacing/sensing electrodes, for attachment to any of the cardiac harness embodiments disclosed herein. In this embodiment, the defibrillating electrode 130 is formed of wire coils 131 wrapped in a helical manner. The helical wire can be a wound wire having a single strand or a quadrafilar wire having four wires bundled together to form the coil. The wire coils 131 are wrapped around dielectric material 136 in a manner similar to that described for the embodiments in FIGS. 25A and 25B. In this embodiment, the pacing/sensing electrode 132 is in the form of a single ring for unipolar operation, and two rings for bi-polar operation. The pacing/sensing electrode rings 132 are mounted coaxially with the defibrillating electrode wire coils 131, and the conducting wires from the wire coils and the pacing/sensing ring electrode are shown extending through the dielectric material 136 and being insulated from each other. The conducting wires from the defibrillating electrode 130 and from the pacing/sensing ring electrodes 132 can be bundled into a common lead wire 133 which extends to the pulse generator (an ICD, CRT-D, and/or a pacemaker). As can be seen in FIGS. 26A–26C, the pacing/sensing electrode rings 132 have a diameter that is somewhat larger than the defibrillator electrode coils 131 in order to insure preferential contact by the electrode rings against the epicardial surface of the heart. Preferably, several pairs of pacing/sensing electrode rings (bipolar) would be positioned on the cardiac harness and be positioned to come into contact with, for example, the left ventricle free wall. Multi-site pacing allows the pacing/sensing electrode rings 132 to be used for both pacing and resynchronization concurrently. Further, the pacing/sensing electrode rings 132 also can be used in the absence of defibrillating electrodes 130. The prior disclosure relating to molding of the cardiac harness to the defibrillator electrode applies equally as well to the pacing/sensing electrode rings. The wire coil 131 and the pacing/sensing electrode rings 32 can be fabricated in several ways including by laser cutting stainless steel tubing or using highly conductive materials in wire form, such as biocompatible platinum wire. As previously disclosed, the wire coils 131 can be quadrafilar wire (platinum) for improved flexibility and conformability to the epicardial surface of the heart and be biocompatible. The surface of the pacing/sensing electrodes can vary greatly depending upon the application. As an example, in one embodiment, the surface area of the pacing/sensing electrodes are in the range from about 2 mm2 to about 12 mm2, however, this range can vary substantially. While the disclosed embodiments show the pacing/sensing electrodes combined with the defibrillating electrodes, the pacing/sensing electrodes can be formed separately and mounted on the cardiac harness with or without defibrillating electrodes.

The defibrillating electrode 130 as disclosed herein, can be used with commercially available pacing/sensing electrodes and leads. For example, Oscor (Model HT 52PB) endocardial/passive fixation leads can be integrated with the defibrillator electrode 130 by molding the leads into the fibrillator electrode using the same molds previously disclosed herein.

The foregoing disclosed invention incorporating cardiac rhythm management devices into the cardiac harness combines several treatment modalities that are particularly beneficial to patients suffering from congestive heart failure. The cardiac harness provides a compressive force on the heart thereby relieving wall stress, and improving cardiac function. The defibrillating and pacing/sensing electrodes associated with the cardiac harness, along with ICD's and pacemakers, provide numerous treatment options to correct for any number of maladies associated with congestive heart failure. In addition to the defibrillation function previously described, the cardiac rhythm devices can provide electrical pacing stimulation to one or more of the heart chambers to improve the coordination of atrial and/or ventricular contractions, which is referred to as resynchronization therapy. Cardiac resynchronization therapy is pacing stimulation applied to one or more heart chambers, typically the ventricles, in a manner that restores or maintains synchronized bilateral contractions of the atria and/or ventricles thereby improving pumping efficiency. Resynchronization pacing may involve pacing both ventricles in accordance with a synchronized pacing mode. For example, pacing at more than one site (multi-site pacing) at various sites on the epicardial surface of the heart to desynchronize the contraction sequence of a ventricle (or ventricles) may be therapeutic in patients with hypertrophic obstructive cardiomyopathy, where creating asynchronous contractions with multi-site pacing reduces the abnormal hyper-contractile function of the ventricle. Further, resynchronization therapy may be implemented by adding synchronized pacing to the bradycardia pacing mode where paces are delivered to one or more synchronized pacing sites in a defined time relation to one or more sensing and pacing events. An example of synchronized chamber-only pacing is left ventricle only synchronized pacing where the rate in synchronized chambers are the right and left ventricles respectively. Left-ventricle-only pacing may be advantageous where the conduction velocities within the ventricles are such that pacing only the left ventricle results in a more coordinated contraction by the ventricles than by conventional right ventricle pacing or by ventricular pacing. Further, synchronized pacing may be applied to multiple sites of a single chamber, such as the left ventricle, the right ventricle, or both ventricles. The pacemakers associated with the present invention are typically implanted subcutaneously on a patient's chest and have leads threaded to the pacing/electrodes as previously described in order to connect the pacemaker to the electrodes for sensing and pacing. The pacemakers sense intrinsic cardiac electrical activity through the electrodes disposed on the surface of the heart. Pacemakers are well known in the art and any commercially available pacemaker or combination defibrillator/pacemaker can be used in accordance with the present invention.

The cardiac harness and the associated cardiac rhythm management device system of the present invention can be designed to provide left ventricular pacing. In left heart pacing, there is an initial detection of a spontaneous signal, and upon sensing the mechanical contraction of the right and left ventricles. In a heart with normal right heart function, the right mechanical atrio-ventricular delay is monitored to provide the timing between the initial sensing of right atrial activation (known as the P-wave) and right ventricular mechanical contraction. The left heart is controlled to provide pacing which results in left ventricular mechanical contraction in a desired time relation to the right mechanical contraction, e.g., either simultaneously or just preceding the right mechanical contraction. Cardiac output is monitored by impedance measurements and left ventricular pacing is timed to maximize cardiac output. The proper positioning of the pacing/sensing electrodes disclosed herein provides the necessary sensing functions and the resulting pacing therapy associated with left ventricular pacing.

An important feature of the present invention is the minimally invasive delivery of the cardiac harness and the cardiac rhythm management device system which will be described immediately below.

Delivery of the cardiac harness 20,60, and 100 and associated electrodes and leads can be accomplished through conventional cardio-thoracic surgical techniques such as through a median sternotomy. In such a procedure, an incision is made in the pericardial sac and the cardiac harness can be advanced over the apex of the heart and along the epicardial surface of the heart simply by pushing it on by hand. The intact pericardium is over the harness and helps to hold it in place. The previously described grip pads and the compressive force of the cardiac harness on the heart provide sufficient attachment means of the cardiac harness to the epicardial surface so that sutures, clips or staples are unnecessary. Other procedures to gain access to the epicardial surface of the heart include making a slit in the pericardium and leaving it open, making a slit and later closing it, or making a small incision in the pericardium.

Figure 27:
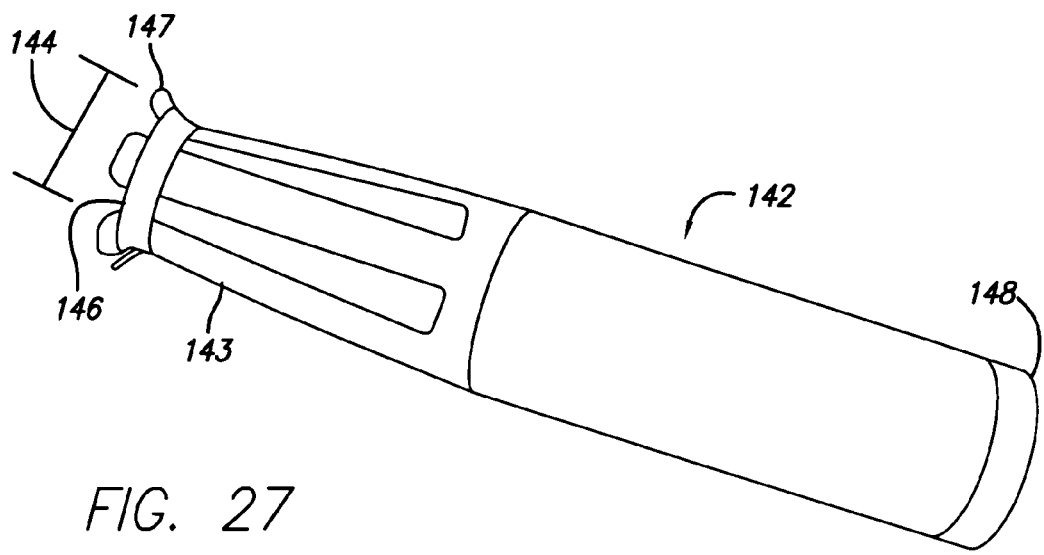
FIG. 27 depicts a side view of an introducer for delivering the cardiac harness through minimally invasive procedures.
Figure 28:
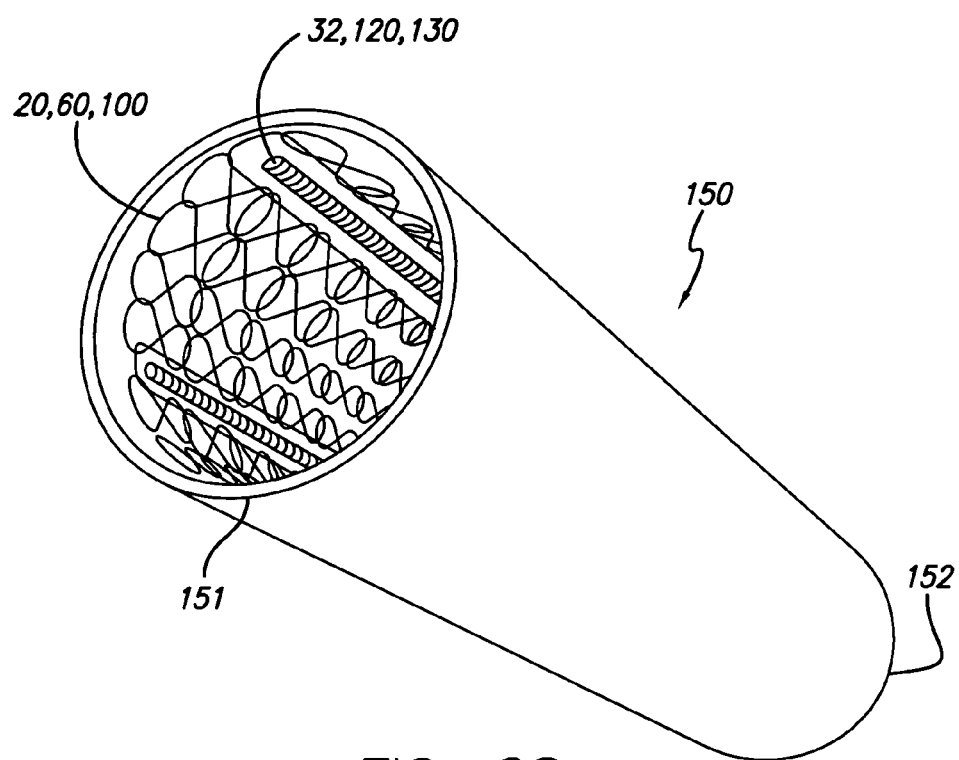
FIG. 28 depicts a perspective end view of a dilator with the cardiac harness releasably positioned therein.
Figure 29:
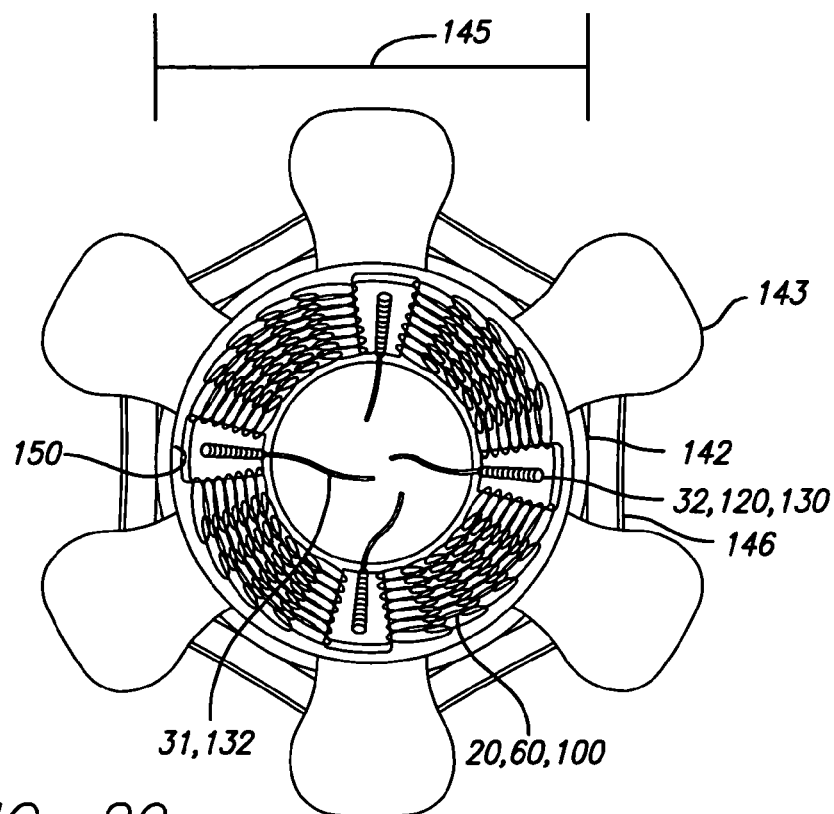
FIG. 29 depicts an end view of the introducer with the cardiac harness releasably positioned therein.
Figure 30:
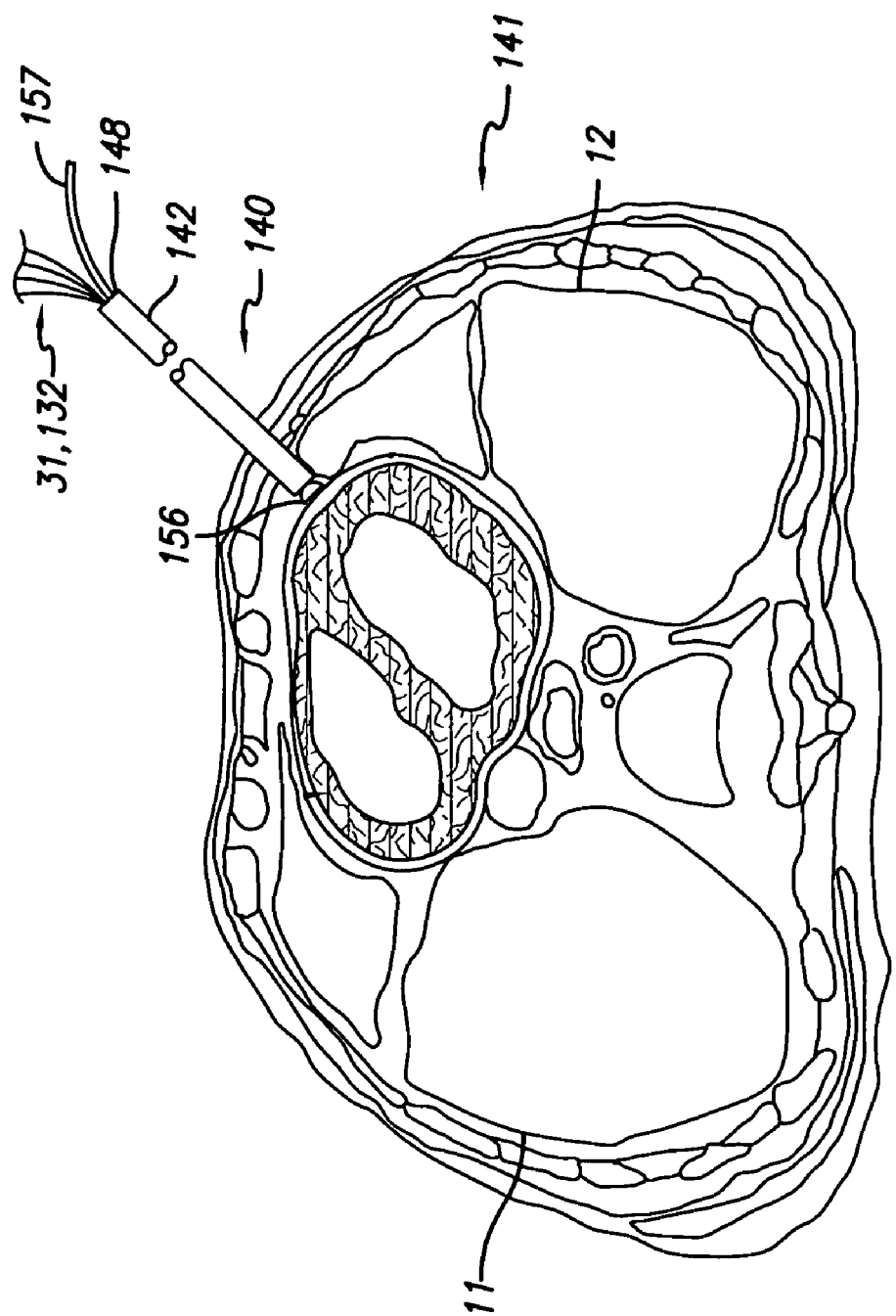
FIG. 30 depicts a schematic cross-sectional view of a human thorax with the cardiac harness system being delivered by a delivery device inserted through an intercostal space and contacting the heart.
Figure 32:
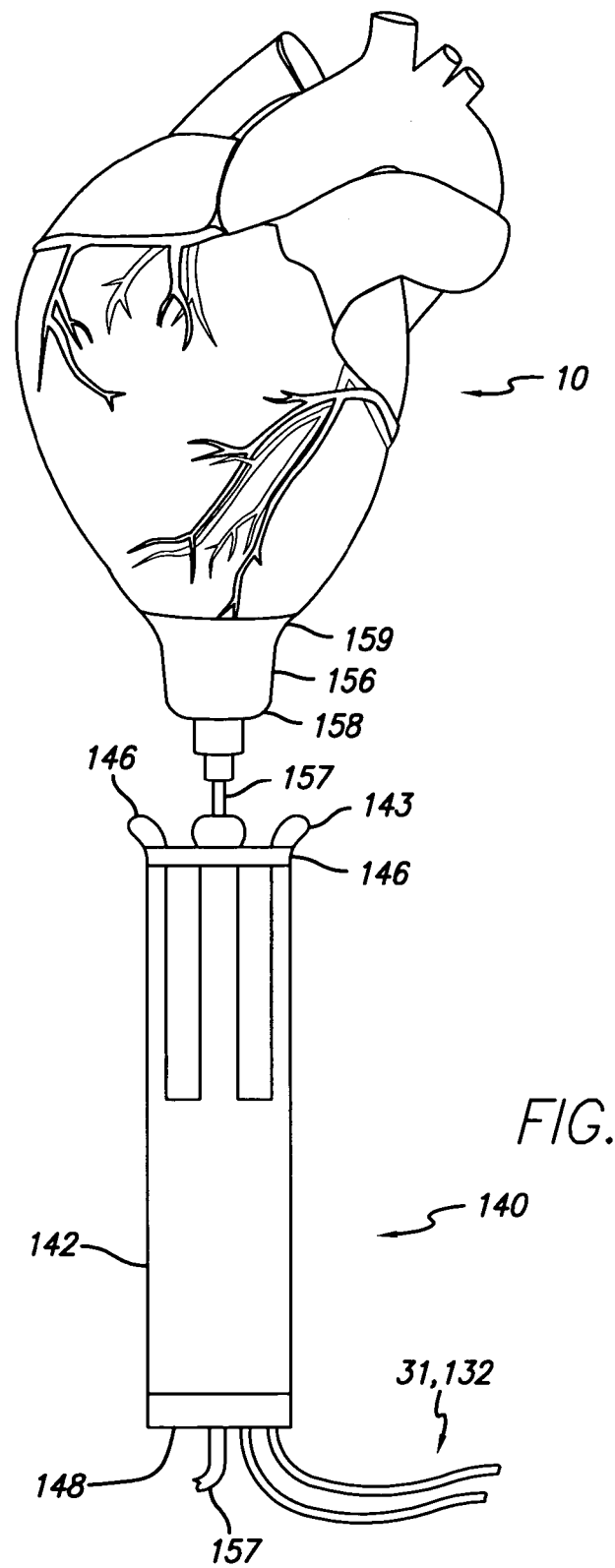
FIG. 32 depicts a plan view of the heart with the suction device attached to the apex and the introducer positioned to deliver the cardiac harness over the heart.
Figure 33:
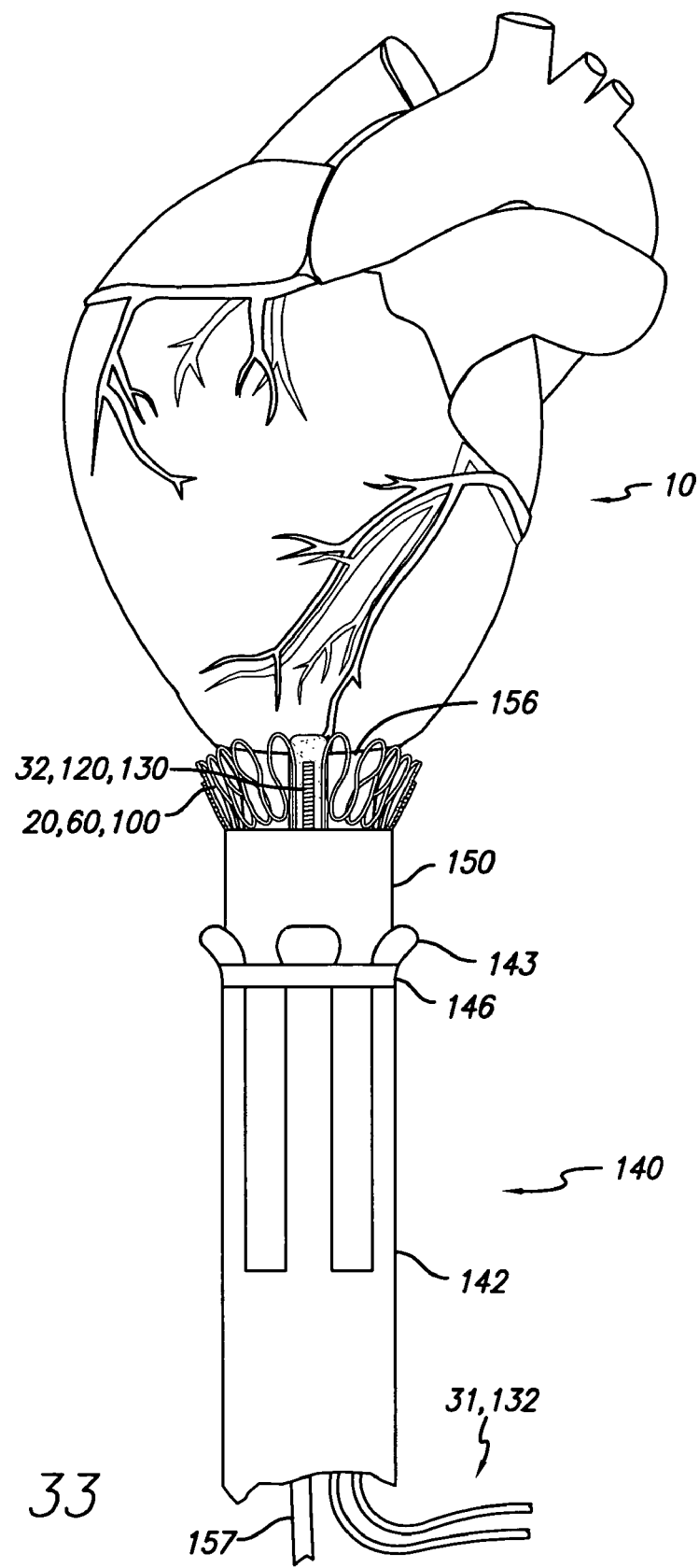
FIG. 33 depicts a plan view of the cardiac harness being deployed from the introducer onto the epicardial surface of the heart.
Figure 34:
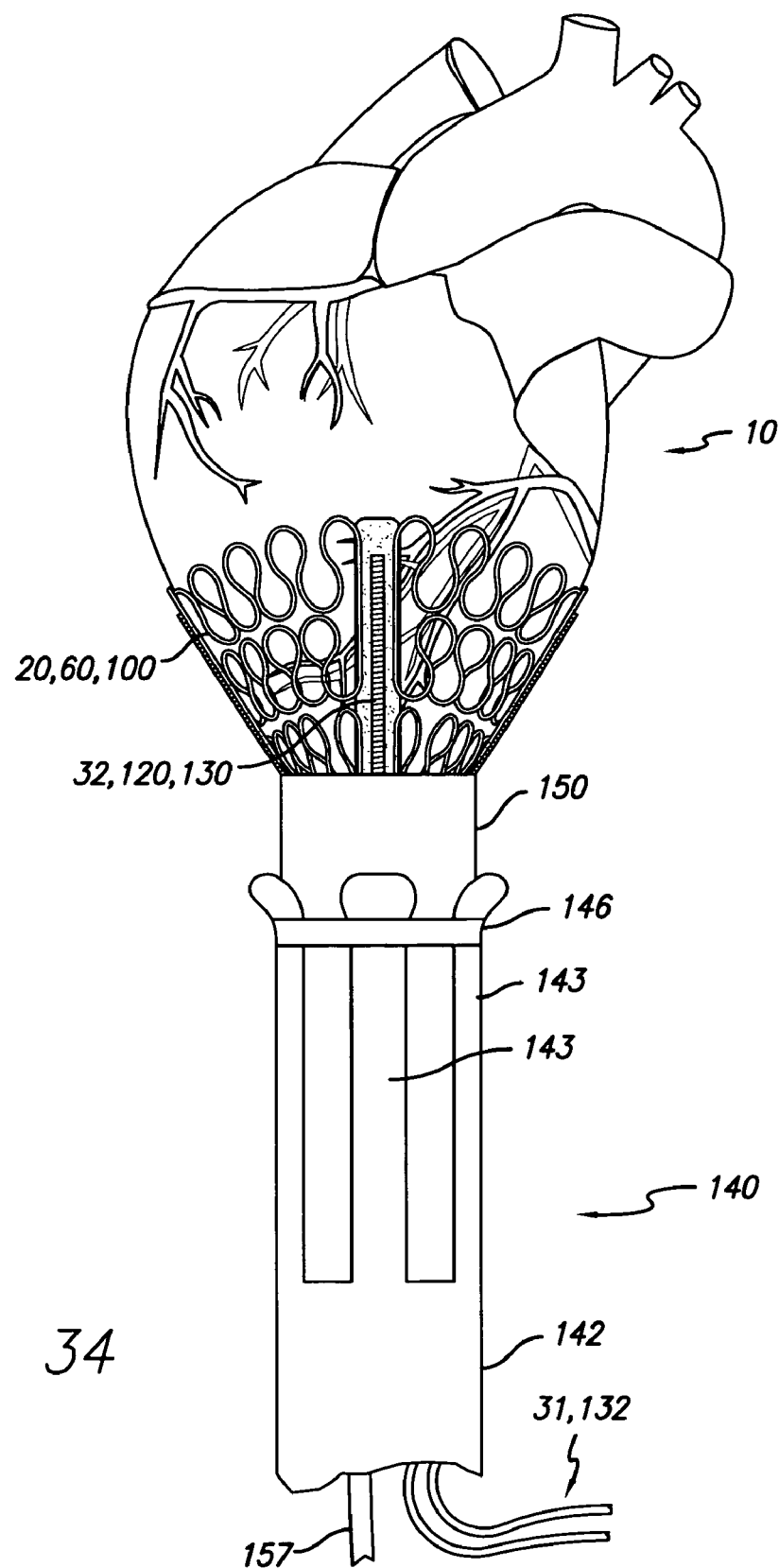
FIG. 34 depicts a plan view of the heart with the cardiac harness being deployed from the introducer onto the epicardial surface of the heart.

Preferably, however, the cardiac harness and associated electrodes and leads may be delivered through minimally invasive surgical access to the thoracic cavity, as illustrated in FIGS. 27–36, and more specifically as shown in FIG. 30. A delivery device 140 may be delivered into the thoracic cavity 141 between the patient's ribs to gain direct access to the heart 10. Preferably, such a minimally invasive procedure is accomplished on a beating heart, without the use of cardio-pulmonary bypass. Access to the heart can be created with conventional surgical approaches. For example, the pericardium may be opened completely or a small incision can be made in the pericardium (pericardiotomy) to allow the delivery system 140 access to the heart. The delivery system of the disclosed embodiments comprises several components as shown in FIGS. 27–36. As shown in FIG. 27, an introducer tube 142 is configured for low profile access through a patient's ribs. A number of fingers 143 are flexible and have a delivery diameter 144 as shown in FIG. 27, and an expanded diameter 145 as shown in FIG. 29. The delivery diameter is smaller than the expanded diameter. An elastic band 146 expands around the distal end 147 of the fingers and prevents the fingers from overexpanding during delivery of the cardiac harness. The distal end of the fingers is the part of the delivery device 140 that is inserted through the patient's ribs to gain direct access to the heart.

The delivery device 140 also includes a dilator tube 150 that has a distal end 151 and a proximal end 152. The cardiac harness 20,60,100 is collapsed to a low profile configuration and inserted into the distal end of the dilator tube, as shown in FIG. 28. The dilator tube has an outside diameter that is slightly smaller than the inside diameter of the introducer tube 142. As will be discussed more fully herein, the distal end 151 of the dilator tube is inserted into the proximal end 147 of the introducer tube in close sliding engagement and in a slight frictional engagement. The slidable engagement between the dilator tube and the introducer tube should be with some mild resistance, however, there should be unrestricted slidable movement between the two tubes. The distal end 151 of the dilator tube will expand the fingers 143 of the introducer tube 142 as the dilator tube is pushed distally into the introducer tube as shown in FIG. 29. In the embodiments shown in FIGS. 27–36, the cardiac harness 20,60,100 is equipped with leads (previously described) having electrodes for use in defibrillation or pacing functions.

Figure 31:
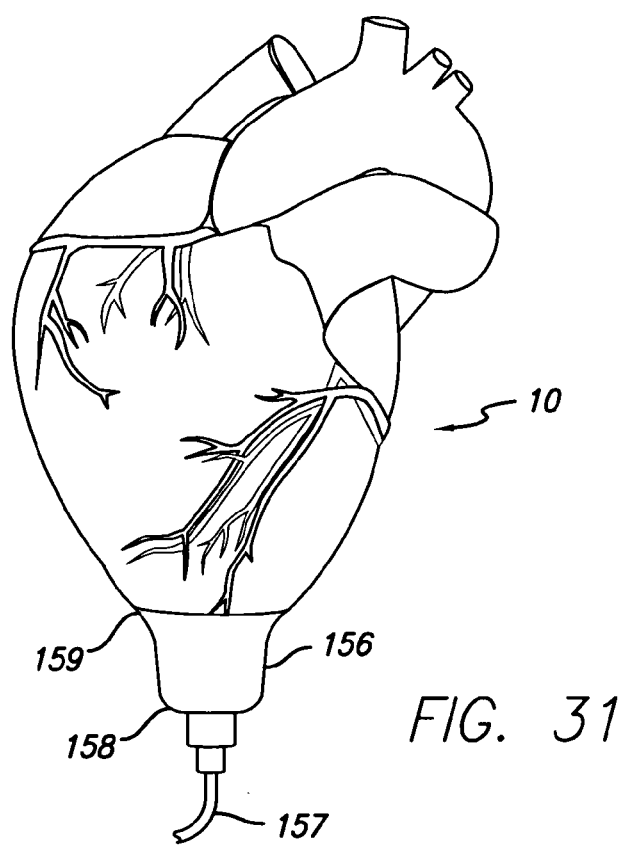
FIG. 31 depicts a plan view of the heart with a suction device releasably attached to the apex of the heart.

As shown in FIG. 31, the delivery system 140 also includes a releasable suction device, such as suction cup 156 at the distal end of the delivery device. The negative pressure suction cup 156 is used to hold the apex of the heart 10. Negative pressure can be applied to the suction cup using a syringe or other vacuum device commonly known in the art. A negative pressure lock can be achieved by a one-way valve stop-cock or a tubing clamp, also known in the art. The suction cup 156 is formed of a biocompatible material and is preferably stiff enough to prevent any negative pressure loss through the heart while manipulating the heart and sliding the cardiac harness 20,60,100 onto the heart. Further, the suction cup 156 can be used to lift and maneuver the heart 10 to facilitate advancement of the harness or to allow visualization and surgical manipulation of the posterior side of the heart. The suction cup has enough negative pressure to allow a slight pulling in the proximal direction away from the apex of the heart to somewhat elongate the heart (e.g., into a bullet shape) during delivery to facilitate advancing the cardiac harness over the apex and onto the base portion of the heart. After the suction cup 156 is attached to the apex of the heart and a negative pressure is drawn, the cardiac harness, which has been releasably mounted in the distal end 151 of the dilator tube 150, can be advanced distally over the heart, as will be described more fully herein.

As shown in FIG. 30, the delivery device 140, and more specifically introducer tube 142, has been advanced through the intercostal space between the patient's ribs during insertion of the introducer tube, the fingers 143 are in their delivery diameter 144, which is a low profile for ease of access through the small port made through the patient's ribs. Thereafter, the dilator tube 150, with the cardiac harness 20,60,100 mounted therein, is advanced distally through the introducer tube so that the fingers 143 are expanded until they achieve their expanded diameter 145. The suction cup 156 can be attached to the apex 13 of the heart 10 either before or after the dilator tube is advanced to spread the fingers 143 of the introducer tube 142. Preferably, the dilator tube has already expanded the fingers on the introducer tube so that there is a larger opening for the suction cup as it is advanced through the inside of a dilator tube, out of the distal end of the introducer tube, and placed in contact with the apex of the heart. Thereafter, a negative pressure is drawn allowing the suction cup to securely attach to the apex of the heart. Visualizing equipment that is commonly known in the art may be used to assist in positioning the suction cup to the apex. For example, fluoroscopy, magnetic resonance imaging (MRI), dye injection to enhance fluoroscopy, and echocardiography, and intracardiac, transesophageal, or transthoracic echo, all can be used to enhance positioning and in attaching the suction cup to the apex of the heart. After negative pressure is drawn and the suction cup is securely attached (releasably) to the apex of the heart, the heart can then be maneuvered somewhat by pulling on the tubing 157 attached to the suction cup, or by manipulating the introducer tube 142, the dilator tube 150, both in conjunction with the suction cup. As previously described, it may be advantageous to pull on the tubing 157 to allow the suction cup to pull on the apex of the heart and elongate the heart somewhat in order to facilitate sliding the harness over the epicardium.

Figure 35:
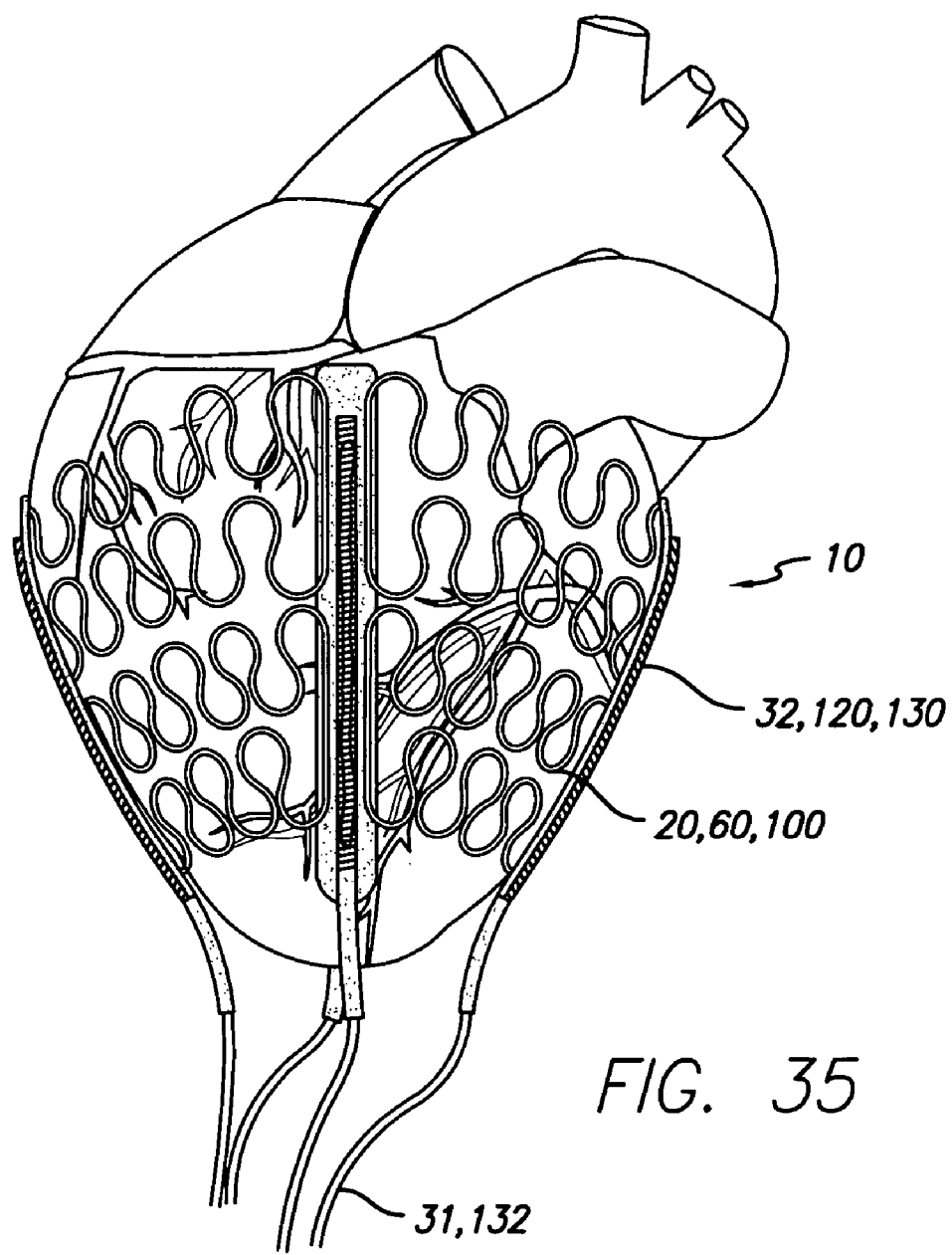
FIG. 35 depicts a plan view of the heart with the cardiac harness having electrodes attached thereto, surrounding a portion of the heart.
Figure 36:
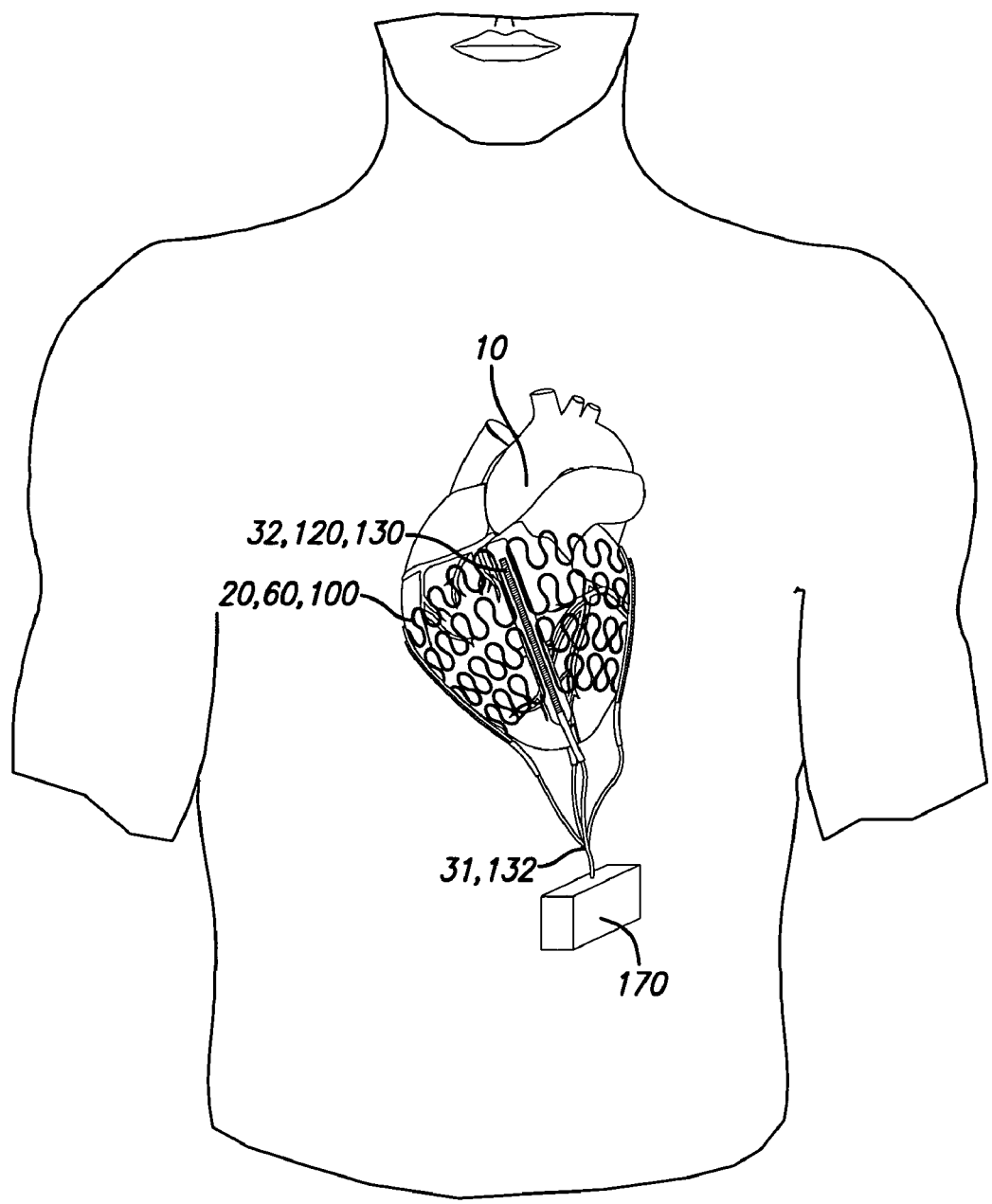
FIG. 36 depicts a schematic view of the cardiac harness assembly mounted on the human heart together with leads and an ICD for use in defibrillation or pacing.

As more clearly shown in FIGS. 32–36, the cardiac harness 20,60,100 is advanced distally out of the dilator tube and over the suction cup 156. The suction cup is tapered so that the distal end of the harness slides over the narrow portion of the taper (the proximal end of the suction cup 158). The suction cup becomes wider at its distal end where it is attached to the apex of the heart, and the cardiac harness continues to slide and expand over the suction cup as it is advanced distally. As the cardiac harness continues to be advanced distally, it slides over the apex of the heart and continues to expand as it is pushed out of the dilator tube and along the epicardial surface of the heart. Since the harness and the electrodes 32,120,130 are coated with the previously described dielectric material, preferably silicone rubber, the cardiac harness should slide easily over the epicardial surface of the heart. The silicone rubber offers little resistance and the epicardial surface of the heart has sufficient fluid to allow the harness to easily slide over the wet surface of the heart. The pericardium previously has been cut so that the cardiac harness is sliding over the epicardial surface of the heart with the pericardium over the cardiac harness to help hold it onto the surface of the heart. As shown in FIGS. 35 and 36, the cardiac harness 20,60,100 has been completely advanced out of the dilator tube so that the harness covers at least a portion of the heart 10. The suction cup 156 has been withdrawn, and the introducer tube 142 and dilator tube 150 also have been withdrawn proximally from the patient. Prior to removing the introducer tube, a power source 170 (such as an ICD, CRT-D, and/or pacemaker) can be implanted by conventional means. The electrodes will be attached to the pulse generator to provide a defibrillating shock or pacing functions as previously described.

In the embodiments shown in FIGS. 27–36, the cardiac harness 20,60,100 was advanced through the dilator tube by pushing on the proximal end of the electrodes 32,120,130, on the lead wires 31,133, and on the proximal end (apex 26) of the cardiac harness. Even though the electrodes are designed to be atraumatic and longitudinally flexible, the electrodes have sufficient column strength so that pushing on the proximal ends of the electrodes assists in pushing the cardiac harness out of the dilator tube and over the epicardial surface of the heart. In one embodiment, advancement of the cardiac harness is accomplished by hand, by the physician simply pushing on the electrodes and the leads to advance the cardiac harness out of the dilator tube to slide onto the epicardial surface of the heart.

As shown in the embodiments of FIGS. 27–36, the delivery device 140, and more specifically introducer tube 142 and dilator tube 150, have a circular cross-section. It may be preferable, however, to chose other cross-sectional shapes, such as an oval cross-sectional shape for the delivery device. An oval delivery device may be more easily inserted through the intercostal space between the patient's ribs for a low profile delivery. Further, as the cardiac harness 20,60,100 is advanced out of a delivery device 140 having an oval cross-section, the harness distal end will quickly form into a more circular shape in order to assume the configuration of the epicardial surface of the heart as it is advanced distally over the heart.

In the embodiments shown in FIGS. 35 and 36, the cardiac harness 20,60,100 remains firmly attached to the epicardial surface of the heart without the need for any further attachment means, such as sutures, clips, adhesives, or staples. Further, the pericardial sac helps to enclose the harness to prevent it from shifting or sliding on the epicardial surface of the heart.

Importantly, during delivery of the cardiac harness 20,60, 100, the harness itself, the electrodes 32,120,130, as well as leads 31 and 132 have sufficient column strength in order for the physician to push from the proximal end of the harness to advance it distally through the dilator tube 150. While the entire cardiac harness assembly is flexible, there is sufficient column strength, especially in the electrodes, to easily slide the cardiac harness over the epicardial surface of the heart in the manner described.

In an alternative embodiment, if the cardiac harness 20,60,100 includes coils 72, as opposed to the electrodes and leads, the harness can be delivered in the same manner as previously described with respect to FIGS. 27–36. The coils have sufficient column strength to permit the physician to push on the proximal end of the coils to advance the cardiac harness distally to slide over the apex of the heart and onto the epicardial surface.

In another embodiment, delivery of the cardiac harness 20,60,100 can be by mechanical means as opposed to the hand delivery previously described. As shown in FIGS. 37–42, delivery system 180 includes an introducer tube 181 that functions the same as introducer tube 142. Also, a dilator tube 182, which is sized for slidable movement within the introducer tube, also functions the same as the previously described dilator tube 150. An ejection tube 183 is sized for slidable movement within the dilator tube, that is, the outer diameter of the ejection tube is slightly smaller than the inner diameter of the dilator tube. As shown in FIGS. 40 and 41, the ejection tube has a distal end 184 and a proximal end 185, wherein the distal end of the ejection tube has a plate that fills the entire inner diameter of the ejection tube. The plate has a number of lumens 187 for receiving leads 31,132 and for receiving the suction cup 156 and associated tubing 157. Thus, lumens 188 are sized for receiving leads 31,132 therethrough, while lumen 189 is sized for receiving suction cup 156 and the associated tubing 157. The number of lumens 188 in plate 186 will be defined by the number of leads 31,132 associated with the cardiac harness 20,60,100. Thus, as shown in FIG. 40, there are four lumens 188 for receiving four leads therethrough, and one lumen 189 for receiving the suction cup 156 and tubing 157 therethrough. The leads and the tubing 157 extend proximally out the proximal end 185 of the ejection tube. As shown in FIG. 42, the suction cup and cardiac harness are on the left side of the schematic, and the ejection tube 183 is on the right hand side of the schematic. For clarity, the dilator tube and the introducer tube have been omitted, however, in practice the cardiac harness would be mounted in the dilator tube, and the dilator tube would extend into the introducer tube, while the ejection tube would extend into the dilator tube. As can be seen in FIG. 42, the leads 31,132 extend through lumens 188, while the tubing 157 associated with the suction cup extends through lumen 189. The tubing and the leads extend proximally out of the proximal end of the ejection tube, and extend out of the patient during delivery of the harness. As previously described, after the introducer is positioned through the rib cage, and the apex of the heart is acquired by the suction cup, the harness can be advanced out of the dilator by advancing the ejection tube 183 in a distal direction toward the apex of the heart. The leads, the cardiac harness and electrodes all provide sufficient column strength to allow the plate 186 to impart a pushing force against the cardiac harness to advance it distally over the heart as previously described. After the cardiac harness is pushed over the epicardial surface of the heart, the ejection tube can be withdrawn proximally so that the tubing 157 and the leads 31,132 slide through lumens 189,188 respectively. The ejection tube 183 continues to be withdrawn proximally so that the proximal end of the leads and the proximal end of tubing 157 are pulled through the distal end 184 of the ejection tube so that the ejection tube is clear of the leads and the tubing.

As with the previous embodiment, suitable materials for the delivery system 140,180 can include the class of polymers typically used and approved for biocompatible use within the body. Preferably, the tubing associated with delivery systems 140 and 180 are rigid, however, they can be formed of a more flexible material. Further, the delivery systems 140,180 can be curved rather than straight, or can have a flexible joint in order to more appropriately maneuver the cardiac harness 20,60,100 over the epicardial surface of the heart during delivery. Further, the tubing associated with delivery systems 140,180 can be coated with a lubricious material to facilitate relative movement between the tubes. Lubricious materials commonly known in the art such as Teflon™ can be used to enhance slidable movement between the tubes.

Delivery and implantation of an ICD, CRT-D, pacemaker, leads, and any other device associated with the cardiac rhythm management devices can be performed by means well known in the art. Preferably, the ICD/CRT-D/pacemaker, are delivered through the same minimally invasive access site as the cardiac harness, electrodes, and leads. The leads are then connected to the ICD/CRT D/pacemaker in a known manner. In one embodiment of the invention, the ICD or CRT-D or pacemaker (or combination device) is implanted in a known manner in the abdominal area and then the leads are connected. Since the leads extend from the apical ends of the electrodes (on the cardiac harness) the leads are well positioned to attach to the power source in the abdominal area.

It may be desired to reduce the likelihood of the development of fibrotic tissue over the cardiac harness so that the elastic properties of the harness are not compromised. Also, as fibrotic tissue forms over the cardiac harness and electrodes over time, it may become necessary to increase the power of the pacing stimuli. As fibrotic tissue increases, the right and left ventricular thresholds may increase, commonly referred to as "exit block." When exit block is detected, the pacing therapy may have to be adjusted. Certain drugs such as steriods, have been found to inhibit cell growth leading to scar tissue or fibrotic tissue growth. Examples of therapeutic drugs or pharmacologic compounds that may be loaded onto the cardiac harness or into a polymeric coating on the harness, on a polymeric sleeve, on individual undulating strands on the harness, or infused through the lumens in the electrodes and delivered to the epicardial surface of the heart include steroids, taxol, aspirin, prostaglandins, and the like. Various therapeutic agents such as antithrombogenic or antiproliferative drugs are used to further control scar tissue formation. Examples of therapeutic agents or drugs that are suitable for use in accordance with the present invention include 17-beta estradiol, sirolimus, everolimus, actinomycin D (ActD), taxol, paclitaxel, or derivatives and analogs thereof. Examples of agents include other antiproliferative substances as well as antineoplastic, antiinflammatory, antiplatelet, anticoagulant, antifibrin, antithrombin, antimitotic, antibiotic, and antioxidant substances. Examples of antineoplastics include taxol (paclitaxel and docetaxel). Further examples of therapeutic drugs or agents include antiplatelets, anticoagulants, antifibrins, antiinflammatories, antithrombins, and antiproliferatives. Examples of antiplatelets, anticoagulants, antifibrins, and antithrombins include, but are not limited to, sodium heparin, low molecular weight heparin, hirudin, argatroban, forskolin, vapiprost, prostacyclin and prostacyclin analogs, dextran, D phe pro arg chloromethylketone (synthetic antithrombin), dipyridamole, glycoprotein IIb/IIIa platelet membrane receptor antagonist, recombinant hirudin, thrombin inhibitor (available from Biogen located in Cambridge, Mass.), and 7E 3B (an antiplatelet drug from Centocor located in Malvern, Pa.). Examples of antimitotic agents include methotrexate, azathioprine, vincristine, vinblastine, fluorouracil, adriamycin, and mutamycin. Examples of cytostatic or antiproliferative agents include angiopeptin (a somatostatin analog from Ibsen located in the United Kingdom), angiotensin converting enzyme inhibitors such as Captopril® (available from Squibb located in New York, N.Y.), Cilazapril® (available from Hoffman LaRoche located in Basel, Switzerland), or Lisinopril® (available from Merck located in Whitehouse Station, N.J.); calcium channel blockers (such as Nifedipine), colchicine, fibroblast growth factor (FGF) antagonists, fish oil (omega 3 fatty acid), histamine antagonists, Lovastatin® (an inhibitor of HMG CoA reductase, a cholesterol lowering drug from Merck), methotrexate, monoclonal antibodies (such as PDGF receptors), nitroprusside, phosphodiesterase inhibitors, prostaglandin inhibitor (available from GlaxoSmithKline located in United Kingdom), Seramin (a PDGF antagonist), serotonin blockers, steroids, thioprotease inhibitors, triazolopyrimidine (a PDGF antagonist), and nitric oxide. Other therapeutic drugs or agents which may be appropriate include alpha interferon, genetically engineered epithelial cells, and dexamethasone.

Referring now to FIGS. 43 to 46, another embodiment of a system for treating a patient's heart has been contemplated, that includes a defibrillation compatible cardiac harness 200 and a leadless defibrillator 202. The cardiac harness of this embodiment is configured to conform generally to at least a portion of a patient's heart and does not include any electrodes or leads. Several embodiments of a defibrillation compatible cardiac harness are described in U.S. Provisional Patent Application No. 60/458,991, filed on Mar. 28, 2003, titled "Multi-Panel Cardiac Harness", now U.S. Non-Provisional Patent Application Ser. No. 10/811,245, which is hereby incorporated by reference in its entirety. The defibrillation compatible cardiac harness may include undulating strands that form panels or rings, and the harness is configured to provide no electrical continuity circumferentially about the harness. Thus, when a defibrillator is used to shock a patient's heart, the electric current created by the defibrillator in not conducted around the heart through the harness. Instead, the electric current passes through the heart, and the effectiveness of the defibrillator is not defeated by the presence of the harness. To prevent an electric current from being conducted around the harness, the undulating strands are coated with a dielectric material and are connected to adjacent strands by connectors that are formed of a dielectric material. Coating the cardiac harness with a dielectric material prevents the harness from developing into a Faraday cage. The cardiac harness may also include a plurality of engaging elements that provide a gripping force between the cardiac harness and the outer surface of the heart to prevent the harness from migrating off of the heart. Other embodiments of a cardiac harness suitable for use with the leadless defibrillator 202 are shown in FIGS. 9–14, where coils separate panels of undulating strands.

The leadless defibrillator 202 can be an ICD having no lead system. An example of a leadless defibrillator is disclosed in U.S. Pat. No. 6,647,292 (Bardy et al.), the entire contents of which are incorporated herein by reference. A housing 204 of the leadless defibrillator contains a source of electrical energy, a capacitor, and sensing circuitry, and the leadless defibrillator includes at least a pair of electrodes 206 disposed on the housing and electrically interfaced to the circuitry. The pair of electrodes is disposed on opposite ends of the housing to deliver high voltage cardioversion/defibrillation energy across the heart. In one embodiment, there is at least a pair of sensing electrodes 208 disposed on the housing of the leadless defibrillator and the sensing electrodes are electrically insulated from the housing and electrically interfaced to the circuitry. These sensing electrodes are spaced far enough apart from one another to provide good QRS detection. The housing of the leadless defibrillator has a generally curved shape following the contour of the heart and it is made of a biocompatible material. Patients having cardiac disease and especially congestive heart failure have hearts in all different sizes, therefore the housing of the leadless defibrillator will be sized and shaped to fit partially around but not touching the patient's heart.

The housing 204 of the leadless defibrillator 202 should be able to provide maximum voltage ranging from about 750 V (volts) to about 2000 V and have an associated maximum energy of about 40 J (joules) to about 200 J. The capacitance of the leadless defibrillator should range from about 50 to about 200 micro farads.

The circuitry of the leadless defibrillator 202 is programmed to monitor the heart rhythms and sense whether or not there is a life threatening ventricular arrhythmia. The detection rate range of the circuitry may be changed to meet the needs of a patient based on several personal factors related to the patient.

In one preferred method of use, the leadless defibrillator 202 will be positioned partially around the cardiac harness 200 (but not touching) and will be located between the left mid-clavicular line approximately at the level of the inframammary crease near the fifth rib and the posterior axillary line, just lateral to the left scapula. At this position, the leadless defibrillator will be able to deliver a current to the ventricular myocardium through the cardiac harness. In another preferred embodiment, the leadless defibrillator will be subcutaneously implanted near the same minimally invasive access site that the cardiac harness is delivered through.

In this embodiment, the cardiac harness 200 having no leads is used in conjunction with the leadless defibrillator 202 and can simultaneously treat multiple cardiac failures including congestive heart failure, cardiac arrhythmias, bradycardia and tachycardia. The cardiac harness is able to provide a compressive force on a heart during at least a portion of the cardiac cycle, while the leadless defibrillator is able to provide defibrillation and pacing functions.

Figure 43:
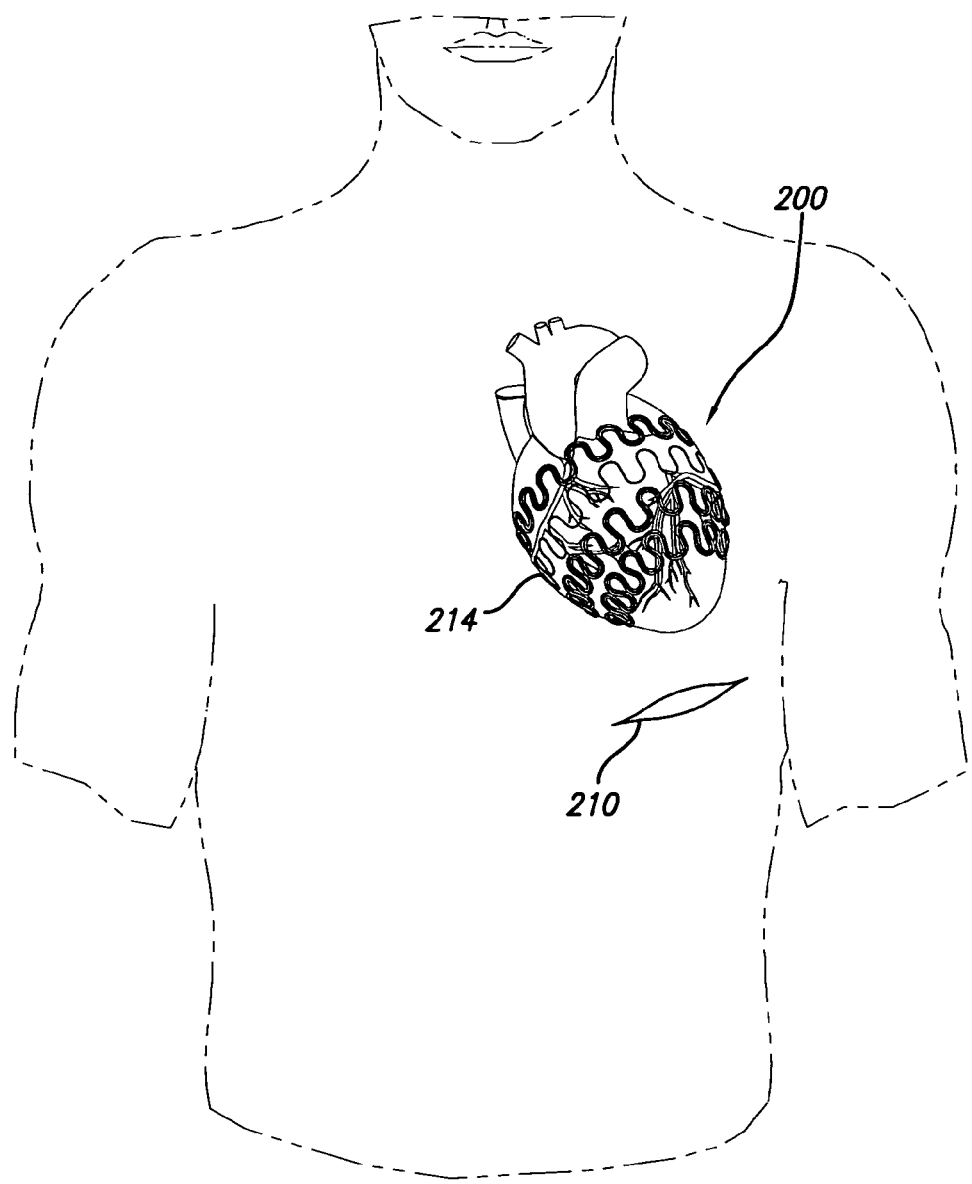
FIG. 43 depicts a schematic view of a cardiac harness mounted on a human heart.

Still referring to FIGS. 43 to 46, one method of implanting a cardiac harness 200 and a leadless defibrillator 202 will now be described. FIG. 43 shows the torso of a human patient with a lateral incision 210 that provides a minimally invasive access site between the ribs for delivery of the harness and leadless defibrillator. This incision can be about 0.1 cm to about 10 cm, and is more typically about 1 cm to about 10 cm. The cardiac harness will be delivered through this incision by a delivery device and placed around the heart as previously described above with reference to FIGS. 27–42.

Figure 44:
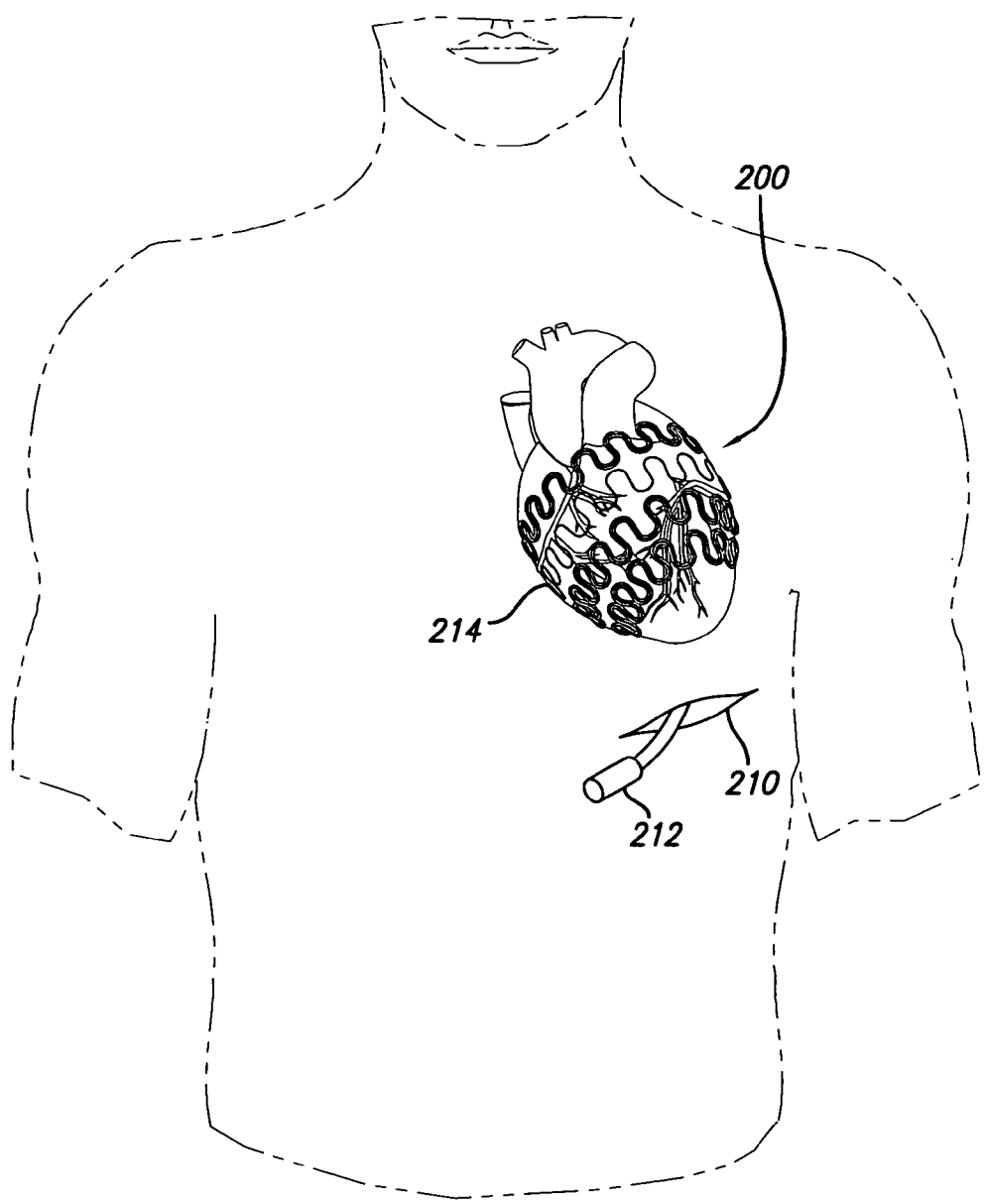
FIG. 44 depicts a schematic view of the cardiac harness mounted on a human heart and an introducer being inserted through a lateral incision to form a subcutaneous pocket.
Figure 45:
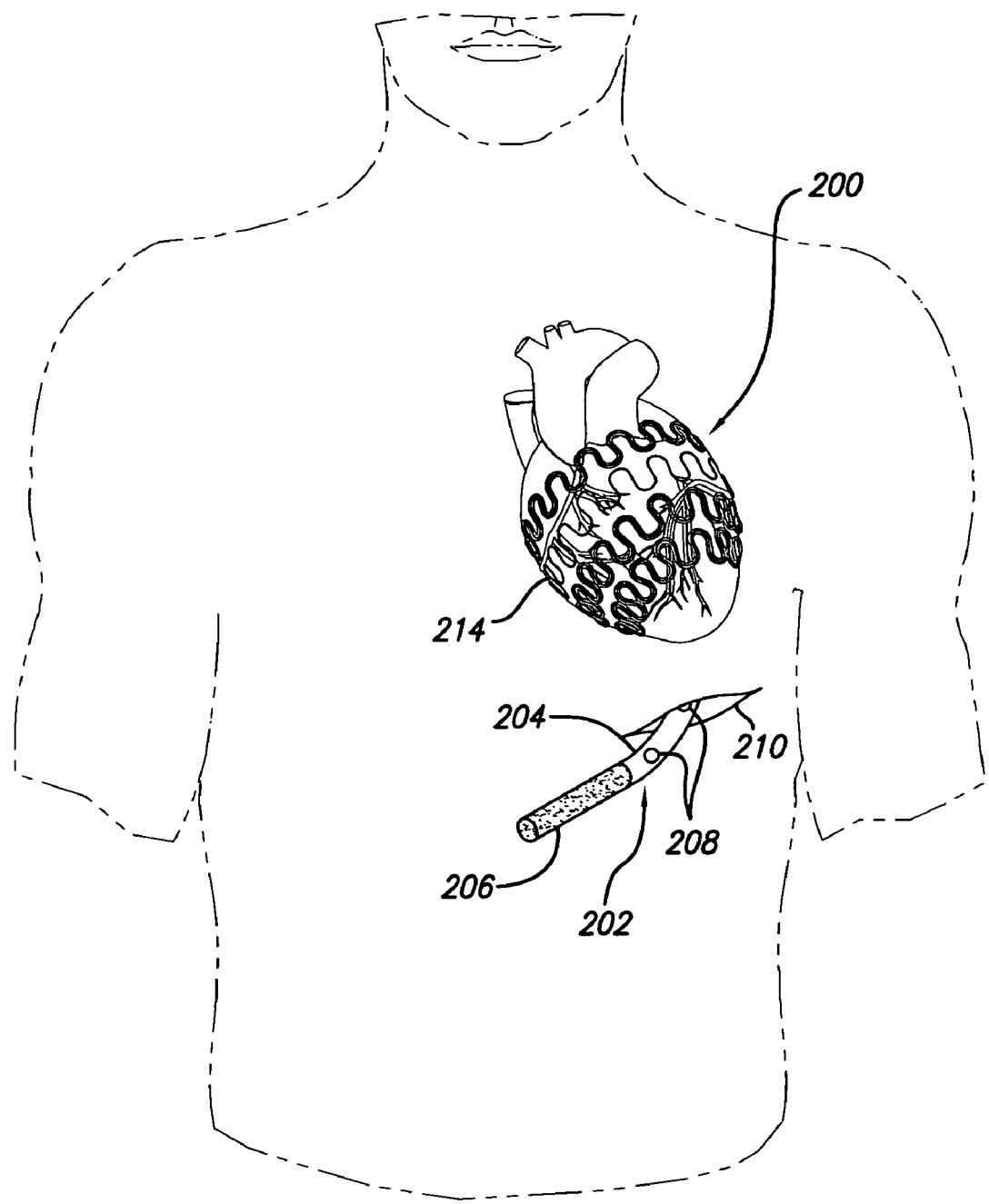
FIG. 45 depicts a schematic view of the cardiac harness mounted on a human heart and a leadless defibrillator being implanted through the lateral incision.
Figure 46:
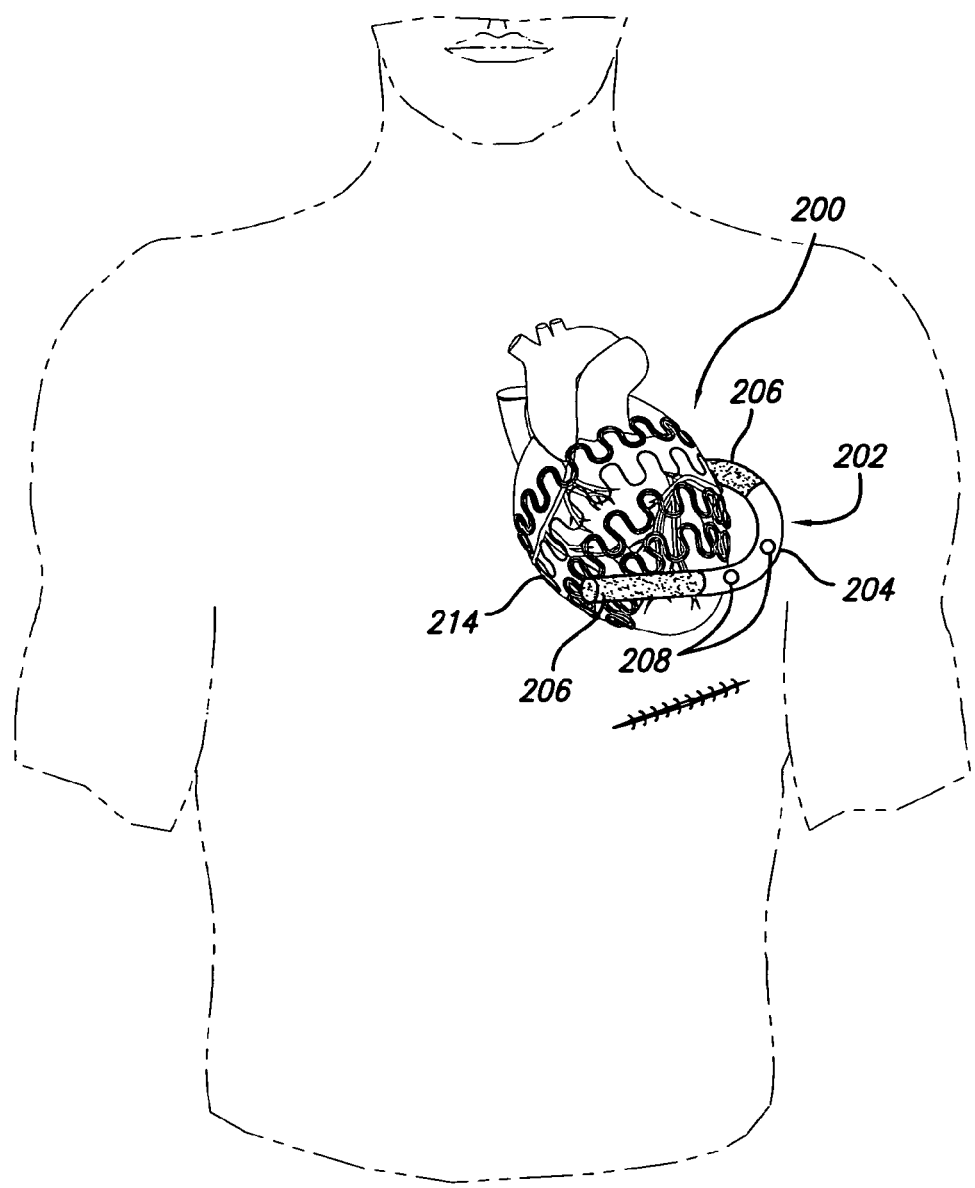
FIG. 46 depicts a schematic view of the cardiac harness and the leadless defibrillator partially surrounding the heart.

After the delivery device used to position the cardiac harness 200 around the heart is removed from the patient, an introducer 212 is then inserted into the incision 210 as shown in FIG. 44 to allow placement of the leadless defibrillator 202. In one embodiment, the subcutaneous pocket is formed medially to the inframammary crease and extends posteriorly to the left posterior axillary line. Once the subcutaneous pocket is formed, the leadless defibrillator is implanted in the subcutaneous pocket through the incision 210 as shown in FIG. 45. The leadless defibrillator is positioned to partially surrounding the heart (but does not touch the heart) and cardiac harness, as shown in FIG. 46.

By using the same minimally invasive access site to position the cardiac harness and the leadless defibrillator, relatively little trauma is caused to the patient from this surgery.

After the leadless defibrillator 202 is implanted into the patient, any necessary diagnostics, testing and programming may be performed prior to closure of the incision 210. FIG. 46 shows the leadless defibrillator in position around the harness and the incision closed.

In another method of implanting the cardiac harness 200 and the leadless defibrillator 202, two separate incisions forming separate access sites may be formed. In this embodiment, the cardiac harness and leadless defibrillator are delivered to the heart through separate access sites. In still another embodiment, two separate surgical procedures can be performed to implant either the cardiac harness or the leadless defibrillator, and then on a later date the remaining device can be implanted.

In yet another embodiment of a system for treating the heart, a cardiac harness includes an antenna 214 for transmitting QRS signals of the heart to a defibrillator. Any defibrillation compatible cardiac harness can be used for this embodiment, including those harnesses disclosed above or those disclosed in U.S. Provisional Patent Application No. 60/458,991, which is already incorporated by reference in its entirety. The cardiac harness shown in FIGS. 9–14, where coils separate panels of undulating strands may also be used. These cardiac harnesses include undulated strands formed from a metal wire that comprise panels or rings that are interconnected. In some cardiac harness embodiments, the panels are connected together with coils. The metallic strands of the harnesses are coated with a dielectric material to prevent electricity from being conducted around the harness when it is placed on a heart.

To form an RF antenna 214 on the cardiac harness, some of the harness loops or undulations or coils or panels or coils connecting panels (depending on the harness configuration) will not be covered with a dielectric coating. In some embodiments, only a specific length of the coil, ring or panel will not be covered with a dielectric element, and in others the entire coil, panel or ring may be uncovered. Still in other embodiments, more than one coil, ring or panel will not be covered with a dielectric coating. Therefore, the electric signals provided by the heart will be transmitted through the bare metal wire of the coil or the cardiac harness that is in contact with the heart's surface, and will be received by the defibrillator. The defibrillator may be an external defibrillator, an automatic external defibrillator ("AED"), or a leadless defibrillator implanted near the heart as described above. The electrical signal from the heart will pass through the antenna creating a magnetic field that can then be sensed by the defibrillator. The antenna formed on the cardiac harness will increase the signal from the heart being sensed by electrodes on the defibrillator.

The antenna 214 or antennas created on the cardiac harness 200 can also be used to help provide a more efficient defibrillation shock that is channeled through the heart. In other words, the antenna can act as a "lightening rod" when the defibrillator sends an electric shock to the heart. When the shock is discharged from the defibrillator, the antenna can re-channel the energy vector created by the defibrillator, directing the energy towards the antenna and then through the heart.

Although the present invention has been described in terms of certain preferred embodiments, other embodiments that are apparent to those of ordinary skill in the art are also within the scope of the invention. Accordingly, the scope of the invention is intended to be defined only by reference to the appended claims. While the dimensions, types of materials and coatings described herein are intended to define the parameters of the invention, they are by no means limiting and are exemplary embodiments.

We claim:

1. A method of implanting a cardiac harness and a leadless defibrillator, comprising:
   providing a cardiac harness formed from a metal alloy;
   providing a leadless defibrillator;
   coating the metal alloy with a dielectric material to electrically insulate the cardiac harness from a defibrillating shock;
   providing a minimally invasive access site;
   inserting the cardiac harness through the minimally invasive access site and around at least a portion of the heart; and
   inserting the leadless defibrillator through the minimally invasive access site and around a portion of the cardiac harness.

2. The method of claim 1, further comprising providing a delivery device for carrying the cardiac harness.

3. The method of claim 1, further comprising providing an introducer and inserting the introducer into the minimally invasive access site to create a subcutaneous pocket for inserting the leadless defibrillator.

4. The method of claim 1, further comprising performing diagnostics, testing, and programming of the leadless defibrillator prior to closure of the minimally invasive access site.

5. The method of claim 1, wherein the minimally invasive access site is positioned between the ribs.

6. The method of claim 1, further comprising making an incision in the pericardium so that the cardiac harness is mounted on the epicardial surface of the heart and under the pericardium.

7. The method of claim 1, wherein the leadless defibrillator includes a housing containing a source of electrical energy, a capacitor, and cardioversion-defibrillation circuitry, and the leadless defibrillator includes a pair of electrodes formed on opposite ends of the housing and electrically interfaced to the cardioversion-defibrillation circuitry.

8. The method of claim 7, wherein the leadless defibrillator includes at least one sensing electrode disposed on the housing.

9. The method of claim 1, wherein the dielectric material is a silicone rubber material coated onto the metal alloy cardiac harness to insulate the harness from an electrical shock delivered by the leadless defibrillator.

10. The method of claim 9, wherein the cardiac harness includes undulating strands that are interconnected.

11. The method of claim 9, wherein the cardiac harness includes a gripping element to increase gripping force between the cardiac harness and the outer surface of the heart.

12. The method of claim 1, wherein the leadless defibrillator senses electrical signals from the heart and provides a defibrillating shock through the cardiac harness and through the heart.

* * * * *